United States Patent [19]
Goldstein et al.

[11] Patent Number: 5,912,120
[45] Date of Patent: Jun. 15, 1999

[54] CLONING, EXPRESSION AND DIAGNOSIS OF HUMAN CYTOCHROME P450 2C19: THE PRINCIPAL DETERMINANT OF S-MEPHENYTOIN METABOLISM

[75] Inventors: Joyce A. Goldstein, Raleigh, N.C.; Sonia M.F. De Morais, Newtown, Conn.

[73] Assignee: The United States of America as represented by the Department of Health and Human Services, Washington, D.C.

[21] Appl. No.: 08/238,821

[22] Filed: May 6, 1994

Related U.S. Application Data

[63] Continuation-in-part of application No. 08/201,118, Feb. 22, 1994, which is a continuation-in-part of application No. 07/864,962, Apr. 9, 1992, abandoned.

[51] Int. Cl.$^6$ .............................. C12Q 1/68; C12N 9/18; C07H 19/00; C07H 21/00
[52] U.S. Cl. .......................... 435/6; 435/197; 536/22.1; 536/23.1; 536/23.2; 536/23.5; 536/24.3; 536/24.31; 536/24.33
[58] Field of Search ...................... 435/197, 6; 536/22.1, 536/23.1, 23.2, 23.5, 24.3, 24.31, 24.33

[56] References Cited

FOREIGN PATENT DOCUMENTS 463 395   2/1992   European Pat. Off. .

OTHER PUBLICATIONS de Morais et al., "Gene structure and upstream regulatory regions of human CYP2C9 and CYP2C18," *Biochemical and Biophysical Research Comm.* 194(1):194–200 (1993).

Glover, David M., "Gene cloning: The mechanics of DNA manipulation," pp. 1–20; 110–126; 179–213 (Chapman and Hall Ltd., London (1984)).

Goldstein et al., "Evidence that CYP2C19 is the major (S)–mephenytoin 4'–hydroxylase in humans," *Biochemistry* 33:1743–1752 (1994).

Kaminsky et al., "Correlation of human cytochrome P4502C substrate specificities with primary structure: warfarin as a probe," *Molecular Pharmacology* 43(2):234–239 (1993).

Küpfer et al., "Pharmacogenetics of mephenytoin: a new drug hydroxylation polymorphism in man," *Eur. J. Clin. Pharmacol.* 26:753–759 (1984).

Nakamura et al., "Interethnic differences in genetic polymorphism of debrisoquin and mephenytoin hydroxylation between Japanese and Caucasian populations," *Clin. Pharmacol. Ther.* 38(4):402–408 (1985).

Romkes et al., "Cloning and expression of complementary DNAs for multiple members of the human cytochrome P450IIC subfamily," *Biochemistry* 32:1390 (1993) [Correction to *Biochemistry* 30:3247–3255 (1991)].

Romkes et al., "Cloning and expression of complementary DNAs for multiple members of the human cytochrome P4502C subfamily," *FASEB* p. A1163, Abstract 4595 (1991).

Srivastava et al., "Separation of human liver microsomal tolbutamide hydroxylase and (S)–mephenytoin 4'–hydroxylase cytochrome P–450 enzymes," *Mol. Pharmacol.* 40:69–69 (1991).

Yasumori et al., "Expression of a human P–450IIC gene in yeast cells using galactose–inducible expression system," *Mol. Pharmacol.* 35:443–449 (1990).

Wrighton et al., "Purification and characterization of human liver cytochrome P450 2C19, the S–mephenytoin 4'–hydroxylase," 5th European ISSX Meeting, Abstract 69 (Sep. 1993).

Wrighton et al., "Isolation and characterization of human liver cytochrome P450 2C19: correlation between 2C19 and S–mephenytoin 4'–hydroxylation," *Archives Biochem. Biophys.* 306, 240–245 (Oct. 1993).

Romkes et al., "Cloning and Expression of Complementary DNAs for Multiple Members of the Human Cytochrome P450IIC Subfamily," Biochemistry vol. 30, pp. 3247–3255, 1991.

Shimada et al., "Human Liver Microsomal Cytochrome P–450 . . . ," Journal of Biological Chemistry vol. 261, No. 2, Jan. 15, 1986, pp. 909–921.

Umbenhauer et al., "Cloning and Sequenc Determination of a Complementary DNA . . .", Biochemistry vol. 26, pp. 1094–1099, 1987.

*Primary Examiner*—Charles L. Patterson, Jr.
*Assistant Examiner*—Hyosuk Kim
*Attorney, Agent, or Firm*—Townsend and Townsend and Crew LLP

[57] ABSTRACT

The invention provides two novel members of the cytochrome P450 2C subfamily of enzymes, designated 2C18 and 2C19. DNA segments encoding these enzymes are also provided. The 2C19 polypeptide represents the principal human determinant of human S-mephenytoin 4'-hydroxylase activity. The invention also provides methods of identifying drugs metabolized by S-mephenytoin 4'-hydroxylase activity. Drugs shown to be metabolized by this activity should in general not be administered to individuals having, or belong to an ethnic group at risk of, a polymorphic deficiency in S-mephenytoin 4'-hydroxylase activity. The invention also provides methods of diagnosing individuals having a polymorphic deficiency.

37 Claims, 30 Drawing Sheets

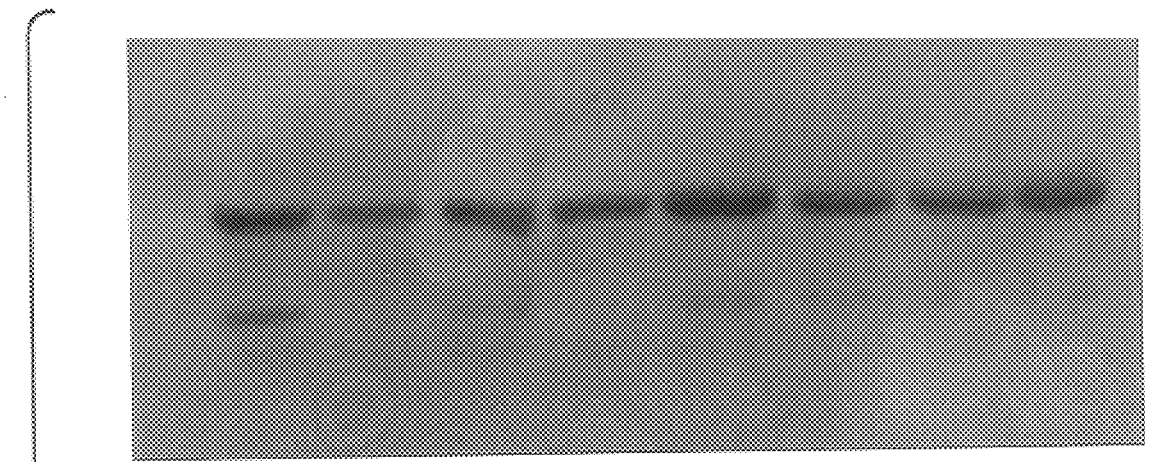
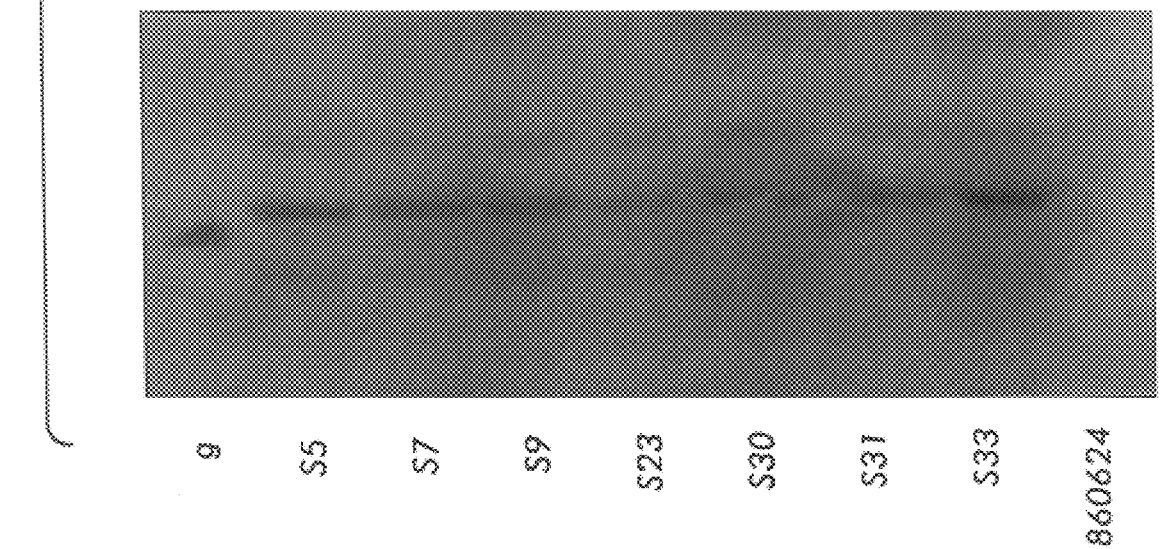
FIG. 1

```
         -200                                                           -150
  2c     ..........  ..........  ..........  ..........  ..........
  2c8    ..........  ..........  ..........  ..........  ..........
   25    ..........  ..........  ..........  ..........  ..........
   65    ..........  ..........  ..........  ..........  ..........
  29c    .GGCACCGGA  AAGAACAAGA  AAAAAGAACA  CCTTATTTTT  ATCTTCTTCA
   6b    ..........  ..........  ..........  ..........  ..........
  11a    ..........  ..........  ..........  ..........  ..........

-151                                                           -100
  2c     ..........  ..........  ..........  ..........  ..........
  2c8    ..........  ..........  ..........  ..........  ..........
   25    ..........  ..........  ..........  ..........  ..........
   65    ..........  ..........  ..........  ..........  ..........
  29c    GTGAGCCAAT  GTTCATTCAA  AAGAGAGATT  AAAGTGCTTT  TTGCTGACTA
   6b    ..........  ..........  ..........  ..........  ..........
  11a    ..........  ..........  ..........  ..........  ..........

-101                                                            -50
  2c     ..........  ..........  ..........  ..........  ..........
  2c8    ..........  ..........  ..........  ..........  ..........
   25    ..........  ..........  ..........  ..........  ..........
   65    ..........  ..........  ..........  ..........  ..........
  29c    GTCACAGTCA  GAGTCAGAAT  CACAGGTGGA  TTAGTAGGGA  GTGTTATAAA
   6b    ..........  ..........  ..........  ..........  ..........
  11a    ..........  ..........  ..........  ..........  ..........

-51                                                             -1
  2c     ........AG  TGAAAGCCCG  CAGTTGTCTT  ACTAAGAAGA  GAAG.CTTCA
  2c8    ..........  ..........  ..........  ..........  ..........A
   25    ..........  ..........  ..........  ........GA  GAAGGCTTCA
   65    ..........  ..........  ..........  ..........  GAAGGCTTCA
  29c    AGCCTTGAAG  TGAAAGCCCG  CAGTTGTCTT  ACTAAGAAGA  GAAGCCTTCA
   6b    ........AG  TGAAAGCCCG  CAGTTGTCTT  ACTAAGAAGA  GAAGCCTTCA
  11a    ..........  ..........  ..........  ..........  .....CTTCA 1                                                             50
  2c     ATGGAtcCt.  tTGTGGtcCT  .GTGCTcTGT  CTCTCaTgTt  TGcTTCTCcT
  2c8    ATGGAACCTT  TTGTGGTCCT  GGTGCTGTGT  CTCTCTTTTA  TGCTTCTCTT
   25    ATGGATTCTC  TTGTGGTCCT  TGTGCTCTGT  CTCTCATGTT  TGCTTCTCCT
   65    ATGGATTCTC  TTGTGGTCCT  TGTGCTCTGT  CTCTCATGTT  TGCTTCTCCT
  29c    ATGGATCCAG  CTGTGGCTCT  GGTGCTCTGT  CTCTCCTGTT  TGTTTCTCCT
   6b    ATGGATCCAG  CTGTGGCTCT  GGTGCTCTGT  CTCTCCTGTT  TGTTTCTCCT
  11a    ATGGATCCTT  TTGTGGTCCT  TGTGCTCTGT  CTCTCATGTT  TGCTTCTCCT
```

FIG. 2-1.

```
        51                                                                      100
 2c  TTCAcTCTGG  AGaCAGAGCT  cTgGgAGAgG  .Aa.CTCCCt  cCTGGCCCCA
 2c8 TTCACTCTGG  AGACAGAGCT  GTAGGAGAAG  GAAGCTCCCT  CCTGGCCCCA
 25  TTCACTCTGG  AGACAGAGCT  CTGGGAGAGG  AAAACTCCCT  CCTGGCCCCA
 65  TTCACTCTGG  AGACAGAGCT  CTGGGAGAGG  AAAACTCCCT  CCTGGCCCCA
 29c TTCACTCTGG  AGGCAGAGCT  CTGGAAGAGG  GAGGCTCCCG  TCTGGCCCCA
 6b  TTCACTCTGG  AGGCAGAGCT  CTGGAAGAGG  GAGGCTCCCG  TCTGGCCCCA
 11a TTCAATCTGG  AGACAGAGCT  CTGGGAGAGG  AAAACTCCCT  CCTGGCCCCA 151                                                                     200
 2c  aGCAAATCcT  TaACCAAT.T  CTCAAAagTC  TATGGcCCTG  TGTTCACt.T
 2c8 TGCAAATCTT  TCACCAATTT  CTCAAAAGTC  TATGGTCCTG  TGTTCACCGT
 25  AGCAAATCCT  TAACCAATCT  CTCAAAGGTC  TATGGCCCTG  TGTTCACTCT
 65  AGCAAATCCT  TAACCAATCT  CTCAAAGGTC  TATGGCCCTG  TGTTCACTCT
 29c AGCAAATCCT  TAACCAATTT  CTCAAAAGTC  TATGGCCCTG  TGTTCACTGT
 6b  AGCAAATCCT  TAACCAATTT  CTCAAAAGTC  TATGGCCCTG  TGTTCACTGT
 11a AGCAAATCCT  TAACCAATCT  CTCAAAAATC  TATGGCCCTG  TGTTCACTCT 201                                                                     250
 2c  GTATTTTGGC  cTGaAaCcCA  TaGTGGTG.T  gCATGGATAT  GAaGcaGTGA
 2c8 GTATTTTGGC  ATGAATCCCA  TAGTGGTGTT  TCATGGATAT  GAGGCAGTGA
 25  GTATTTTGGC  CTGAAACCCA  TAGTGGTGCT  GCATGGATAT  GAAGCAGTGA
 65  GTATTTTGGC  CTGAAACCCA  TAGTGGTGCT  GCATGGATAT  GAAGCAGTGA
 29c GTATTTTGGC  CTGAAGCCCA  TTGTGGTGTT  GCATGGATAT  GAAGCAGTGA
 11a GTATTTTGGC  CTGGAACGCA  TGGTGGTGCT  GCATGGATAT  GAAGTGGTGA 251                                                                     300
 2c  AGGAaGCCCT  GATTGATc.T  GGAGAGGAGT  TTTCTGGAAG  AGGca.TTtc
 2c8 AGGAAGCCCT  GATTGATAAT  GGAGAGGAGT  TTTCTGGAAG  AGGCAATTCC
 25  AGGAAGCCCT  GATTGATCTT  GGAGAGGAGT  TTTCTGGAAG  AGGCATTTTC
 65  AGGAAGCCCT  GATTGATCTT  GGAGAGGAGT  TTTCTGGAAG  AGGCATTTTC
 29c AGGAGGCCCT  GATTGATCAT  GGAGAGGAGT  TTTCTGGAAG  AGGAAGTTTT
 6b  AGGAGGCCCT  GATTGATCAT  GGAGAGGAGT  TTTCTGGAAG  AGGAAGTTTT
 11a AGGAAGCCCT  GATTGATCTT  GGAGAGGAGT  TTTCTGGAAG  AGGCCATTTC 301                                                                     350
 2c  CCAcTggCTg  AAAgAg.TAa  cA.AGGA.TT  GGAATcgTTT  tCAGCAATGG
 2c8 CCAATATCTC  AAAGAATTAC  TAAAGGACTT  GGAATCATTT  CCAGCAATGG
 25  CCACTGGCTG  AAAGAGCTAA  CAGAGGATTT  GGAATTGTTT  TCAGCAATGG
 65  CCACTGGCTG  AAAGAGCTAA  CAGAGGATTT  GGAATTGTTT  TCAGCAATGG
 29c CCAGTGGCTG  AAAAGTTAA   CAAAGGACTT  GGAATCCTTT  TCAGCAATGG
 6b  CCAGTGGCTG  AAAAGTTAA   CAAAGGACTT  GGAATCCTTT  TCAGCAATGG
 11a CCACTGGCTG  AAAGAGCTAA  CAGAGGATTT  GGAATCGTTT  TCAGCAATGG
```

*FIG. 2-2.*

```
      351                                                              400
 2c  AAAGAgATGG  AAGGAGATCC  GGCGTTTCTc  CCTCAtgAcg  cTGCGGAATT
2c8  AAAGAGATGG  AAGGAGATCC  GGCGTTTCTC  CCTCACAAAC  TTGCGGAATT
 25  AAAGAAATGG  AAGGAGATCC  GGCGTTTCTC  CCTCATGACG  CTGCGGAATT
 65  AAAGAAATGG  AAGGAGATCC  GGCGTTTCTC  CCTCATGACG  CTGCGGAATT
29c  AAAGAGATGG  AAGGAGATCC  GGCGTTTCTG  CCTCATGACT  CTGCGGAATT
 6b  AAAGAGATGG  AAGGAGATCC  GGCGTTTCTG  CCTCATGACT  CTGCGGAATT
11a  AAAGAGATGG  AAGGAGATCC  GGCGTTTCTC  CCTCATGACG  CTGCGGAATT 401                                                              450
 2c  TTGGGATGGG  GAAGAGGAGC  ATtGAGGACC  GTGTTCAAGA  GGAAGCcCgC
2c8  TTGGGATGGG  GAAGAGGAGC  ATTGAGGACC  GTGTTCAAGA  GGAAGCTCAC
 25  TTGGGATGGG  GAAGAGGAGC  ATTGAGGACC  GRGRRCAAGA  GGAAGCCCGC
 65  TTGGGATGGG  GAAGAGGAGC  ATTGAGGACC  GTGTTCAAGA  GGAAGCCCGC
29c  TTGGGATGGG  GAAGAGGAGC  ATCGAGGACC  GTGTTCAAGA  GGAAGCCCGC
 6b  TTGGGATGGG  GAAGAGGAGC  ATCGAGGACC  GTGTTCAAGA  GGAAGCCCGC
11a  TTGGGATGGG  GAAGAGGAGC  ATTGAGGACC  GTGTTCAAGA  GGAAGCCCGC 451                                                              500
 2c  TGCCTTGTGG  AGGAGTTGAG  AAAAACCAAg  GCcTCACCCT  GTGATCCCAC
2c8  TGCCTTGTGG  AGGAGTTGAG  AAAAACCAAG  GCTTCACCCT  GTGATCCCAC
 25  TGCCTTGTGG  AGGAGTTGAG  AAAAACCAAG  GCCTCACCCT  GTGATCCCAC
 65  TGCCTTGTGG  AGGAGTTGAG  AAAAACCAAG  GCCTCACCCT  GTGATCCCAC
29c  TGCCTTGTGG  AGGAGTTGAG  AAAAACCAAT  GCCTCACCCT  GTGATCCCAC
 6b  TGCCTTGTGG  AGGAGTTGAG  AAAAACCAAT  GCCTCACCCT  GTGATCCCAC
11a  TGCCTTGTGG  AGGAGTTGAG  AAAAACCAAG  GCTTCACCCT  GTGATCCCAC 501                                                              550
 2c  TTTCATCCTG  GGCTGTGCTC  CCTGCAATGT  GATCTGCTCc  .TTaTTTTCC
2c8  TTTCATCCTG  GGCTGTGCTC  CCTGCAATGT  GATCTGCTCC  GTTGTTTTCC
 25  TTTCATCCTG  GGCTGTGCTC  CCTGCAATGT  GATCTGCTCC  ATTATTTTCC
 65  TTTCATCCTG  GGCTGTGCTC  CCTGCAATGT  GATCTGCTCC  ATTATTTTCC
29c  TTTCATCCTG  GGCTGTGCTC  CCTGCAATGT  GATCTGCTCT  GTTATTTTCC
 6b  TTTCATCCTG  GGCTGTGCTC  CCTGCAATGT  GATCTGCTCT  GTTATTTTCC
11a  TTTCATCCTG  GGCTGTGCTC  CCTGCAATGT  GATCTGCTCC  ATTATTTTCC 551                                                              600
 2c  AtaAaCG.TT  tGATTATAAA  GATCAG.aaT  TTCTtAaCtT  gATGgAAAaa
2c8  AGAAACGATT  TGATTATAAA  GATCAGAATT  TTCTCACCCT  GATGAAAAGA
 25  ATAAACGTTT  TGATTATAAA  GATCAGCAAT  TTCTTAACTT  AATGGAAAAG
 65  ATAAACGTTT  TGATTATAAA  GATCAGCAAT  TTCTTAACTT  AATGGAAAAG
29c  ATGATCGATT  TGATTATAAA  GATCAGAGGT  TTCTTAACTT  GATGGAAAAA
 6b  ATGATCGATT  TGATTATAAA  GATCAGAGGT  TTCTTAACTT  GATGGAAAAA
11a  AGAAACGTTT  CGATTATAAA  GATCAGCAAT  TTCTTAACTT  GATGGAAAAA
```

*FIG. 2-3.*

```
       601                                                           650
  2c  TT.AATGAAA ACaTCAgGAT TcTgAgC.cc CC.TGGATCC AG.TcTGCAA
 2c8  TTCAATGAAA ACTTCAGGAT TCTGAACTCC CCATGGATCC AGGTCTGCAA
  25  TTGAATGAAA ACATCAAGAT TTTGAGCAGC CCCTGGATCC AGATCTGCAA
  65  TTGAATGAAA ACATCAAGAT TTTGAGCAGC CCCTGGATCC AGATCTGCAA
 29c  TTCAATGAAA ACCTCAGGAT TCTGAGCTCT CCATGGATCC AGGTCTGCAA
  6b  TTCAATGAAA ACCTCAGGAT TCTGAGCTCT CCATGGATCC AGGTCTGCAA
 11a  TTGAATGAAA ACATCAGGAT TGTAAGCACC CCCTGGATCC AGATATGCAA 651                                                           700
  2c  TAATTT.cCt cct.TCATtG ATTattTCCC .GGAActCA. AAcAAAtTac
 2c8  TAATTTCCCT CTACTCATTG ATTGTTTCCC AGGAACTCAC AACAAAGTGC
  25  TAATTTTTCT CCTATCATTG ATTACTTCCC GGGAACTCAC AACAAATTAC
  65  TAATTTTTCT CCTATCATTG ATTACTTCCC GGGAACTCAC AACAAATTAC
 29c  TAATTTCCCT GCTCTCATCG ATTATCTCCC AGGAAGTCAT AATAAAATAG
  6b  TAATTTCCCT GCTCTCATCG ATTATCTCCC AGGAAGTCAT AATAAAATAG
 11a  TAATTTTCCC ACTATCATTG ATTATTTCCC GGGAACCCAT AACAAATTAC 701                                                           750
  2c  tTaAAAA.gT TGCTtttAtg aaAAGTtAta TtttGGAgAa AgTAAAAGAA
 2c8  TTAAAAATGT TGCTCTTACA CGAAGTTACA TTAGGGAGAA AGTAAAAGAA
  25  TTAAAAACGT TGCTTTTATG AAAAGTTATA TTTTGGAAAA AGTAAAAGAA
  65  TTAAAAACGT TGCTTTTATG AAAAGTTATA TTTTGGAAAA AGTAAAAGAA
 29c  CTGAAAATTT TGCTTACATT AAAAGTTATG TATTGGAGAG AATAAAAGAA
  6b  CTGAAAATTT TGCTTACATT AAAAGTTATG TATTGGAGAG AATAAAAGAA
 11a  TTAAAAACCT TGCTTTTATG GAAAGTGATA TTTTGGAGAA AGTAAAAGAA 751                                                           800
  2c  CAcCAAGaAT Ca.TGGAcaT gAACAa.cCT CgGGACTTTA TtGATTGcTT
 2c8  CACCAAGCAT CACTGGATGT TAACAATCCT CGGGACTTTA TGGATTGCTT
  25  CACCAAGAAT CAATGGACAT GAACAACCCT CAGGACTTTA TTGATTGCTT
  65  CACCAAGAAT CAATGGACAT GAACAACCCT CAGGACTTTA TTGATTGCTT
 29c  CATCAAGAAT CCCTGGACAT GAACAGTGCT CGGGACTTTA TTGATTGTTT
  6b  CATCAAGAAT CCCTGGACAT GAACAGTGCT CGGGACTTTA TTGATTGTTT
 11a  CACCAAGAAT CGATGGACAT CAACAACCCT CGGGACTTTA TTGATTGCTT 801                                                           850
  2c  CCTGATcAAA ATGGAg.AGG AAAAGcAcAA cCAAcagTCt GAATTtAcTa
 2c8  CCTGATCAAA ATGGAGCAGG AAAAGGACAA CCAAAAGTCA GAATTCAATA
  25  CCTGATGAAA ATGGAGAAGG AAAAGCACAA CCAACCATCT GAATTTACTA
  65  CCTGATGAAA ATGGAGAAGG AAAAGCACAA CCAACCATCT GAATTTACTA
 29c  CCTGATCAAA ATGGAACAGG AAAAGCACAA TCAACAGTCT GAATTTACTG
  6b  CCTGATCAAA ATGGAACAGG AAAAGCACAA TCAACAGTCT GAATTTACTG
 11a  CCTGATCAAA ATGGAGAAGG AAAAGCAAAA CCAACAGTCT GAATTCACTA
```

FIG. 2-4.

```
         851                                                     900
  2c TTGAAAgCTT Ggta..CACT G.AgcTGA.t TgtTTGgaGC TGG.ACAGAG
 2c8 TTGAAAACTT GGTTGGCACT GTAGCTGATC TATTTGTTGC TGGAACAGAG
  25 TTGAAAGCTT GGAAAACACT GCAGTTGACT TGTTTGGAGC TGGGACAGAG
  65 TTGAAAGCTT GGAAAACACT GCAGTTGACT TGTTTGGAGC TGGGACAGAG
 29c TTGAAAGCTT GATAGCCACT GTAACTGATA TGTTTGGGGC TGGAACAGAG
  6b TTGAAAGCTT GATAGCCACT GTAACTGATA TGTTTGGGGC TGGAACAGAG
 11a TTGAAAACTT GGTAATCACT GCAGCTGACT TACTTGGAGC TGGGACAGAG 901                                                     950
  2c ACaACaAGCA C.AC.CTGAG ATATG..CTC CT.CTCCTGC TGAAGcACCC
 2c8 ACAACAAGCA CCACTCTGAG ATATGGACTC CTGCTCCTGC TGAAGCACCC
  25 ACGACAAGCA CAACCCTGAG ATATGCTCTC CTTCTCCTGC TGAAGCACCC
  65 ACGACAAGCA CAACCCTGAG ATATGCTCTC CTTCTCCTGC TGAAGCACCC
 29c ACAACGAGCA CCACTCTGAG ATATGGACTC CTGCTCCTGC TGAAGTACCC
  6b ACAACGAGCA CCACTCTGAG ATATGGACTC CTGCTCCTGC TGAAGTACCC
 11a ACAACAAGCA CAACCCTGAG ATATGCTCTC CTTCTCCTGC TGAAGCACCC 951                                                    1000
  2c AGAGGTCACA GCTAAAGTCC AGGAAGAGAT TGAacgTGTa aTTGGCAGAa
 2c8 AGAGGTCACA GCTAAAGTCC AGGAAGAGAT TGATCATGTA ATTGGCAGAC
  25 AGAGGTCACA GCTAAAGTCC AGGAAGAGAT TGAACGTGTG ATTGGCAGAA
  65 AGAGGTCACA GCTAAAGTCC AGGAAGAGAT TGAACGTGTG ATTGGCAGAA
 29c AGAGGTCACA GCTAAAGTCC AGGAAGAGAT TGAATGTGTA GTTGGCAGAA
  6b AGAGGTCACA GCTAAAGTCC AGGAAGAGAT TGAATGTGTA GTTGGCAGAA
 11a AGAGGTCACA GCTAAAGTCC AGGAAGAGAT TGAACGTGTC ATTGGCAGAA 1001                                                    1050
  2c ACcGGAGCCC CTGCATGCAg GAcAGGaGcC ACATGCCcTA CACaGATGCT
 2c8 ACAGGAGCCC CTGCATGCAG GATAGGAGCC ACATGCCTTA CACTGATGCT
  25 ACCGGAGCCC CTGCATGCAA GACAGGAGCC ACATGCCCTA CACAGATGCT
  65 ACCGGAGCCC CTGCATGCAA GACAGGAGCC ACATGCCCTA CACAGATGCT
 29c ACCGGAGCCC CTGTATGCAG GACAGGAGTC ACATGCCCTA CACAGATGCT
  6b ACCGGAGCCC CTGTATGCAG GACAGGAGTC ACATGCCCTA CACAGATGCT
 11a ACCGGAGCCC CTGCATGCAG GACAGGGGCC ACATGCCCTA CACAGATGCT 1051                                                    1100
  2c GTgGTGCACG AG.TCCAGAG ATACattGAC CT.cTCCCCA CCagccTGCC
 2c8 GTAGTGCACG AGATCCAGAG ATACAGTGAC CTTGTCCCCA CCGGTGTGCC
  25 GTGGTGCACG AGGTCCAGAG ATACCTTGAC CTTCTCCCCA CCAGCCTGCC
  65 GTGGTGCACG AGGTCCAGAG ATACATTGAC CTTCTCCCCA CCAGCCTGCC
 29c GTGGTGCACG AGATCCAGAG ATACATTGAC CTCCTCCCCA CCAACCTGCC
  6b GTGGTGCACG AGATCCAGAG ATACATTGAC CTCCTCCCCA CCAACCTGCC
 11a GTGGTGCACG AGGTCCAGAG ATACATCGAC CTCATCCCCA CCAGCCTGCC
```

*FIG. 2-5.*

```
      1101                                                  1150
 2c   CCATGCAGTG ACCtgTGA.. tTAAaTTCAg AAACTAcCTC AT.CCCAAGG
 2c8  CCATGCAGTG ACCACTGATA CTAAGTTCAG AAACTACCTC ATCCCCAAGG
 25   CCATGCAGTG ACCTGTGACA TTAAATTCAG AAACTATCTC ATTCCCAAGG
 65   CCATGCAGTG ACCTGTGACA TTAAATTCAG AAACTATCTC ATTCCCAAGG
 29c  CCATGCAGTG ACCTGTGATG TTAAATTCAA AAACTACCTC ATCCCCAAGG
 6b   CCATGCAGTG ACCTGTGATG TTAAATTCAA AAACTACCTC ATCCCCAAGG
 11a  CCATGCAGTG ACCTGTGACG TTAAATTCAG AAACTACCTC ATTCCCAAGG 1151                                                  1200
 2c   GCAcaACCAT A.Taac.Tcc CTgACTTCtG TGCTaCATgA ..ACAAAGAA
 2c8  GCACAACCAT AATGGCATTA CTGACTTCCG TGCTACATGA TGACAAAGAA
 25   GCACAACCAT ATTAATTTCC CTGACTTCTG TGCTACATGA CAACAAAGAA
 65   GCACAACCAT ATTAATTTCC CTGACTTCTG TGCTACATGA CAACAAAGAA
 29c  GCACGACCAT AATAACATCC CTGACTTCTG TGCTGCACAA TGACAAAGAA
 6b   GCATGACCAT AATAACATCC CTGACTTCTG TGCTGCACAA TGACAAAGAA
 11a  GCACAACCAT ATTAACTTCC CTCACTTCTG TGCTACATGA CAACAAAGAA 1201                                                  1250
 2c   TTtCCcAAcC CAgAgATgTT TGACCCT.g. CACTTTCTgG AT.A..gTGG
 2c8  TTTCCTAATC CAAATATCTT TGACCCTGGC CACTTTCTAG ATAAGAATGG
 25   TTTCCCAACC CAGAGATGTT TGACCCTCAT CACTTTCTGG ATGAAGGTGG
 65   TTTCCCAACC CAGAGATGTT TGACCCTCAT CACTTTCTGG ATGAAGGTGG
 29c  TTCCCCAACC CAGAGATGTT TGACCCTGGC CACTTTCTGG ATAAGAGTGG
 6b   TTCCCCAACC CAGAGATGTT TGACCCTGGC CACTTTCTGG ATAAGAGTGG
 11a  TTTCCCAACC CAGAGATGTT TGACCCTCGT CACTTTCTGG ATGAAGGTGG 1251                                                  1300
 2c   cAA.TTTAAG AAAAGT.AcT ACTTCATGCC TTTCTCAGCA GGAAAACGgA
 2c8  CAACTTTAAG AAAAGTGACT ACTTCATGCC TTTCTCAGCA GGAAAACGAA
 25   CAATTTTAAG AAAAGTAAAT ACTTCATGCC TTTCTCAGCA GGAAAACGGA
 65   CAATTTTAAG AAAAGTAAAT ACTTCATGCC TTTCTCAGCA GGAAAACGGA
 29c  CAACTTTAAG AAAAGTGACT ACTTCATGCC TTTCTCAGCA GGAAAACGGA
 6b   CAACTTTAAG AAAAGTGACT ACTTCATGCC TTTCTCAGCA GGAAAACGGA
 11a  AAATTTTAAG AAAAGTAACT ACTTCATGCC TTTCTCAGCA GGAAAACGGA 1301                                                  1350
 2c   TtTGTgtgGG AGA>GgcCTg GCCcGCATGG AGCTgTTTTT ATTcCTgACC
 2c8  TTTGTGCAGG AGAAGGACTT GCCCGCATGG AGCTATTTTT ATTTCTAACC
 25   TTTGTGTGGG AGAAGCCCTG GCCGGCATGG AGCTGTTTTT ATTCCTGACC
 65   TTTGTGTGGG AGAAGCCCTG GCCGGCATGG AGCTGTTTTT ATTCCTGACC
 29c  TGTGTATGGG AGAGGGCCTG GCCCGCATGG AGCTGTTTTT ATTCCTGACC
 6b   TGTGTATGGG AGAGGGCCTG GCCCGCATGG AGCTGTTTTT ATTCCTGACC
 11a  TTTGTGTGGG AGAGGGCCTG GCCCGCATGG AGCTGTTTTT ATTCCTGACC
```

*FIG. 2-6.*

```
      1351                                                          1400
 2c   .ccATTTTaC AGAACTTTAA CCTGAAATCT ctggtTGAcc cAAAG.AccT
 2c8  ACAATTTTAC AGAACTTTAA CCTGAAATCT GTTGATGATT TAAAGAACCT
 25   TCCATTTTAC AGAACTTTAA CCTGAAATCT CTGGTTGACC CAAAGAACCT
 65   TCCATTTTAC AGAACTTTAA CCTGAAATCT CTGGTTGACC CAAAGAACCT
 29c  ACCATTTTGC AGAACTTTAA CCTGAAATCT CAGGTTGACC CAAAGGATAT
 6b   ACCATTTTGC AGAACTTTAA CCTGAAATCT CAGGTTGACC CAAAGGATAT
 11a  TTCATTTTAC AGAACTTTAA CCTGAAATCT CTGATTGACC CAAAGGACCT 1401                                                          1450
 2c   tgAcAccACt cCagTTg.CA AtGgatTTGc ttcTgTgCC. CCCTtcTAcC
 2c8  CAATACTACT GCAGTTACCA AAGGGATTGT TTCTCTGCCA CCCTCATACC
 25   TGACACCACT CCAGTTGTCA ATGGTTTTGC CTCTGTGCCG CCCTTCTACC
 65   TGACACCACT CCAGTTGTCA ATGGATTTGC CTCTGTGCCG CCCTTCTACC
 29c  TGACATCACC CCCATTGCCA ATGCATTTGG TDGTGTGCCA CCCTTGTACC
 6b   TGACATCACC CCCATTGCCA ATGCATTTGG TCGTGTGCCA CCCTTGTACC
 11a  TGACACAACT CCTGTTGTCA ATGGATTTGC TTCTGTCCCG CCCTTCTATC 1451             ***                                          1500
 2c   AGcT.TGCTT CAttCCTGTC TGAAGAAggg cAGatggtcT GGCTGCT.cT
 2c8  AGATCTGCTT CATCCCTGTC TGAAGAATGC TAGCCCATCT GGCTGCTGAT
 25   AGCTGTGCTT CATTCCTGTC TGAAGAAGAG CAGATGGCCT GGCTGCTGCT
 65   AGCTGTGCTT CATTCCTGTC TGAAGAAGAG CAGATGGCCT GGCTGCTGCT
 29c  AGCTCTGCTT CATTCCTGTC TGAAGAAGGG CAGATAGTTT GGCTGCTCCT
 6b   AGCTCTGCTT CATTCCTGTC TGAAGAAGGG CAGATAGTTT GGCTGCTCCT
 11a  AGCTGTGCTT CATTCCTGTC TGAAGAAGCA CAGATGGTCT GGCTGCTCCT 1501                                                          1550
 2c   gTGCtgTC.C ......t... ttt..tctgg ggcaatttcC .tctt.cat.
 2c8  CTGCTATCAC CTGCAACTCT TTTTTTATCA AGGACATTCC CACTATTATG
 25   GTGCAGTCCC TGCAGCTCTC TTTCCTCTGG GGCATTATCC ATCTTTCACT
 65   GTGCAGTCCC TGCAGCTCTC TTTCCTCTGG GGCATTATCC ATCTTTCACT
 29c  GTGCTGTCAC CTGCAATTCT CCCTTATCAG GGCCATTAGC CTCTCCCTTC
 6b   GTGCTGTCAC CTGCAATTCT CCCTTATCAG GGCCATTGGC CTCTCCCTTC
 11a  GTGCTGTCCC TGCAGCTCTC TTTCCTCTGG TCCAAATTTC ACTATCTGTG 1551                                                          1600
 2c   ..t.tt..tg c..ttt.Tca tcTg.catct caca.t.c.. cttccctta.
 2c8  TCTTCTCTGA CCTCTCATCA AATCTTCCCA TTCACTCAAT ATCCCATAAG
 25   ATCTGTAATG CCTTTTCTCA CCTGTCATCT CACATTTTCC CTTCCCTGAA
 65   ATCTGTAATG CCTTTTCTCA CCTGTCATCT CACATTTTCC CTTCCCTGAA
 29a  TCTCTGTGAG GGATATTTTC TCTGACTTGT CAATCCACAT CTTCCCATTC
 6b   TCTCTATGAG GGATATTTTC TCTGACTTGT CAATCCACAT CTTCCCATTC
 11a  ATGCTTCTTC TGACCCGTCA TCTCACATTT TCCCTTCCCC CAAGATCTAG
```

FIG. 2-7.

```
        1601                                                        1650
  2c  catc.Ag..a  ccaTt.a...  .caat.tcca  agag.gtg..  ttt.Tt..ct
 2c8  CATCCAAACT  CCATTAAGGA  GAGTTGTTCA  GGTCACTGCA  CAAATATATC
  25  GATCTAGTGA  ACATTCGACC  TTCATTACGG  AGAGTTTCCT  ATGTTTCACT
  65  GATCTAGTGA  ACATTCGACC  TCCATTACTT  AGAGTTTCCT  ATGTTTCACT
 29c  CCTCAAGATC  CAATGAACAT  CCAACCTCCA  TTAAAGAGAG  TTTCTTGGGT
  6b  CCTCAAGATC  CAATGAACAT  CCAACCTCCA  TTAAAGAGAG  TTTCTTGGGT
 11a  TGAACATTCA  GCCTCCATTA  AAAAGTTTC   ACTGTGCAAA  TATATCTGCT 1651                                                        1700
  2c  .tccaccta.  atctatc..t  ....ct.ct.  t.t.t..aT.  actttgattg
 2c8  TGCAATTATT  CATACTCTGT  AACACTTGTA  TTAATTGCTG  CATATGCTAA
  25  GTGCAAATAT  ATCTGCTATT  CTCCATACTC  TGTAACAGTT  GCATTGACTG
  65  GTGCAAATAT  ATCTGCTATT  CTCCATACTC  TGTAACAGTT  GCATTGACTG
 29c  CACTTCCTAA  ATATATCTGC  TATTCTCCAT  ACTCTGTATC  ACTTGTATTG
  6b  CACTTCCTAA  ATATATCTGC  TATTCTCCAT  ACTCTGTATC  ACTTGTATTG
 11a  ATTCCCCATA  CTCTATAATA  GTTACATTGA  GTGCCACATA  ATGCTGATAC 1701                                                        1750
  2c  tcc.cta.tg  aTg.taatt.  tttaatattg  ..ttattg..  A...t.ttAt
 2c8  TACTTTTCTA  ATGCTGACTT  TTTAATATGT  TATCACTGTA  AAACACAGAA
  25  TCACATAATG  CTCATACTTA  TCTAATGTTG  AGTTATTAAT  ATGTTATTAT
  65  TCACATAATG  CTCATACTTA  TCTAATGTTG  AGTTATTAAT  ATGTTATTAT
 29c  ACCACCACAT  ATGCTAATAC  CTATCTACTG  CTGAGTTGTC  AGTATGTTAT
  6b  ACCACCACAT  ATGCTAATAC  CTATCTACTG  CTGAGTTGTC  AGTATGTTAT
 11a  TTGTCTAATG  TTGAGTTATT  AACATATTAT  TATTAAATAG  A 1751                                                        1800
  2c  .A.t.a.aaA  .aaAtgAtaa  tt.t.t..aa  aT...aagtc  A.tgc..tt.
 2c8  AAGTGATTAA  TGAATGATAA  TTTAGTCCAT  TTCTTTTGTG  AATGTGCTAA
  25  TAAATAGAGA  AATATGATTT  GTGTATTATA  ATTCAAAGGC  ATTTCTTTTC
  65  TAAATAGAGA  AATATGATTT  GTGTATTATA  ATTCAAAGGC  ATTTCTTTTC
 29c  CACTAGAAAA  CAAAGAAAAA  TGATTAATAA  ATGACAATTC  AGAGCCAAAA
  6b  CACTATAAAA  CAAAGAAAAA  TGATTAATAA  ATGACAATTC  AGAGCCATTT 1801                                                        1850
  2c  a..at.t.c.  .aaTaaAaag  cattaTtATT  tgctgaaAaa  aaGTCAGTTC
 2c8  ATAAAAAGTG  TTATTAATTG  CTGGTTCA
  25  TGCATGTTCT  AAATAAAAAG  CATTATTATT  TGCTGAAAAA  AA
  65  TGCATGTTCT  AAATAAAAAG  CATTATTATT  TGCTGAAAAA  AA
 29c  AAAAAAAAA
  6b  ATTCTCTGCA  TGCTCTAGAT  AAAAATGATT  ATTATTTACT  GGGTCAGTTC
```

FIG. 2-8.

```
       1851                                                      1900
6b TTAGATTTCT TTCTTTTGAG TAAAATGAAA GTAAGAAATG AAAGAAAATA 1901                                                      1950
6b GAATGTGAAG AGGCTGTGCT GGCCCTCATA GTGTTAAGCA CAAAAAGGGA 1951                                                      2000
6b GAAAGGTAAG AGGGTAGGAA AGCTGTTTTA GCTAAATGCC ACCTAGAGTT 2001                                                      2050
6b ATTGGAGGTC TGAATTTGGA AAAAAAAACT ATGTCCAGGA GAACATTAAG 2101                                                      2150
6b TGTTTGAATT CATGCTCTGC TTTTGTGTTA CTGTAAACAC AAGATCAAGA 2151                                                      2200
6b TTTGGATAAT CTTTTTCCTT TGTGTTTCCA ACTTAGATCA TGTCTAAATA 2201       2216
6b TATGCTTTCA TATGGC
```

FIG. 2-9.

```
1
       Mdp.VvLVLVlc  LSclllLlslW  RQSsgRgkLP  pGPTPLP.IG  NiLQid.KDi  sKSlTN.SKv  YGPVFT.YFG
IIC8   MEPFVVLVLVC  LSFMLLFSLW   RQSCRRRKLP  PGPTPLPIIG  NMLQIDVKDI  CKSFTNFSKV  YGPVFTVYFG
65     MDSLVVLVLVLC LSCLLLLSLW   RQSSGRGKLP  PGPTPLPVIG  NILQIGIKDI  SKSLTNLSKV  YGPVFTLYFG
25     MDSLVVLVLVLC LSCLLLLSLW   RQSSGRGKLP  PGPTPLPVIG  NILQIGIKDI  SKSLTNLSKV  YGPVFTLYFG
29c    MDPAVALVLC   LSCLFLLSLW   RQSSGRGRLP  SGPTPLPIIG  NILQLDVKDM  SYSLTNFSKU  TGPVGTVYFG
6b     MDPAVALVLC   LSCLFLLSLQ   RQSSGRGRLP  SGPTPLPIIG  NILQLDVKDM  SKSLTNFSKV  YGPVFTVYFG
11a    MDPFVVLVLC   LSCLLLLSIQ   RQSSGRGKLP  PGPTPLPVIG  NILQIDIKDV  SYSLTNLSKI  YGPVFTLYFG 71                                                                               140
       lkpiVVlHGY   EaVKEAlIDl   GEEFSGRG.f  Plaeran.G.  GIvfSNGKrW  KEIRREsLmt  LRNFGMGKRS
IIC8   MNPIVVFHGY   EAVKEALIDN   GEEFSGRGNS  PISQRITKGL  GIISSNGKRW  KEIRRFSLTN  LTNFGMGKRS
65     LKPIVVLHGY   EAVKEALIDL   GEEFSGRGIF  PLAERANRGF  GIVFSNGKKW  KEIRRFSLMT  LRNFGMGKRS
25     LKPIVVLHGY   EAVKEALIDL   GEEFSGRGIF  PLAERANRGF  GIVFSNGKKW  KEIRRFSLMT  LRNFGMGKRS
29c    LKPIVVLHGY   EAVKEALIDH   GEEFSGRGSF  PVAEKVNKGL  GILFSNGKRW  KEIRRFCLMT  LRNFGMGKRS
6b     LKPIVVLHGY   EAVKEALIDH   GEEFSGRGSF  PVAEKVNKGL  GILFSNGKRW  KEIRRFCLMT  LRNFGMGKRS
11a    LERMVVLHGY   EVVKEALIDL   GEEFSGRGHF  PLAERANRGF  GIVFSNGKRW  KEIRRFSLMT  LRNFGMGKRS 141                                                                              210
       IEDRVQEEAr   CLVEELRKTk   ASPCDPTFIL  GCAPCNVICS  iiFhkRFDYK  DQqFLnLMek  lNENirIlss
IIC8   IEDRVQEEAH   CLVEELRKTK   ASPCDPTFIL  GCAPCNVICS  VVFQKRFDYK  DQNFLTLMKR  FNENFRILNS
65     IEDRVQEEAR   CLVEELRKTK   ASPCDPTFIL  GCAPCNVICS  IIFHKRFDYK  DQQFLNLMEK  LNENIKILSS
25     IEDRVQEEAR   CLVEELRKTK   ASPCDPTFIL  GCAPCNVICS  IIFHKRFDYK  DQQFLNLMEK  LNENIKILSS
29c    IEDRVQEEAR   CLVEELRKTN   ASPCDPTFIL  GCAPCNVICS  VIFHDRFDYK  DQRFLNLMEK  LNENLRILSS
6b     IEDRVQEEAR   CLVEELRKTN   ASPCDPTFIL  GCAPCNVICS  VIFHDRFDYK  DQRFLNLMEK  FNENLRILSS
11a    IEDRVQEEAR   CLVEELRKTK   ASPCDPTFIL  GCAPCNVICS  IIFQKRFDYK  DQQFLNLMEK  LNENIRIVST
```

FIG. 3-1.

```
       211                                                                              280
IIC8   PWIQiCNNFp .iIDyfPGtH NKllkNvafm kSyilEkvKE HQeSlDmNnp rDFiDCFLiK MEqEkHnQqS
65     PWIQVCNNFP LLIDCFPGTH NKVLKNVALT RSYIREKVKE HQASLDVNNP RDFMDCFLIK MEDEKDNQKS
25     PWIQICNNFS PIIDYFPGTH NKVLKNVAFM KSYILEKVKE HQESMDMNNP QDFIDCFLMK MEKEKHNQPS
29c    PWIQICNNFS PIIDYFPGTH NKLLKNVAFM KSYILEKVKE HQESMDMNNP QDFIDCFLMK MEKEKHNQPS
6b     PWIQVCNNFP ALIDYLPGSH NKIAENFAYI KSYVLERIKE HQESLDMNSA RDFIDCFLIK MEQEKHNQQS
11a    PWIQVCNNFP ALIDYLPGSH NKIAENFAYI KSYVLERIKE HQESLDMNSA RDFIDCFLIK MEQEKHNQQS
       PWIQICNNFP TIIDYFPGTH NKLLKNLAFM ESDILEKVKE HQESMDINNP RDFIDCFLIK MEKEKQNQQN 281                                                                              350
IIC8   EFtiEsLiaT vtDlfgAGTE ttSTTLRYaL LLLLKhPEVT AKVQEEIerV iGRnRSPCMQ DRsHMPYTDA
65     EFNIENLVGT VADLFVAGTE TTSTTLRYGL LLLLKHPEVT AKVQEEIDHV IGRHRSPCMQ DRSHMPYTDA
25     EFTIESLENT AVDLFGAGTE TTSTTLRYAL LLLLKHPEVT AKVQEEIERV IGRNRSPCMQ DRSHMPYTDA
29c    EFTIESLENT AVDLFGAGTE TTSTTLRYAL LLLLKHPEVT AKVQEEIERV IGRNRSPCMQ DRSHMPYTDA
6b     EFTVESLIAT VTDMFGAGTE TTSTTLRYGL LLLLKYPEVT AKVQEEIECV VGRNRSPCMQ DRSHMPYTDA
11a    EFTVESLIAT VTDMFGAGTE TTSTTLRYGL LLLLKYPEVT AKVQEEIECV VGRNRSPCMQ DRSHMPYTDA
       EFTIENLVIT AADLLGAGTE STSTTLRYAL LLLLKHPEVT AKVQEEIERV IGRNRSPCMQ DRGHMPYTDA 351                                                                              420
IIC8   VVHeVQRYiD LlPTslPHAV TcDvKFrNYL IPKGtTIits LTSVLHdnKE FPNPemFDPg HFLDegGNEK
65     VVHEIQRYSD LVPTGVPHAV TTDTKFRNYL IPKGTTIMAL LTSVLHDDKE FPNPNIFDPG HFLDKNGNFK
25     VVHEVQRYLD LLPTSLPHAV TCDIKFRNYL IPKGTTILIS LTSVLHDNKE FPNPEMFDPH HFLDEFFNEK
29c    VVHEVQRYID LLPTSLPHAV TCDIKFRNYL IPKGTTILIS LTSVLHDNKE FPNPEMFDPH HFLDEFFNEK
6b     VVHEVQRYID LLPTNLPHAV TCDVKFKNYL IPKGTTITTS LTSVLHDNKE FPNPEMFDPG HFLDKSGNEK
11a    VVHEIQRUID LLPTNLPHAV TCDVKFKNYL IPKGMTIITS LTSVLHDNKE FPNPEMFDPG HELDKSGNEK
       VVHEVQRYID LIPTSLPHAV TCDVKFRNYL IPKGTTILTS LTSVLHDNKE FPNPEMFDPR HFLDEGGNFK
```

FIG. 3-2.

```
     421                                                                          491
IIC8 KSdYFMPFSA GKRiCvGEgL ArMELFLFLT tILQNFNLKS lvDpKdldtT pvvngfasvP PfYClCFIPV *
65   KSDYFMPFSA GKRICAGEGL ARMELFLFLT TILQNFNLKS VDDLKNLNTT AVTKGIVSLP PSYCICFIPV *
25   KSKYFMPFSA GKRICVGEAL AGMELFLFLT SILQNFNLKS LVDPKNLDTT PVVNGFASVP PFYCLCFIPV *
29c  KSKYFMPFSA GKRICVGEAL AGMELFLFLT SILONFNLKS LVDPKNLDTT PVVNGFASVP PFYCLCFIPV *
6b   KSDYFMPESA GKRMCMGEGL ARMELFLELT TILONENLKS QVDPKDIDIT PIANAFGRVP PLYCLCFIPV *
11a  KSDYFMPESA GKRMCMGEGL ARMELFLFLT TILONFNLKS QVDPKDIDIT PIANAFGRVP PLYCLCFIPV *
     KSNYFMPFSA GKRICVGEGL ARMELFLFLT FILQNFNLKS LIDPKDLDTT PVVNGFASVP PFYCLCEIPC
```

*FIG. 3-3.*

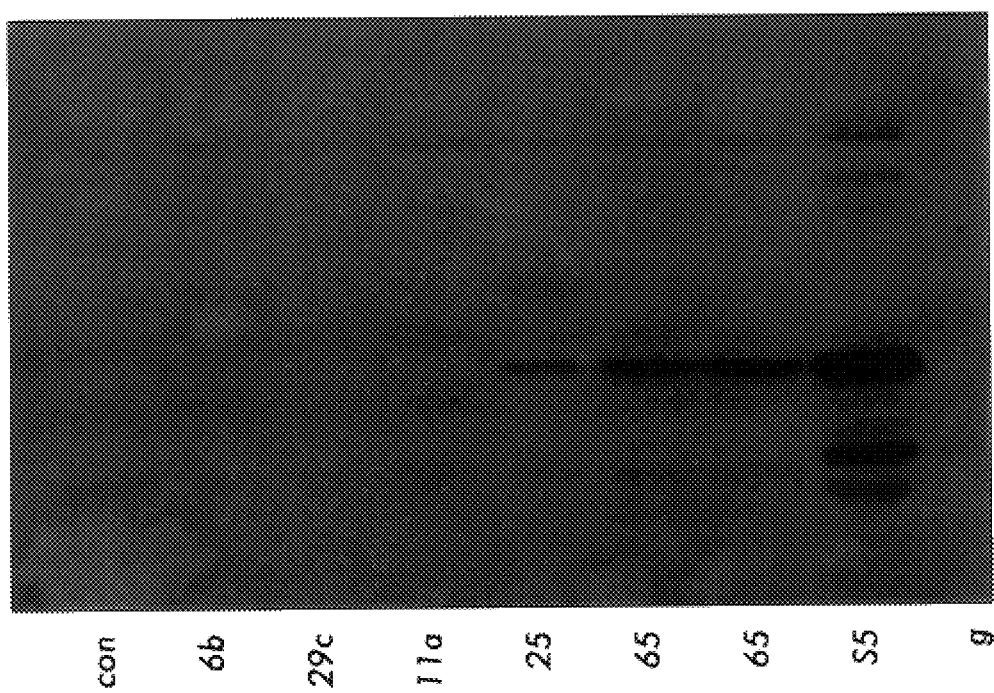
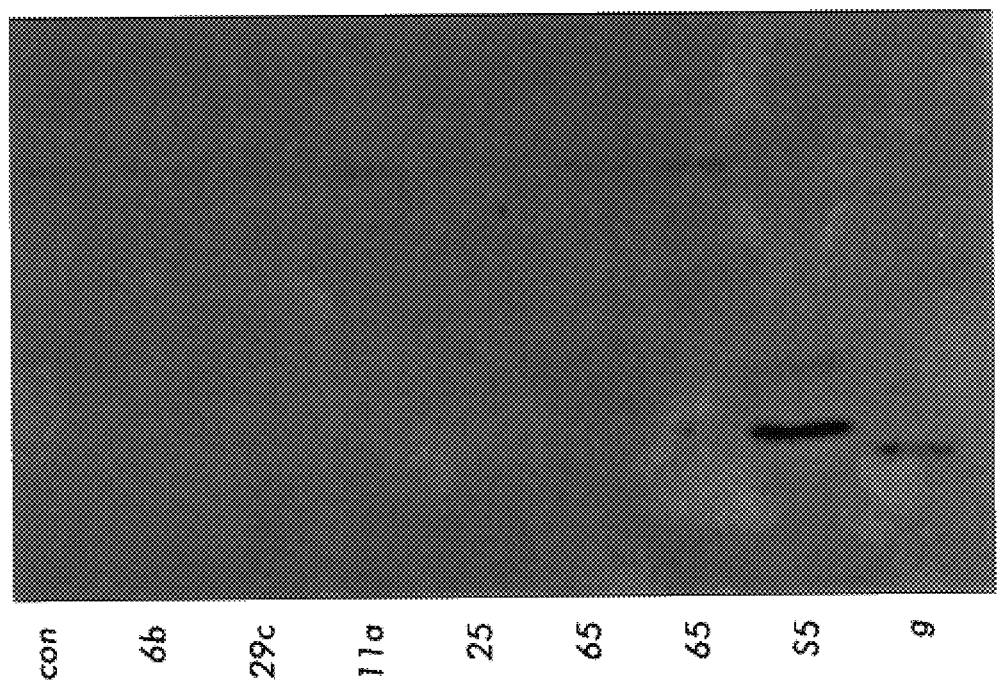
FIG. 4

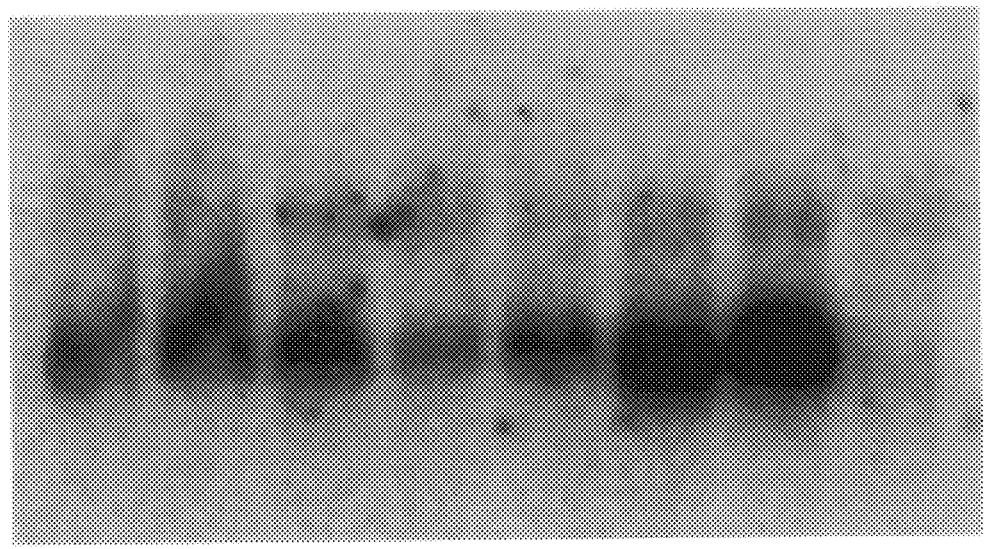
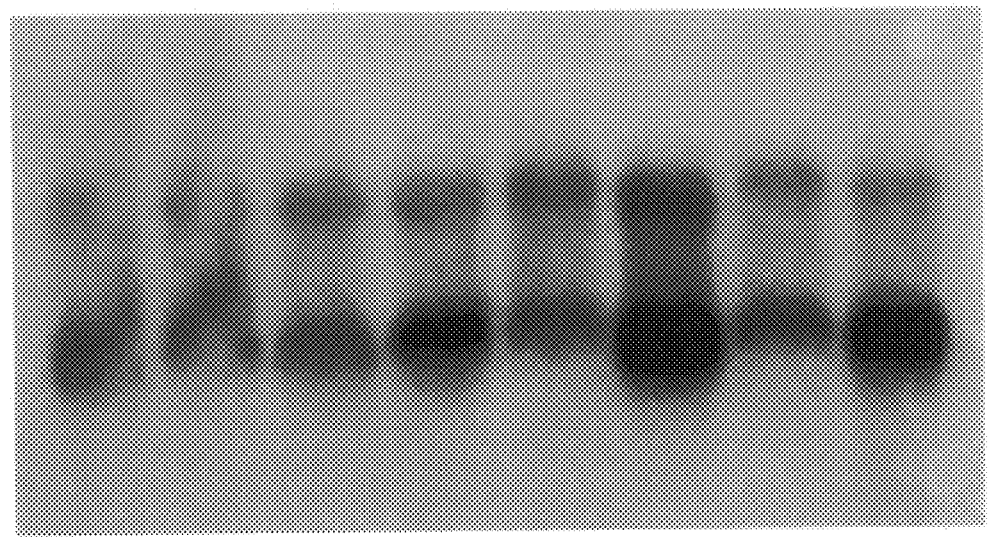
FIG. 5

```
          Exon 4 | Exon 5
      Leu Asn Glu Asn Ile Arg Ile Val Ser Thr Pro Trp Ile Gln | Ile Cys Asn Asn Phe Pro Thr Ile Ile Asp Tyr
600   ATTGAATGAAAACATCAGGATTGTAAGCACCCCCTGGATCCAGATATGCAATAATTTCCCACTATCATTGATTAT
      ||||||||||||||||||||||||||||||||
      ATTGAATGAAAACATCAGGATTGTAAGCACCCCCTGGATCCAG..........

Phe Pro Gly Thr His Asn Lys Leu Leu Lys Asn Leu Ala Phe Met Glu Ser Asp Ile Leu Glu Lys Val Lys Glu
676   TTCCCGGGAACCCATAACAATTACTTAAAAAACCTTGCTTTTATGGAAAGTGATATTTTGGAGAAAGTAAAAGAA
      ||||||||||||||||||||||||||||||||||||||||||||||||||||
      ......GAACCCATAACAATTACTTAAAAAACCTTGCTTTTATGGAAAGTGATATTTTGGAGAAAGTAAAAGAA
             Glu Pro Ile Thr Asn Tyr Leu Lys Thr Leu Leu Trp Lys Val Ile Phe Trp Arg Lys END
                                                                                     *
                                                                                            Exon 5 | Exon 6
      His Gln Glu Ser Met Asp Ile Asn Asn Pro Arg Asp Phe Ile Asp Cys Phe Leu Ile Lys Met Glu Lys | Glu Lys
751   CACCAAGAATCGATGGACATCAACAACCCTCGGGACTTTATTGATTGCTTCCTGATCAAAATGGAGAAGGAAAAG
      ||||||||||||||||||||||||||||||||||||||||||||||||||||||||||||||||||||||||||
      CACCAAGAATCGATGGACATCAACAACCCTCGGGACTTTATTGATTGCTTCCTGATCAAAATGGAGAAGGAAAAG Gln Asn Gln Gln Ser Glu Phe Thr Ile Glu Asn Leu Val Ile Thr Ala Ala Asp Leu
826   CAAAACCAACAGTCTGAATTCACTATTGAAAACTTGGTAATCACTGCAGCTGACTTAC    NORMAL cDNA (2C19wt)
      |||||||||||||||||||||||||||||||||||||||||||||||||||||||||
      CAAAACCAACAGTCTGAATTCACTATTGAAAACTTGGTAATCACTGCAGCTGACTTAC    ABERRANT cDNA (2C19m)
```

FIG. 12.

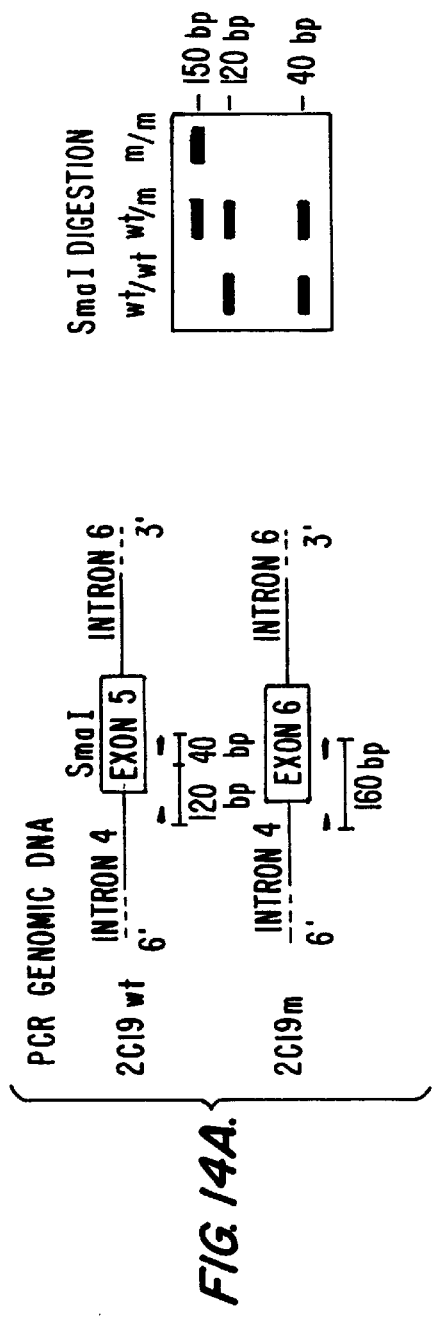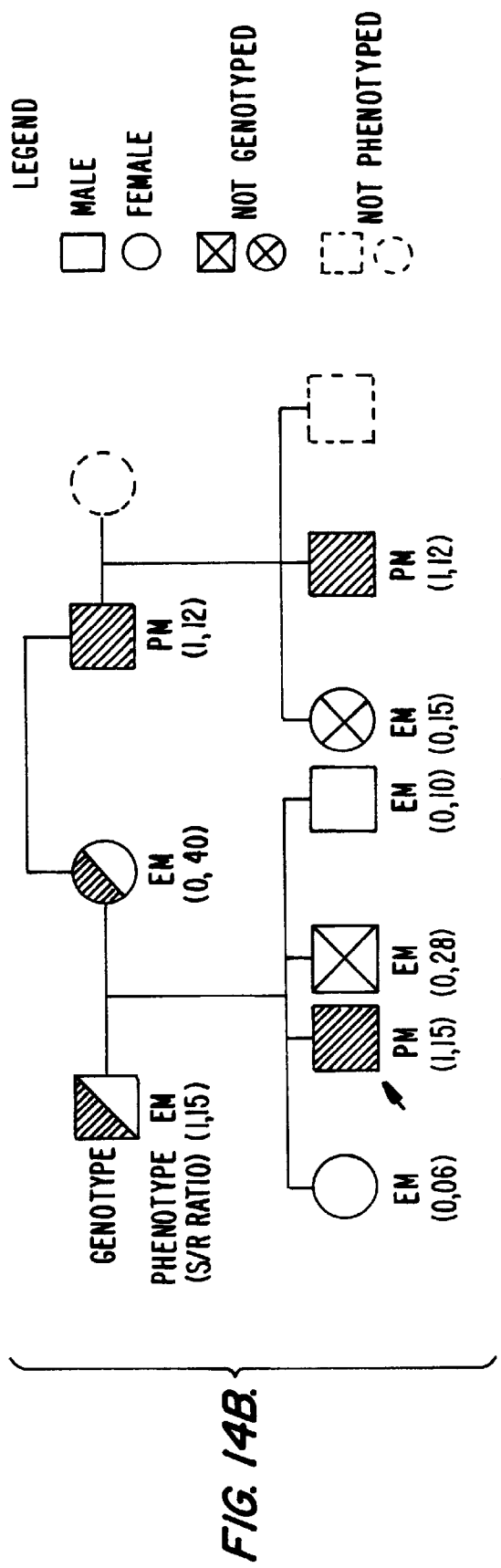
FIG. 14A.
FIG. 14B.

NORMAL (2C19wt)

```
                    SPLICE SITE                               681
------INTRON 4------                    ------EXON 5------    |
tttaatttaataaattattgtttctcttagATATGCAATAATTTCCCACTATCATTGATTATTTCCGGGAACCCATAAC
                    yyyyyyyyyncagG                            Sma I
```

ABERRANT (2C19m)

```
                                          SPLICE SITE        681
------INTRON 4------                      |    ------EXON 5------
tttaatttaataaattattgtttctcttagatatgcaataatttcccactatcattgattattcccagGAACCCATAAC
                          yyyyyyyyyncagG
```

- HOMOZYGOUS (2C19wt/2C19wt) EM
- HETEROZYGOUS (2C19wt/2C19m) EM
- HOMOZYGOUS (2C19m/2C19m) PM $G_{681} \rightarrow A$

FIG. 15C.

NORMAL GENE (2C19wt): EXON 4 (161 bp) — INTRON 4 — SmaI — EXON 5 (177 bp)

ABERRANT GENE (2C19m): EXON 4 (161 bp) — INTRON 4 — EXON 5 (137 bp)

```
ATGGTGATGT AGnAAnTCAT nCCATCTTAT ATTTCnAGAG TGTAGAGGAG

GATTGTTGnG GAAGTAAGAG GnnTAAGATA GAGATGCnTT TATACTATCC

CAAGCAGGGA TrAGTCTAGG AAATGATTaT CGTCttTGAT TCTCTTGTCA

GrAttTTCTT TCTCmnATCT TGtATAATCA GAGaatTACT ACACATGgAC

AATrAarATT TCCCCnTCcA GAtAnACaAt ATATTTATT TATATTTATA

GTTTTAAATT ACAACCAGAG CTTGGCATAT TGTATCTATA CCTTTAATAA
                                    INTRON 4 | EXON 5
ATGCTTTTAA TTTAATAAAT TATTGTTTTC TCTTAGATAT GCAATAATTT
                             A
TCCCACTATC ATTGATTATT TCCCGGGAAC CCATAACAAA TTACTTAAAA
                           |681
ACCTTGCTTT TATGGAAAGT GATATTTGG AGAAAGTAAA AGAACACCAA

GAATCGATGG ACATCAACAA CCCTCGGGAC TTTATTGATT GCTTCCTGAT
              | INTRON 5
CAAAATGGAG AAGGTAAAAT GTTAACAAAA GCTTAGTTAT GTGACTGCTT

GCGTATkTGT GATTCATTGA CTAGTTGkGT GTTTACTACG GATGTTTAAC

AGGTCAAGGA GTAATGCTTG AGAAGCATAT TTAAGTTTTt ATTGTaTGCA

TGAATATCCA GTAAGCATCA TAGAAAATGT AAAATTAAnT TGtTAaATAa

TTAGAaTACA TAGAAGAAAT tGTTtAGATA AATATnATCT ATCTGAACAA

TAAGGATGTC AGGATAGGAA AAGCTCTGTT TCTGCAGCTT CCAGTGGAGA

TCAGCACAGG AGGGAACTTA TTTTTT
```

FIG. 16.

```
agggaaaagacaaataggccggggatgnaaatttagcatgtgagcaacc        wt ttanttaaccagctaggctgtaattgntaattcgagantaatgtnaaagt        wt gatgtgttgattttatgcatgccnnactcnttttgcttttaaggggagt         wt cataggtaagatattacttaaaatttctaaactattattatctgttaact        wt aatatgaagtgttttatatctaatgtttactcatattttaaaattgtttc        wt
      |||||||||||||||||||||||||||||||||||||||||||
      atgaagtgttttatatctaatgtttactcatattttaaaattgtttc      mutant SerProCysAspProThrPheIleLeuGlyCysAlaP
caatcatttagCTTCACCCTGTGATCCCACTTTCATCCTGGGCTGTGCTC        wt
|||||||||||||||||||||||||||||||||||||||||||||||||
caatcatttagCTTCACCCTGTGATCCCACTTTCATCCTGGGCTGTGCTC        mutant
           ^482 roCysAsnValIleCysSerIleIlePheGlnLysArgPheAspTyrLys
CCTGCAATGTGATCTGCTCCATTATTTTCCAGAAACGTTTCGATTATAAA        wt
||||||||||||||||||||||||||||||||||||||||||||||||||
CCTGCAATGTGATCTGCTCCATTATTTTCCAGAAACGTTTCGATTATAAA        mutant AspFlnGlnPheLewAsnLewMetGluLysLeuAsnGluAsnIleArgIl
GATCAGCAATTTCTTAACTTGATGGAAAAATTGAATGAAAACATCAGGAT        wt
||||||||||||||||||||||||||||||||||||||||||||||||||
GATCAGCAATTTCTTAACTTGATGGAAAAATTGAATGAAAACATCAGGAT        mutant eValSerThrProTrpIleGln
TGTAAGCACCCCCTGGATCCAGgtaaggacaagttttgtgcttcctgaga        wt
||||||||||||||| |:|||||||||||||||||||||||||||||||
TGTAAGCACCCCCTGAATCCAGgtaaggacaagttttgtgcttcctgaga        mutant
              End    ^642 aaccacttacagtcttttttctgggaaatccaaaattctatattgacca         wt
|||||||||||||||||||||||||||||||||||||||||||||
aaccacttacagtcttttttctgggaaatccaaaattctatatt              mutant agccctgaagtacatttgtgaatactacagtcttgcctagacagccatggggt     wt gaatatctggaaaagatggcaaagntctttattttatgcacaggaaatgaata     wt tcccaatatagatcaggcttctaagcccattagctccctgatcagtgttt        wt
```

FIG. 17.

CLONING, EXPRESSION AND DIAGNOSIS OF HUMAN CYTOCHROME P450 2C19: THE PRINCIPAL DETERMINANT OF S-MEPHENYTOIN METABOLISM

CROSS-REFERENCE TO RELATED APPLICATION

This application is a continuation-in-part of U.S. Ser. No. 08/201,118, filed Feb. 22, 1994, which is a continuation-in-part of U.S. Ser. No. 07/864,962, filed Apr. 9, 1992, now abandoned, each of which is incorporated by reference in its entirety for all purposes.

TECHNICAL FIELD

The present invention relates generally to isolation and exploitation of a novel member of the cytochrome P450 2C subfamily of enzymes 2C19, which is shown to be the principal human determinant of human S-mephenytoin metabolism. The invention also relates to the isolation and exploitation of an additional member of this family designated 2C18.

BACKGROUND OF THE INVENTION

The cytochromes P450 are a large family of hemoprotein enzymes capable of metabolizing xenobiotics such as drugs, carcinogens and environmental pollutants as well as endobiotics such as steroids, fatty acids and prostaglandins. Some members of the cytochrome P450 family are inducible in both animals and cultured cells, while other forms are constitutive. This group of enzymes has both harmful and beneficial activities. Metabolic conversion of xenobiotics to toxic, mutagenic and carcinogenic forms is a harmful activity. Detoxification of some drugs and other xenobiotic substances is a beneficial activity (Gelboin, *Physiol. Rev.* 60:1107–1). A further beneficial activity is the metabolic processing of some drugs to activated forms that have pharmacological activity.

Genetic polymorphisms of P450 enzymes result in phenotypically-distinct subpopulations that differ in their ability to perform particular drug biotransformation reactions. These phenotypic distinctions have important implications for selection of drugs. For example, a drug that is safe when administered to most human may cause intolerable side-effects in an individual suffering from a defect in a P450 enzyme required for detoxification of the drug. Alternatively, a drug that is effective in most humans may be ineffective in a particular subpopulation because of lack of a P450 enzyme required for conversion of the drug to a metabolically active form. Accordingly, it is important for both drug development and clinical use to screen drugs to determine which P450 enzymes are required for activation and/or detoxification of the drug. It is also important to identify individuals who are deficient in a particular P450 enzyme.

A cytochrome P450 polymorphism of particular concern results in reduced levels of S-mephenytoin 4'-hydroxylase activity in certain subpopulations. (Küpfer et al., *Eur. J. Clin. Pharmacol.* 26:753–759 (1984); Wedlund et al., *Clin. Pharmacol. Ther.* 36:773–780 (1984). Two phenotypes, extensive and poor metabolizers, are present in the human population. Poor metabolizers are detected at low frequencies in Caucasians (2–5%) but at higher frequencies in the Oriental population (~20%) (Nakamura et al., *Clin. Pharmacol. Ther.* 38:402–408 (1985); Jurima et al., *Br. J. Clin. Pharmacol.* 19:483–487 (1985) and blacks (~12%). 4'-hydroxylation of S-mephenytoin is 3–10 fold higher than that of the R- enantiomer in extensive metabolizers, but the ratio is approximately 1 or less in poor metabolizers (Yasumori et al., *Mol. Pharmacol.* 35:443–449 (1990). Rates of S-mephenytoin 4'-hydroxylation in liver microsomes are also much higher than those of R-mephenytoin in extensive metabolizers.

There is some evidence that S-mephenytoin 4' hydroxylase activity resides in the cytochrome P450 2C family of enzymes. A number of 2C human variants (designated 2C8, 2C9 and 2C10) have been partially purified, and/or cloned. See Shimada et al., *J. Biol. Chem.* 261:909–921 (1986); Kawano et al., *J. Biochem.* (Tokyo) 102:493–501 (1987); Gut et al., *Biochem. Biophys, Acta* 884:435–447 (1986); Beaune et al., *Biochem Biophys. Acta* 840:364–370 (1985); Ged et al., *Biochemistry* 27:6929–6940 (1988)); Umbenhauer et al., *Biochemistry* 26, 1094–1099 (1987); Kimura et al., *Nucleic Acids Res.* 15:10053–10054 (1987); Shephard et al., *Ann. Humn. Gentc.* 53:23–31 (1989); Yasumori et al., *J. Biochem.* 102:1075–1082 (1987); Relling et al., *J. Pharmacol. Ther.* 252:442–447. A comparison of the P450 2C cDNAs and their predicted amino acid sequences shows that about 70% of the amino acids are absolutely conserved among the human P450 2C subfamily. Some regions of human P450 2C protein sequences have particularly highly conservation, and these regions may participate in common P450 functions. Other regions show greater sequence divergence regions and are likely responsible for different substrate specificities between 2C members.

There has been considerable controversy as to whether any of the known 2C members encodes the principal human determinant of S-mephenytoin 4' hydroxylase activity, in which the polymorphism discussed above presumably resides. The multiplicity and common properties of cytochromes P450 make it difficult to separate their different forms, especially the minor forms. Even in situations where P450 cytochromes have been isolated in purified form by conventional enzyme purification procedures, they have been removed from the natural biological membrane association and therefore require the addition of NADPH-cytochrome P450 reductase and other cell fractions for enzymatic activity.

The known members of the cytochrome P450 2C family exhibit only low-levels of S-mephenytoin 4'-hydroxylase activity, if any. Moreover, such low levels of activity are not specific for the S-enantiomer. For example f when the cDNA isolated by Kimura et al. (1987), supra, was expressed in HepG2 cells, it metabolized racemic and (R)-mephenytoin but had no (S)-mephenytoin hydroxylase activity, suggesting that the polymorphism in the metabolism of (S)-mephenytoin resides in a different member of the P450 family. As a further example, Yasumori et al. (1991), supra, reported that an allelic variant of 2C9 ($Arg^{144}Tyr^{358}Iso^{359}Gly^{417}$) showed a low-level of catalytic activity toward S-mephenytoin in a cDNA-directed yeast expression. However, Srivastava et al., *Mol. Pharmacol.* 40:69–69 (1991) expressed an identical cDNA in yeast and a $Arg^{144}Cys^{358}Iso^{359}Asp^{417}$ variant (2C10 by present nomenclature) but were unable to demonstrate catalytic activity of 2C9 or 2C10 toward S-mephenytoin. Relling et al., *J. Pharmacol. Exper. Ther.* 252:442–447 (1990), were also unable to demonstrate catalytic activity of an allelic variant of $Cys^{144}Tyr^{358}Ile^{359}Gly^{417}$-2C9 toward S-mephenytoin using a retroviral cDNA expression system in HepG2 cells. In contrast, all of these 2C9 variants metabolized tolbutamide in the various expression systems confirming that failure to observe S-mephenytoin 4'-hydroxylase activity was not due to deficiencies in the expression system.

Based on the foregoing, it is apparent that a need exists to identify and isolate the P450 2C family member representing the principal determinant of S-mephenytoin 4'-hydroxylase activity in humans. There is also a need for stable cell lines expressing the S-mephenytoin 4'-hydroxylase activity. A need is also apparent for methods of screening drugs for safety and efficacy in individuals deficient in S-mephenytoin 4'-hydroxylase activity. There is also a need for methods for diagnosing individuals deficient in S-mephenytoin 4'-hydroxylase activity. The present invention fulfills these and other needs.

SUMMARY OF THE INVENTION

The invention provides purified cytochrome P450 2C19 polypeptides. The amino acid sequence of an exemplary P450 2C19 polypeptide is designated SEQ. ID. No. 1. Other cytochrome P450 2C19 polypeptides usually comprises an amino acid sequence having at least 97% sequence identity with the exemplified sequence. Many of the 2C19 polypeptides of the invention exhibit stereospecific S-mephenytoin 4'-hydroxylase activity. The activity is typically at least about 1 nmol mephenytoin per nmol of the purified polypeptide per minute.

The invention also provides purified cytochrome P450 2C18 polypeptides. The amino acid sequences of exemplary 2C18 polypeptides are designated SEQ. ID. Nos. 5 and 11.

In another aspect of the invention, purified DNA segments encoding the P450 2C19 polypeptides described above are provided. Some DNA segments encode the exemplary P450 2C19 having the amino acid sequenced designated SEQ. ID. No. 1. One such exemplary DNA segment is designated SEQ. ID. No. 2. Other DNA segments encode the P450 2C18 polypeptides described above. Exemplary DNA segments are designated SEQ. ID. Nos. 6 and 12.

In a further aspect of the invention stable cell lines are provided. The cell lines comprise an exogenous DNA segment encoding a cytochrome P450 2C19 polypeptide having at least 97% sequence identity with the amino acid sequence designated SEQ. ID. No. 1. The DNA segment is capable of being expressed in the cell line. Cell lines preferably produce high levels of the P450 2C19 polypeptide such as 10–200 pmol of the polypeptide per mg of total microsomal protein. Preferred cell lines are eukaryotic, including yeast and insect cells.

The invention also provides methods of producing a cytochrome P450 2C19 polypeptide. In these methods, a stable cell line, as described above, is cultured under conditions such that the DNA segment contained in the cell line is expressed.

The invention also provides antibodies that specifically bind to a 2C19 polypeptide comprising the amino acid sequence designated SEQ. ID. No. 1. Preferred antibodies are incapable of binding to nonallelic forms of 2C polypeptides, such as 2C9.

In another aspect, the invention provides methods of screening for a drug that is metabolized by S-mephenytoin 4'-hydroxylase activity. The drug is contacted with a cytochrome P450 2C19 polypeptide. A metabolic product resulting from an interaction between the polypeptide is detected. The presence of the product indicates that the drug is metabolized by the S-mephenytoin 4'-hydroxylase activity. The cytochrome P450 2C19 used in the methods may be substantially pure or may be a component of a lysate of a stable cell line. The cytochrome P450 2C19 polypeptide may also be a component of an intact stable cell line. Some methods further comprise the steps of contacting the drug with a liver extract comprising a mixture of cytochrome P450 polypeptides, and detecting a metabolic product resulting from an interaction between the drug and the mixture of cytochrome P450 polypeptides.

The invention also provides methods of identifying a mutagenic, carcinogenic or cytotoxic compound. In some methods, the compound is contacted with a stable cell line capable of expressing a 2C19 polypeptide, such as described above. Mutagenic, carcinogenic or cytotoxic effects of the compound on the cell line are assayed. In other methods, the compound is contacted with a cytochrome P450 2C19 polypeptide in a reaction mixture. A metabolic product is generated resulting from S-mephenytoin 4'-hydroxylase activity on the compound. The metabolic product is assayed for mutagenic, carcinogenic or cytotoxic effects on a test cell line. The effects indicate that the compound is mutagenic, carcinogenic or cytotoxic. In some methods, the test cell line is added to the reaction mixture before, during or after the contacting step. The 2C19 polypeptide used in these methods can be substantially pure or a component of a lysate of a stable cell line. The 2C19 polypeptide can also be a component of an intact stable cell line. *Salmonella typhimurium* is a preferred cell line.

The invention also provides methods for testing the chemopreventive activity of an agent. A stable cell line capable of expressing a 2C19 polypeptide, such as described above, is contacted with an agent suspected of being chemopreventive in the presence of a carcinogen. The agent can be contacted with the cell line before addition of the carcinogen. Effects of the agent on the cell line that are indicative of chemopreventive activity are monitored.

The invention also provides methods for determining the metabolites activated by a carcinogenic or xenobiotic. A stable cell line capable of expressing a 2C19 polypeptide, such as described above, is contacted with the suspected carcinogen or xenobiotic. Metabolites and/or their effects are identified.

The invention also provides methods of detecting a cytochrome 2C19 polypeptide in a tissue sample. The tissue sample is contacted with an antibody that specifically binds to the 2C19 polypeptide preferably without specifically binding to nonallelic variants such as 2C9. Specific binding between the antibody and the polypeptide is detected to indicate the presence of the polypeptide.

In another aspect of the invention, methods of diagnosing a patient having a deficiency in S-mephenytoin 4'-hydroxylase activity are provided. In these methods, a sample of nucleic acids is obtained from the patient, and a cytochrome P450 2C19 DNA sequence from the nucleic acids in the sample is analyzed for the presence of a polymorphism indicative of the deficiency. The most frequently occurring polymorphisms in the P450 2C19 genes occur at nucleotides 681 and 636 of the 2C19 gene.

In some methods, the P450 2C19 DNA sequence subject to analysis is genomic. In such methods, an amplifying step is often primed from a forward primer sufficiently complementary with a first subsequence of the antisense strand of the 2C19 sequence to hybridize therewith, and a reverse primer sufficiently complementary to a second subsequence of the sense strand of the 2C19 sequence to hybridize therewith.

Some methods detect a polymorphism at nucleotide 681 of the coding region of the P450 2C19 DNA genomic sequence. This can be achieved by selecting a forward primer that hybridizes upstream from nucleotide 681 of the coding region, and a reverse primer that hybridizes downstream from nucleotide 681 of the coding region. Amplification products generated from these primers can be analyzed by digesting the amplified DNA segment with a restriction enzymes that recognizes a site that includes nucleotide 681 of the coding region.

Other methods detect a polymorphism at nucleotide 636 of the coding region of the P450 2C19 DNA genomic sequence. This can be achieved using a forward primer that hybridizes upstream from nucleotide 636 of the coding region, and a reverse primer that hybridizes downstream of nucleotide 636 of the coding region. Amplification products are conveniently analyzed by digestion with an enzyme that recognizes a site that includes nucleotide 636 of the coding region.

Other methods detect the 681 polymorphism by a different approach involving selective amplification of the wildtype or mutant allele. For example, for selective amplification of the wildtype allele, a suitable forward primer has about 10–50 contiguous nucleotides from the wildtype 2C19 sequence shown in FIG. 16 including the nucleotide at position 681 of the coding region. The forward primer primes amplification from the complement of the wildtype 2C19 sequence without priming amplification from the complement of the mutant 2C19 sequence shown in FIG. 16. Preferably, the 3' nucleotide of the forward primer is the nucleotide at position 681. Analogously, the 681 mutant allele can be amplified using a forward primer having about 10–50 contiguous nucleotides from the mutant 2C19 sequence shown in FIG. 16 including the nucleotide at position 681 of the coding sequence. The forward primer primes amplification from the complement of the mutant 2C19 sequence without priming amplification from the complement of the wildtype 2C19 sequence shown in FIG. 16.

The invention also provides analogous methods for detection of the 636 polymorphism.

In other methods, the segment of 2C19 DNA subject to analysis is a cDNA sequence. cDNA is produced by reverse transcribing mRNA in the sample to produce the cDNA sequence. In some methods for detecting the 681 polymorphism, the forward primer comprises about 10–50 contiguous nucleotides upstream of nucleotide 643 of the coding region of the wildtype 2C19 cDNA sequence shown in FIG. 12 and hybridizes to the complement of the 2C19 sequence upstream from nucleotide 643 of the coding region, and the reverse primer comprises about 10–50 contiguous nucleotides from the complement of the wildtype 2C19 cDNA sequence shown in FIG. 12 and hybridizes to the 2C19 sequence downstream from nucleotide 682 of the coding region. In other methods, the forward primer hybridizes to the complement of the wildtype 2C19 cDNA sequence shown in FIG. 12 between nucleotides 643 and 682 without hybridizing to the complement of the mutant 2C19 cDNA sequence shown in FIG. 12. In other methods, the reverse primer hybridizes to the wildtype 2C19 cDNA sequence shown in FIG. 12 between nucleotides 643 and 682 without hybridizing to the mutant 2C19 cDNA sequence shown in FIG. 12.

The invention provides analogous methods for diagnosing the 636 polymorphism from cDNA. In some methods, the forward primer comprises about 10–50 contiguous nucleotides upstream of nucleotide 636 of the coding region of the wildtype 2C19 cDNA sequence shown in FIG. 12, and the reverse primer comprises about 10–50 contiguous nucleotides from the complement of the wildtype 2C19 cDNA sequence shown in FIG. 12 downstream from nucleotide 636 of the coding region.

The invention also provides methods capable of detecting any polymorphism from cDNA. In these methods, the full-length 2C19 cDNA sequence is usually amplified. Analysis is often performed by sequencing a segment of the 2C19 cDNA amplification product.

The invention provides further methods for diagnosing polymorphisms in genomic DNA. In these methods, genomic DNA is digested with a restriction enzyme that recognizes a site that includes nucleotide 636 or 681 of the coding region. The digestion products are then detected by Southern blotting with a labelled segment of the 2C19 DNA sequence as a probe.

In another aspect of the invention, diagnostic kits are provided. Some diagnostic kits comprise forward and reverse primers. The forward primer is sufficiently complementary with a first subsequence of the antisense strand of a double-stranded 2C19 genomic DNA sequence to hybridize therewith, and the reverse primer sufficiently complementary with a second subsequence of the sense strand of the 2C19 genomic sequence to hybridize therewith. For example, in some methods for diagnosis of the 681 polymorphism, the first subsequence is upstream of nucleotide 681 of the coding region, and second subsequence is downstream of nucleotide 681 of the coding region. Similarly, in some methods for diagnosis of the 636 polymorphism, the first subsequence is upstream of nucleotide 636 of the coding region, and the second subsequence is downstream of nucleotide 636 of the coding region.

BRIEF DESCRIPTION OF THE DRAWINGS

FIG. 3 depicts a comparison of amino acid sequences of cytochrome P450 2C8 allelic variants.

FIG. 4 depicts a Western blot of recombinant transformed COS-1 cells. Each lane represents microsomal protein (50 µg) from an independent transformation with the indicated P450 2C cDNA, mock-transfected cells (CON), 20 µg of human liver microsomal protein (liver S5), or 2 pmol of pure P450g (2C13).

FIG. 5 shows a Northern blot of human mRNAs. Each lane represents 10 μg of mRNA, and the blot was probed with end-labeled T300R, an oligoprobe specified for 2C8 (SEQ. ID. No. 8) (top), stripped, and reprobed with $^{32}$P-actin cDNA (bottom).

FIG. 12 Sequence alignment of PCR products from normal and aberrantly spliced CYP2C19 cDNAS (SEQ. ID Nos. 45 and 47), with the corresponding amino acid translations (SEQ. ID Nos. 46 and 48) indicated above and below the nucleotide sequence. The new termination codon TAA in the aberrant cDNA is indicated by the word END and the asterisk. The PCR primers are indicated by the horizontal arrows in the sequence. The aberrant CYP2C19 cDNA is missing 40 base pairs of the cDNA in poor metabolizers as indicated by the dotted line.

FIG. 15(A–C) A. Partial sequence of the intron 4/exon 5 junction of CYP2C19 in extensive and poor metabolizers (SEQ. ID. Nos. 49 and 50) Intron sequences are shown in lower case and exon sequences in capitals. The nucleotides deleted in the aberrantly spliced cDNA are indicated in bold. The polymorphic SmaI site is underlined in 2C19(wt). The highly conserved AG residues at the intron/exon junction are shown in black boxes. The consensus sequence (11YNCAGG) (Y=pyrimidine, R=purine, N=any base) for the 3'-splice site is indicated underneath the normal and cryptic splice junctions. The branch point consensus sequence (CURAY) is placed underneath two putative branch points. B. Sequencing of PCR products of genomic DNA from three individuals who were homozygous normal, heterozygous, and homozygous defective (based on their SmaI restriction digests). The polymorphic SmaI restriction site is indicated by the bracket in the homozygous wt sequence. The G→A base pair change corresponding to position 681 of the cDNA is also indicated. C. Schematic representation of splicing in CYP2C19$_{wt}$ and in CYP$^2$C19$_m$. The black box indicates the 40 bp that are deleted in exon 5 of poor metabolizers.

FIG. 16 Additional 2C19 genomic sequence flanking the 681 polymorphism. The wildtype (SEQ. ID. No. 51) and mutant (SEQ ID No. 61) sequences are identical except for the G/A transposition at nucleotide 681. Regions of sequence ambiguity are indicated in lower case (n=any nucleotide, k=G/T ambiguity, r=A/G ambiguity, m=A/C ambiguity).

FIG. 17 Genomic DNA sequence flanking the 636 polymorphism (also referred to as m2). Wildtype and mutant sequences are designated SEQ. ID. Nos. 52 and 54 respectively. Intron sequences are indicated in lower case and exons in capital. Translated amino acids (SEQ. ID. No. 53) are indicated above the nucleotide sequence. The numbers underneath the sequences indicate the first (482) and last (642) nucleotides in exon 4. The two mutations found in exon 4 are indicated in bold. The aberrant stop codon is indicated by the word "End." Exemplary primers for PCR amplification are underlined.

DEFINITIONS

Figure 6:
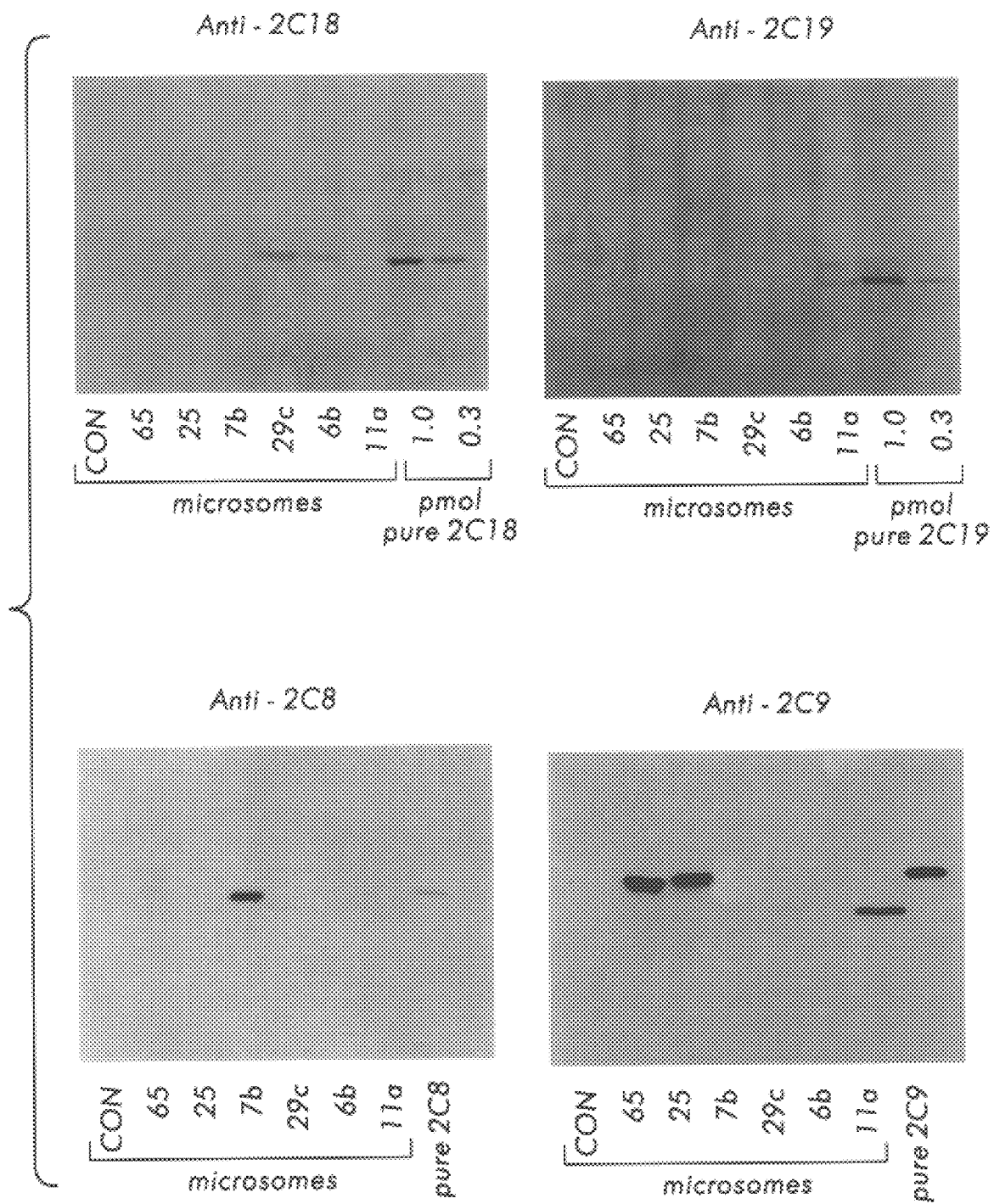
FIG. 6 Western blots of yeast microsomes expressing recombinant P450 2C cDNAs. CON=control (yeast microsomes lacking recombinant proteins).

Abbreviations for the twenty naturally occurring amino acids follow conventional usage (*Immunology—A Synthesis* (E. S. Golub & D. R. Gren, eds., Sinauer Associates, Sunderland, Mass., 2nd ed., 1991) (hereby incorporated by reference for all purposes). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present M invention. Examples of unconventional amino acids include: 4-hydroxyproline, γ-carboxyglutamate, ε-N, N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand that are 5' to the 5' end of the RNA transcript are referred to as "upstream sequences"; sequence regions on the DNA strand that are 3' to the 3' end of the RNA transcript are referred to as "downstream sequences".

The phrase "polynucleotide sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence shown in SEQ. ID. No. 2 or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci.* (USA) 85:2444 (1988), by computerized implementations of these algorithms (FASTDB (Intelligenetics), BLAST (National Center for Biomedical Information) or GAP, BESTFIT, FASTA, and TFASTA (Wisconsin Genetics Software Package Release 7.0, Genetics Computer Group, 575 Science Dr., Madison, Wis.)), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" (also sometimes referred to as "percentage homology") is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 96 percent sequence identity, more usually at least 97, 98 or 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequence of SEQ. ID. Nos. 2, 6 or 12.

As applied to polypeptides, the term "substantial identity" (or "substantial homology") means that two peptide sequences, when optimally aligned, such as by the programs BLAZE (Intelligenetics) GAP or BESTFIT using default gap weights, share at least 85% sequence identity preferably at least 96 percent sequence identity, more preferably at least 97, 98 or 99 percent sequence identity or more (e.g., 99.5 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

Specific binding exists when the dissociation constant for a dimeric complex is $\leq 1\,\mu M$, preferably $\leq 100$ nM and most preferably $\leq 1$ nM.

The term "allelic variants" refers to gene sequences mapping to the same chromosomal location in different individual in a species but showing a small degree of sequence divergence from each other. Typically, allelic variants encode polypeptides exhibiting at least 96% or 97% amino acid sequence identity with each other.

The term "nonallelic variants" refers to gene sequences that show similar structural and/or functional properties but map at different chromosomal locations in an individual. In the 2C family, nonallelic variants typically exhibit 70–96% amino acid sequence identity with each other.

The term "cognate variants" refers to gene sequences that are evolutionarily and functionally related between humans and other species such as primates, porcines, bovines and rodents such as mice and rats. Thus, the cognate primate gene to a human 2C19 gene is the primate gene which encodes an expressed protein which has the greatest degree of sequence identity to the 2C19 protein and which exhibits an expression pattern similar to that of the 2C19 protein.

Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

A polymorphism is a condition in which two or more different nucleotide sequences coexist in the same interbreeding population in a DNA sequence.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetrahedron Lett.* 22:1859–1862 (1981); and the solid support method of U.S. Pat. No. 4,458,066.

A primer is an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature.

"Probe" refers to an oligonucleotide which binds through complementary base pairing to a subsequence of a target nucleic acid. Probes will typically hybridize to target sequences lacking complete complementarity with the probe sequence on reducing the stringency of the hybridization conditions. The probes are preferably directly labelled as with isotopes or indirectly labelled such as with biotin to which a streptavidin complex may later bind. By assaying for the presence or absence of the probe, one can detect the presence or absence of the target.

"Subsequence" refers to a sequence of nucleic acids that comprise a part of a longer sequence of nucleic acids.

The term "target region" refers to a region of a nucleic acid to be analyzed such as a polymorphic region.

Hybridization refers to binding between an oligonucleotide and a target sequence via complementary base pairing to achieve the desired priming by PCR polymerases or detection of hybridization signal, and sometimes embraces minor mismatches that can be accommodated by reducing the stringency of the hybridization conditions.

DESCRIPTION OF THE SPECIFIC EMBODIMENTS

The invention provides novel cytochrome P450 2C polypeptides, DNA fragments encoding these polypeptides and cell lines expressing the polypeptides. The invention also provides methods of using the novel polypeptides for, inter alia, identifying drugs metabolized by S-mephenytoin 4'-hydroxylase activity.

I. Polypeptides

In one embodiment, the invention provides novel cytochrome P450 2C polypeptides, designated 2C18 and 2C19. The 2C18 and 2C19 proteins are nonallelic with each other and with known 2C polypeptides. An exemplary 2C19 polypeptide has the amino acid sequence designated SEQ. ID. No. 1. The invention also provides allelic variants of the exemplified 2C19 polypeptide, and natural and induced mutants of such variants. The invention provides human 2C19 polypeptides and cognate variants thereof. Typically, 2C19 variants exhibit at substantial sequence identity (e.g., at least 96% or 97% amino acid sequence identity) with the exemplified 2C19 polypeptide and cross-react with antibodies specific to this polypeptide. 2C19 variants are usually encoded by nucleic acids that show substantial sequence identity (e.g., at least 96% or 97% sequence identity) with the nucleic acid encoding the exemplified 2C19 variant (SEQ. ID. No. 2).

Some 2C19 polypeptides, including the exemplified polypeptide, exhibit high levels of stereospecific S-mephenytoin 4'-hydroxylase activity. See Table IV. Indeed, it is highly probable that 2C19 represents the principal human determinant of this activity. Typically such 2C19 polypeptides exhibit a stereospecific S-mephenytoin 4'-hydroxylase activity of about 0.5–100, 1–10 or about 4–6 nmol S-mephenytoin per nmol 2C19 polypeptide per minute. Frequently, the activity of 2C19 polypeptides is higher than of native human liver microsomes. The activity of such polypeptides for the R-enantiomer of mephenytoin is typically at least 10, 50 or 100-fold lower.

Other 2C19 polypeptides may lack substantial stereospecific S-mephenytoin 4'-hydroxylase activity. Such polypeptides represent allelic variants of the exemplified 2C19 polypeptide. These polypeptides sometimes exhibit low levels of mephenytoin 4'-hydroxylase activity (i.e., less than about 0.5 or 0.2 nmol mephenytoin per nmol 2C19 polypeptide per minute). This activity may, or may not be, stereospecific. Although the presence of a 2C19 polypeptide with low enzymic activity could account for the phenotype of a few individuals defective in S-mephenytoin 4'-hydroxylase activity, the phenotype in most such individuals results from a complete or substantial absence of 2C19 polypeptide. See, e.g., FIG. 10.

The invention also provides 2C18 polypeptides. The amino acid sequences of two allelic variants of 2C18 are designated SEQ. ID. Nos. 5 and 11. Also provided are allelic variants of the exemplified 2C18 polypeptides, conjugated variants thereof, and natural and induced mutants of any of these. Typically, 2C18 variants exhibit substantial sequence identity (e.g., at least 96% or 97% amino acid sequence identity) with the exemplified 2C18 polypeptides and cross-react with antibodies specific to these polypeptides. 2C18 variants are usually encoded by nucleic acids that show substantial sequence identity (e.g., at least 96% or 97% sequence identity) with the nucleic acid encoding the exemplified 2C18 variants (SEQ. ID. Nos. 6 and 12).

2C18 polypeptides typically show low levels of mephenytoin 4'-hydroxylase activity (0.01–0.2 nmol mephenytoin per nmol 2C18 polypeptide per min. For some 2C18 polypeptides, the activity shows a small degree of stereoselectivity (up to about five fold). However, by contrast to the 2C19 polypeptides, such stereoselectivity as is shown by 2C18 polypeptides is in favor of the R enantiomer. Some variants of 2C18 show high levels of a distinct enzymic activity, namely, tolbutamide hydroxylase activity (e.g., about 50–200 pmol tolbutamide per nmol 2C18 polypeptide per min). Conceivably, some variants of 2C18 exhibit novel enzymic or regulatory functions not shared by other 2C family members.

Besides substantially full-length polypeptides, the present invention provides fragments of full-length 2C18 and 2C19 polypeptides. Some such fragments share the enzymic activity of a full-length fragment. A segment of a full-length 2C18 or 2C19 polypeptide will ordinarily comprise at least 50 contiguous amino acids and more usually, 100, 200 or 400 contiguous amino acids from one of the exemplified polypeptide sequences, designated SEQ. ID. Nos. 1, 5 and 11. Fragments of full-length 2C18 and 2C19 polypeptides are often terminated at one or both of their ends near (i.e., within about 5, 10 or 20 aa of) the boundaries of functional or structural domains. Fragments are useful for, inter alia, generating antibodies specific to a 2C19 or 2C18 polypeptide. Fragments consisting essentially of the hypervariable regions of these polypeptides are preferred immunoglobulins for generating antibodies specific to a particular allelic variant.

II. Nucleic Acid Fragments

In another aspect of the invention, nucleic acids fragments are provided. An exemplified cDNA sequence of a 2C19 polypeptide is designated SEQ. ID. No. 2. Exemplified cDNA sequences encoding two variant 2C18 polypeptides are designated SEQ. ID. Nos. 6 and 12. The exemplified sequences include both translated regions and 3' and 5' flanking regions. The exemplified sequence data can be used to design probes for other DNA fragments encoding 2C18 or 2C19 polypeptides (or fragments thereof). These DNA fragments include human genomic clones, cDNAs and genomic clones from other species, allelic variants, and natural and induced mutants of any of these. Specifically, all nucleic acid fragments encoding all 2C18 and 2C19 polypeptides disclosed in this application are provided. Genomic libraries of many species are commercially available (e.g., Clontech, Palo Alto, Calif.), or can be isolated de novo by conventional procedures. cDNA libraries are best prepared from liver extracts.

The probes used for isolating clones typically comprise a sequence of about at least 15, 20 or 25 contiguous nucleotides (or their complement) of an exemplified DNA sequence (i.e., SEQ. ID. Nos. 2, 6 or 12). Preferably probes are selected from regions of the exemplified sequences that show a high degree of variation between different 2C nonallelic variants. Hypervariable regions are the nucleic acids encoding amino acids 181–210, 220–248, 283–296 and 461–479. Probes from these regions are likely to hybridize to allelic variants but not to nonallelic variants of the exemplified sequences under stringent conditions. Allelic variants can be isolated by hybridization screening of plaque lifts (Benton & Davis, Science 196:180 (1978). Alternatively, cDNAs can be prepared from liver mRNA by polymerase chain reaction (PCR) methods. 5'- and 3'- specific primers for 2C19 are designed based on the nucleotide sequence designated SEQ. ID. No. 2. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19:4967 (1991); Eckert et al., PCR Methods and Applications 1:17 (1991); PCR (eds. McPherson et al., IRL Press, Oxford); and U.S. Pat. No. 4,683,202 (each of which is incorporated by reference for all purposes).

Nucleotide substitutions, deletions, and additions can be incorporated into the polynucleotides of the invention. Nucleotide sequence variation may result from degeneracy of the genetic code, from sequence polymorphisms of 2C18 and 2C19 alleles, minor sequencing errors, or may be introduced by random mutagenesis of the encoding nucleic acids using irradiation or exposure to EMS, or by changes engineered by site-specific mutagenesis or other techniques. See Sambrook et al., Molecular Cloning: A Laboratory Manual (C.S.H.P. Press, NY 2d ed., 1989) (incorporated by reference for all purposes).

III. Cell Lines

In another embodiment of the invention, cell lines capable of expressing the nucleic acid segments described above are provided. Stable cell lines are preferred to cell lines conferring transient expression. Stable cell lines can be passaged at least fifty times without reduction in the level of 2C polypeptides expressed by the cell lines. Preferably, cell lines are capable of being cultured so as to express 2C polypeptides at high levels, usually at least 0.2, 1, 10, 20, 50, 100, 200 or 500 pmol of 2C polypeptide per mg of microsomal protein. For example, the 2C19 expression level of many cell lines of the invention is typically about 0.2–10, 000, 1–200, 7–100, 10–50 or 10–20 pmol 2C19 polypeptide per mg microsomal protein. An expression level of 10 pmol 2C19 per mg microsomal protein means that 2C19 represents about 0.06% of total cellular protein. For E. coli and insect cell lines, the recombinant P450 protein can comprise 5–10% of total cellular protein. Often, the stable cell lines of the invention express more than one P450 polypeptide. These cell lines express 2C18 and/or 2C19 together with other members of the 2C family, or other P450 cytochromes such as 1A1, 1A2, 2A6, 3A3, 3A4, 2B6, 2B7, 2C9, 2D6, and/or 2E1.

E. coli is one prokaryotic host useful for cloning the polynucleotides of the present invention. Other microbial hosts suitable for use include bacilli, such as *Bacillus subtilus*, and other enterobacteriaceae, such as Salmonella, Serratia, and various Pseudomonas species. Expression vectors typically contain expression control sequences compatible with the host cell, e.g., an origin of replication, any of a variety of well-known promoters, such as the lactose promoter system, a tryptophan (trp) promoter system, a beta-lactamase promoter system, or a promoter system from phage lambda. Vectors often also contain an operator sequence and/or a ribosome binding site. The control sequences are operably linked to a P450 DNA segment so as to ensure its expression.and control the expression thereof.

Other microbes, such as fungi, particularly, yeast, are particularly useful for expression. Saccharomyces is a preferred host, with suitable vectors having expression control sequences, such as promoters, including 3-phosphoglycerate kinase or other glycolytic enzymes, and an origin of replication, termination sequences and the like as desired. For example, the plasmid pAAH5 can be used. The 5'-noncoding sequence of the P450 2C cDNAs can be eliminated and six adenosines added by polymerase chain reaction (PCR) amplification to optimize expression in yeast cells. The 5'-and 3'-primers recommended for amplification of 2C18 are 5'-GCAAGCTTAAAAAATGGATCCAGCT GTGGCTCT-3' (SEQ. ID. No. 15) and 5'-GCAAGCTT GCCAAACTATCTGCCCTTCT-3' (SEQ. ID. No. 16). This includes addition of a Hind III restriction site at both ends to allow insertion into the pAAH5 vector and six 6 adenosines at the 5'-end to optimize translation. The final 20 bases of each sequence is specific for 20 bases at the 5'-end of 2C18 starting with the ATG for methionine and 20 bases of the 3'-noncoding region. The primers for 2C19 can be constructed similarly. The yeast strain used, *Saccharomyces cerevisiae* 334, can be propagated non-selectively in YPD medium (1% yeast extract, 2% peptone, 2% dextrose (Hovland et al. (1989) Gene 83, 57–64) and Leu+ transformants selected on synthetic minimal medium containing 0.67% nitrogen base (without amino acids), 0.5% ammonium sulfate, 2% dextrose and 20 $\mu$g/ml L histidine (SD+ His). Plates are made by the addition of 2% agar. Yeast can be transformed by the lithium acetate method of Ito et al. (1983) *J. Bacteriol.* 153, 163 and selected on SD+His for selection of transformants. Cells are then grown to mid-logarithmic phase (Oeda et al., *DNA* 4:203–210 (1985)) and microsomes containing recombinant protein can be prepared.

Insect cells (e.g., SF9) with appropriate vectors, usually derived from baculovirus, are also suitable for expressing 2C polypeptides. See Luckow, et al. *Bio/Technology* 6:47–55 (1988) (incorporated by reference for all purposes).

Mammalian tissue cell culture can also be used to express and produce the polypeptides of the present invention (see Winnacker, From *Genes to Clones* (VCH Publishers, N.Y., N.Y., 1987). Suitable host cell lines include CHO cell lines (e.g., V79) (Dogram et al. (1990) *Mol. Pharmacol.* 37, 607–613), various COS cell lines, HeLa cells, myeloma cell lines and Jurkat cells, hepatoma cell lines (Hep G2), and a lymphoblastoid cell line AHH-1 TK+/−. Crespi et al. (1991) *Carcinogenesis* 12, 355–359. Expression vectors for these cells (e.g., pEBVHistK or pSV2) can include expression control sequences, such as an origin of replication, a promoter (e.g., a HSV tk promoter or pgk (phosphoglycerate kinase promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Preferred expression control sequences are promoters derived from immunoglobulin genes, SV40, adenovirus, bovine papillomavirus, and the like. Expression control sequences are operably linked to a DNA segment encoding a P450 polypeptide so as to ensure the polypeptide is expressed.

The vectors containing the polynucleotide sequences of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See generally Sambrook et al., *Molecular Cloning: A Laboratory Manual* (Cold Spring Harbor Press, 2nd ed., 1989) (incorporated by reference in its entirety for all purposes).

Once expressed, the polypeptides of the invention and their fragments can, if desired, be purified according to standard procedures of the art, including ammonium sulfate precipitation, affinity columns, column chromatography, gel electrophoresis and the like (see generally Scopes, *Protein Purification* (Springer-Verlag, N.Y., 1982).

IV. Antibodies

The invention also provides antibodies that specifically bind to epitopes on the 2C18 and 2C19 polypeptides of the invention. Some antibodies specifically bind to one member of the 2C family (e.g., 2C19) without binding to nonallelic forms. Some antibodies specifically bind to a single allelic form of a 2C member such as the 2C19 polypeptide having the amino acid sequence designated SEQ. ID. No. 1. Antibodies that specifically bind to a 2C19 polypeptide without binding to a 2C9 polypeptide are particularly useful in view of the relatively high degree of sequence identity between these nonallelic variants. See Table II. The production of non-human monoclonal antibodies, e.g., murine, lagomorpha, equine is well known and can be accomplished by, for example, immunizing an animal with a preparation containing a 2C19 polypeptide or an immunogenic fragment thereof. Human antibodies can be prepared using phage-display technology. See, e.g., Dower et al., WO 91/17271 and McCafferty et al., WO 92/01047 (each of which is incorporated by reference in its entirety for all purposes). Humanized antibodies are prepared as described by Queen et al., WO 90/07861.

V. Methods of Use

A. Identification of Drugs Unsuitable for Administration to Poor Metabolizers of S-Mephenytoin The identification of a 2C19 polypeptide as the principal determinant of human S-mephenytoin 4'-hydroxylase activity facilitates methods of screening drugs that are metabolized by this enzyme. Such drugs likely lack efficacy and/or show intolerable side effects in individuals having a defect in S-mephenytoin 4'-hydroxylase activity (low producers). The substantial absence of this activity in low producers often results in an inability to detoxify such drugs, preventing their elimination from the body. Substantial absence of S-mephenytoin 4'-hydroxylase activity can also prevent metabolic processing of certain drugs to activated forms. Drugs suspected of being metabolized by S-mephenytoin 4'-hydroxylase activity include, in addition to mephenytoin itself, omeprazole, proguanil, diazepam and certain barbiturates.

Drugs are screened for metabolic processing by S-mephenytoin 4'-hydroxylase activity in a variety of assays. See Example 5. In brief, the drug under test is usually labelled with a radioisotope or otherwise. The drug is then contacted with a 2C19 polypeptide exhibiting S-mephenytoin 4'-hydroxylase activity (e.g., the polypeptide designated SEQ. ID. No. 1). The 2C19 polypeptide can be in purified form or can be a component of a lysate of one of the cell lines discussed in Section III. Often, the 2C19 polypeptide is part of a microsomal fraction of a cell lysate. The 2C19 polypeptide can also be a component of an intact cell as many drugs are taken up by such cells. Often, the reaction mixture is supplemented with one or more of the following reagents: dilauroylphosphatidylcholine, cytochrome P450 reductase, human cytochrome b5, and NADPH. (See Example 5, for concentrations of these reagents and a suitable buffer). After an incubation period (e.g., 30 min), the reaction is terminated, and centrifuged. The supernatant is analyzed for metabolic activity, e.g., by a spectrographic or chromatographic method. The assay is usually performed in parallel on a control reaction mixture without a 2C19 polypeptide. Metabolic activity is shown by a comparative analysis of supernatants from the test and control reaction mixtures. For example, a shift in retention time of radiolabelled peaks between test and control under HPLC analysis indicates that the drug under test is metabolized by S-mephenytoin 4'-hydroxylase activity. Often, the test is repeated using an extract from human liver in place of the 2C19 polypeptide. The appearance of a labelled metabolic peak from the reaction using 2C19 recombinant organisms or 2C19 recombinant cell fractions having the same HPLC retention time, and a specific activity at least as high, as that observed for human liver microsomes provides strong evidence that S-mephenytoin 4-hydroxylase activity plays a major role in processing the drug. The test can also be repeated using other 2C members, such as 2C18, as controls, in place of 2C19.

Drugs can also be screened for metabolic dependence on S-mephenytoin 4'-hydroxylase activity in transgenic nonhuman animals. Some such animals have genomes comprising a 2C19 transgene (e.g., SEQ. ID. No. 2) operably linked to control sequences so as to render the transgene capable of being expressed in the animals. Other transgenic animals have a genome containing homozygous null mutations of endogenous 2C19 genes. Mice and other rodents are particular suitable for production of transgenic animals. Drugs are administered to transgenic animals in comparison with normal control animals and the effects from administration are monitored. Drugs eliciting different responses in the transgenic animals than the control animals likely require S-mephenytoin 4'-hydroxylase activity for detoxification and/or activation.

Drugs identified by the above screening methods as being metabolized by S-mephenytoin 4'-hydroxylase activity should generally not be administered to individuals known to be deficient in this enzyme, or should be administered at different dosages. Indeed, in the absence of data on an individual patient's S-mephenytoin 4-hydroxylase phenotype, it is often undesirable to administer such drugs to any member of an ethnic group known to be at high risk for S-mephenytoin 4-hydroxylase deficiency (e.g., Orientals and possibly blacks). If it is essential to administer drugs identified by the above screening procedures to individuals known to be at risk of enzymic deficiency (e.g., no alternative drug is available), a treating physician is at least apprised of a need for vigilant monitoring of the patient's response to the drug. In general, the identification of a new drug as a substrate for 2C19 would mitigate against further development of the drug.

B. Screening Compounds for Mutagenic Cytotoxic or Carcinogenic Activity

The invention provides methods of measuring the mutagenic, cytotoxic or carcinogenic potential of a compound. In some methods, mutagenic, cytotoxic or carcinogenic effects are assayed directly on a cell line harboring one or more recombinant cytochrome P450 enzymes. In these methods, a compound under test is added to the growth medium of a cell line expressing 2C19, and/or 2C18 and/or other cytochrome P450s. Often, one or more of the reagents discussed in Section V(I), supra, is also added. After a suitable incubation, mutagenic, cytotoxic or carcinogenic effects are assayed. Mutagenic effects are assayed, e.g., by detection of the appearance of drug-resistant mutant cell colonies (Thompson, *Methods Enzymol.*, 58:308, 1979). For example, mutagenicity can be evaluated at the hgprt locus (Penman et al., (1987) *Environ. Mol. Mutagenesis* 10, 35–60). Cytotoxicity can be assayed from viability of the cell line harboring the P450 enzyme(s). Carcinogenicity can be assessed by determining whether the cell line harboring the P450 enzymes has acquired anchorage-independent growth or the capacity to induce tumors in athymic nude mice.

In other methods, a suspected compound is assayed in a selected test cell line rather than a cell line harboring P450 enzymes. In these methods, the compound under test is contacted with P450 2C19 and/or 2C18 and/or other P450 enzymes. The P450 enzyme(s) can be provided in purified form, or as components of lysates or microsomal fractions of cells harboring the recombinant enzyme(s). The P450 enzyme(s) can also be provided as components of intact cells. Usually, one or more of the reagents discussed in Section V(1), supra, is also added. optionally, the appearance of metabolic products from the suspected compound can be monitored by techniques such as thin layer chromatography or high performance liquid chromatography and the like.

The metabolic products resulting from treatment of the suspected compound with P450 enzyme(s) are assayed for mutagenic, cytotoxic or carcinogenic activity in a test cell line. The test cell line can be present during the metabolic activation of the mutagen or can be added after activation has occurred. Suitable test cell lines include a mutant strain of *Salmonella typhimurium* bacteria having auxotrophic histidine mutations (Ames et al., *Mut. Res.* 31:347–364 (1975). Other standard test cell lines include chinese hamster ovary cells (Galloway et al., *Environ. Mutagen.* 7:1 (1985); Gulati et al., (*Environ. Mol. Mutagenesis* 13:133–193 (1989)) for analysis of chromosome aberration and sister chromatic exchange induction, and mouse lymphoma cell (Myhr et al., *Prog. Mut. Res.* 5:555–568, (1985)).

The use of defined P450 enzymes for activation of compounds in the present methods offers significant advantages over previous methods in which rat or human S9-supernatant liver fractions (containing an assortment of P450 enzymes) were used. The present methods are more reproducible and also provide information on the mechanisms by which mutagenesis, cytotoxicity and carcinogenicity are effected.

C. Identification of Potential Chemopreventive Drugs

The invention also provides methods for identifying drugs having chemopreventive activity. These methods employ similar procedures to those discussed in paragraph (2) above except that the methods are performed using a known mutagenic, cytotoxic or carcinogenic agent, together with a suspected chemopreventive agent. Mutagenic, cytotoxic or carcinogenic effects in the presence of the chemopreventive agents are compared with those in control experiments in which the chemopreventive agent is omitted.

D. Screening for Potential Chemotherapeutic Drugs

The invention provides analogous methods to those described in paragraph (2), supra, for screening chemotherapeutic agents. In some methods, chemotherapeutic activity is determined directly on a tumorigenic cell line expressing 2C19 and/or 2C18 and or other cytochrome P450 enzymes. In other methods, chemotherapeutic activity is determined on a tumorigenic test cell line. Chemotherapeutic activity is evidenced by reversion of the transformed phenotype of cells resulting in reduced 50bb agar growth or reduced tumor formation in nude mice.

E. Programmed Cell Death

The invention provides analogous methods to those described in paragraph (2), supra, for identifying agents that induce programmed cell death or apoptosis. Apoptosis may have an important impact on prevention of malignant transformation. Programmed cell death is assayed by DNA fragmentation or cell-surface antigen analysis.

F. Monitoring 2C18 and 2C19 Polypeptides

The invention provides methods of quantitating the amount of the specific protein in mammalian tissues by measuring the complex formed between the antibody and proteins in the tissue. For example, a biological sample is contacted with an antibody under conditions such that the antibody binds to specific proteins forming an antibody:protein complex which can be quantitatively detected.

VI. Diagnosing 2C19 and 2C18 Polymorphisms
Diagnostic Assays for Identifying Individuals
Deficient in S-Mephenytoin 4'-Hydroxylase The invention provides a variety of assays for identifying individuals deficient in S-mephenytoin 4'-hydroxylase activity. Such individuals comprise about 3–5% of Caucasian populations and about 20% of Orientals and possibly blacks. Identification of individuals deficient in S-mephenytoin 4'-hydroxylase activity is important in selecting appropriate drugs for treatment of these individuals. Usually, drugs that are metabolized by S-mephenytoin 4'-hydroxylase should not be administered to these individuals. The assays diagnose mutations in cDNA or genomic DNA encoding 2C19, which as discussed above, is the principal human determinant of S-mephenytoin 4'-hydroxylase activity. The cDNA assays are particularly useful for de novo localization of a 2C19 mutation to a particular nucleotide or nucleotides. The genomic assays are particularly useful for large-scale screening of individuals for the presence of a mutation that has previously been localized.

A. Amplification Technologies

Many of the diagnostic assays rely on amplification of part or all of a DNA segment encoding a 2C19 polypeptide (e.g., a 2C19 gene). In a preferred embodiment, target segments encoding a 2C19 polypeptide are amplified by the polymerase chain reaction. The PCR process is described in e.g., U.S. Pat. Nos. 4,683,195; 4,683,202; and 4,965,188; PCR Technology: *Principles and Applications for DNA Amplification* (ed. Erlich, Freeman Press, New York, N.Y., 1992); *PCR Protocols: A Guide to Methods and Applications* (eds. Innis et al., Academic Press, San Diego, Calif. (1990); Mattila et al. *Nucleic Acids Res.* 19:4967 (1991); Eckert & Kunkel *PCR Methods and Applications* 1:17 (1991); PCR (eds. McPherson et al., IRL Press, Oxford) (each of which is incorporated by reference in its entirety for all purposes). Reagents, apparatus and instructions for using the same are commercially available (e.g., from PECI). Other amplification systems include, ligase chain reaction, QB RNA replicase and RAN-transcription-based amplification systems.

To amplify a target nucleic acid sequence in a sample by PCR, the sequence must be accessible to the components of the amplification system. Accessibility can be achieved by isolating the nucleic acids from the sample. A variety of techniques for extracting nucleic acids from biological samples are known in the art. Alternatively, if the sample is fairly readily disruptable, the nucleic acid need not be purified prior to amplification by the PCR technique, i.e., if the sample is comprises cells, particularly peripheral blood lymphocytes or monocytes, lysis and dispersion of the intracellular components may be accomplished merely by suspending the cells in hypotonic buffer. See Han et al. *Biochemistry* 26:1617–1625 (1987).

For amplification of mRNA sequences, a first step is the synthesis of a DNA copy (cDNA) of the region to be amplified by reverse transcription. Reverse transcription is the polymerization of deoxynucleoside triphosphates to form primer extension products that are complementary to a ribonucleic acid template. The process is effected by reverse transcriptase, an enzyme that initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are avian myeloblastosis virus reverse transcriptase and *Thermus thermophilous* DNA polymerase, a thermostable DNA polymerase with reverse transcriptase activity marketed by PECI. Reverse transcription can be carried out as a separate step, or in a homogeneous reverse transcription-polymerase chain reaction (RT-PCR). Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilous* (Tth) DNA polymerase, a thermostable DNA polymerase with reverse transcriptase activity marketed by PECI.

The first step of each amplification cycle of the PCR involves the separation of the nucleic acid duplex formed by the primer extension. Strand separation is achieved by heating the reaction to a sufficiently high temperature for an sufficient time to cause the denaturation of the duplex but not to cause an irreversible denaturation of the polymerase (see U.S. Pat. No. 4,965,188). Typical heat denaturation involves temperatures ranging from about 80° C. to 105° C. for times ranging from seconds to minutes. Typically, any initial RNA template is also degraded during the denaturation step leaving only DNA template. Other means of strand separation, including physical, chemical, or enzymatic means, are also possible.

Once the strands are separated, the next step involves hybridizing the separated strands with primers that flank the target sequence. The primers are then extended to form complementary copies of the target strands. Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering system. Suitable polymerizing agents include, for example, *E. coli* DNA polymerase I or its Klenow fragment, $T_4$ DNA polymerase, Tth polymerase, and Taq polymerase, a heat-stable DNA polymerase isolated from *Thermus aquaticus* commercially available from Perkin-Elmer Cetus Instruments (PECI, Norwalk, Conn.). See U.S. Pat. No. 4,889,818. See Gelfand, 1989 in *PCR Technology*, supra. The polymerizing agents initiate synthesis at the 3'-end of the primer and proceeds toward the 5'-end of the template until synthesis terminates.

The primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

The primers are selected to be substantially complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer with the remainder of the primer sequence being complementary to the strand. Alternatively, complementary bases or longer sequences can be interspersed into the primer, provided that the primer sequence has sufficient complementarity with the sequence of the strand to be amplified to hybridize therewith and thereby form a template for synthesis of the extension product of the other primer.

Paired primers for amplification of a given segment of DNA are designated forward and reverse primers. Conventionally, the orientation of a double-stranded DNA molecules is that of the sense (or coding strand), with the 5'-terminus of the coding strand being drawn on the left (see, e.g., FIG. 15). Under this convention, the forward primer hybridizes to a double-stranded DNA molecule at a position 5' (or upstream) from the reverse primer. The forward primer hybridizes to the complement of the coding strand of the double stranded sequence (i.e., the antisense strand) and the reverse primer hybridizes to the coding strand.

The appropriate length of a primer depends on the intended use of the primer but typically ranges from 10–100, 15–50, 15–30, or more usually, 15 to 25 nucleotides. Shorter primers tend to lack specificity for a target nucleic acid sequence and generally require cooler temperatures to form sufficiently stable hybrid complexes with the template. Longer primers are expensive to produce and can sometime self-hybridize to form hairpin structures.

The spacing of primers determines the length of segment to be amplified. The spacing is not usually critical and amplified segments can range in size from about 25 bp to at least 35 kbp. Segment from 25–2000, 50–1000, 100–500 bp or about 400 bp are typical. For larger segments, difficulties may occasionally be encountered in obtaining efficient and accurate amplification. For smaller segments, analysis of amplification products may be more difficult.

The primer can be labelled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

B. Tissue Sample for Analysis

The diagnostic assays are performed on a tissue sample containing a nucleic acid encoding a 2C19 polypeptide. For assay of genomic DNA, virtually any tissue sample (other than pure red blood cells) is suitable. For example, convenient tissue samples include whole blood, buccal, skin and hair. For assay of cDNA, the tissue sample must be obtained from an organ in which a 2C19 gene is expressed, such as the liver. Liver samples from dead patients are suitable for de novo localization of mutations (see Section C, infra). However, for screening of living persons, liver biopsies, while feasible, are generally undesirable. Thus, for large-scale screening of living persons, analysis of genomic DNA is preferred.

C. De Novo Localization of 2C19 Polymorphisms

2C19 polymorphisms are identified and localized to specific nucleotides by comparison of nucleic acids from poor metabolizing individuals with nucleic acids from extensive metabolizers. The comparison can be initiated directly at the genomic level. If intron primers are known, individual exons and intron/exon junctions of 2C19 can be amplified from genomic DNA. These fragments can be sequenced directly or analyzed by single-stranded conformational analysis to indicate the presence of a polymorphism and then analyzed by sequencing.

Comparison is sometimes initiated at the cDNA level because of the shorter size of cDNA (about 1750 bp) relative to genomic DNA (about 55 kbp). cDNA is amplified from liver samples of individuals known to have phenotypic S-mephenytoin metabolic deficiencies, and the cDNA sequence is compared with the wildtype sequence shown in SEQ. ID. No. 2. Often, the full-length cDNA is amplified. An initial comparison can be performed by single-stranded conformational analysis to indicate the existence of a polymorphism. The polymorphism is then localized by sequence analysis indicating the site of mutations in cDNA. Of course, the amplification product can also be sequenced directly without prior conformational analysis. Having localized a mutation in cDNA, a corresponding region of genomic 2C19 DNA is amplified. The genomic DNA is usually amplified from primers spanning the mutation. At least one of the primers for this amplification usually comprises a subsequence of the cDNA sequence proximate (i.e., within 25–200 bp of the cDNA mutation). Primers can also comprise subsequences of genomic 2C19 DNA that have already been sequenced, subsequences from related genomic sequences, such as 2C18 or 2C9 (see de Morais et al., Biochem. Biophys. Res. Commun. 194:194–201 (1993)) (incorporated by reference in its entirety for all purposes), or can be random. An amplified genomic fragment spanning the portion of the coding region in which the cDNA polymorphism occurs is sequenced and compared with the corresponding region from a 2C19 sequence from an individual exhibiting extensive S-mephenytoin 4'-hydroxylase metabolism to identify the locus of the genomic mutation.

In some instances, there will be a simple relationship between genomic and cDNA mutations. That is, a single base change in a coding region of genomic DNA can give rise to a corresponding mutated codon in the cDNA. In other instances, the relationship between genomic and cDNA mutations is more complex. Thus, for example, a single base change in genomic DNA creating an aberrant splice site can give rise to deletion of a substantial segment of cDNA in a poor metabolizing individual.

D. The 681 and 636 Polymorphisms

The principal mutation in individuals deficient in the S-mephenytoin 4'-hydroxylase activity is designated the 681 polymorphism. See Example 7. The 681 polymorphism results from a single-base mutation in genomic 2C19 DNA at nucleotide position 681 of the coding region. A nucleotide in a coding (i.e., exonic) region of genomic 2C19 DNA is designated the same number as the corresponding nucleotide in the cDNA sequence shown in SEQ. ID. No. 2, when the genomic coding sequence is maximally aligned with the cDNA sequence. The 681 polymorphism results in a G/A transposition at nucleotide 681 of the coding region.

Homozygous mutations at this position occur in about 70% of individuals having a low-producing (i.e., defective) S-mephenytoin 4'-hydroxylase phenotype. The mutation is inherited in an autosomal recessive fashion. Thus, individuals heterozygous in this mutation usually exhibit normal (i.e., extensive S-mephenytoin activity). Fortuitously, the mutation confers two distinct properties that facilitate its identification. In genomic DNA, the polymorphism results in loss of several restriction enzyme sites (e.g., SmaI) and acquisition of other restriction sites (e.g., EcoRII) site in mutant individuals compared with wildtype individuals. These restriction sites include the 681 nucleotide. In mRNA or cDNA, the 681 mutation results in a deletion of 40 bp spanning nucleotides 643–682 of the wildtype cDNA sequence shown in FIG. 12. The deletion is the consequence of an altered splice pattern stemming from the presence of the 681 polymorphism in genomic DNA.

A second polymorphism is designated the 636 polymorphism. See Example 8. The 636 polymorphism results from a single-base mutation in genomic 2C19 DNA at nucleotide position 636. The 636 polymorphism results in a G/A transposition thereby introducing a premature stop codon into 2C19 mRNA. The mutation is easily be recognized by the loss of e.g., a BamHI site in both genomic and cDNA and acquisition of e.g., a HinfI site. The mutation is inherited in an autosomal recessive fashion. Homozygous mutations at nucleotide 636 account for about 10% of low-producing phenotypes in Orientals. Heterozygous individuals having one allele defective in the 636 polymorphism and the other allele defective in the 681 polymorphism account for all or nearly all of the remaining 15% of low producing Oriental individuals. Thus, the 681 and 636 polymorphisms collectively account for all, or nearly all, low producing phenotypes in Orientals.

In Caucasians, the 636 polymorphism is less prevalent and some low producing individuals probably have a mutation at a locus other than nucleotide 681 or 636 of the coding sequence. Conceivably, a few mutations might occur in other genes that exert regulatory control over the 2C19 gene. However, most, if not all, of the remaining mutations probably result from additional polymorphisms in the 2C19 gene.

E. Screening Assays for Defined Mutations

The invention provides assays that permit large-scale screening of individuals for the presence of defined mutations. Of course, detection of the 681 and 636 mutations, which account for all or nearly all deficiencies in Orientals and about 75% of deficiencies in Caucasians, is of primary importance. An assay on an individual under test is often performed in parallel with control assays on DNA samples from subjects of known phenotype (i.e., extensive or poor metabolizer of S-mephenytoin).

1. Genomic Assays

Assays are preferably performed on a genomic substrate because of the ready availability of tissue samples containing genomic DNA.

a. Amplification of Segments Spanning a Defined Mutation

A preferred strategy for analysis entails amplification of a DNA sequence spanning previously localized polymorphism(s) (e.g., the 681 and/or 636 polymorphisms). Amplification of such a sequence can be primed from forward and reverse primers that hybridize to a 2C19 gene on opposite sides of a mutation (e.g., the 681 mutation, but which do not hybridize to the mutated nucleotide itself). That is, for detection of the 681 polymorphism, the forward primer hybridizes upstream or 5' to the 681 nucleotide and the reverse primer hybridizes downstream or 3' to this nucleotide. Similarly, for detection of the 636 polymorphism, the forward primer hybridizes upstream or 5' to the 636 nucleotide and the reverse primer hybridizes downstream or 3' to this nucleotide. For simultaneous analysis of 636 and 681 polymorphisms, the forward primer hybridizes upstream or 5' to the 636 nucleotide and the reverse primer hybridizes downstream or 3' to nucleotide 681.

The forward primer is sufficiently complementary to the antisense strand of a 2C19 DNA sequence to hybridize therewith and the reverse primer is sufficiently complementary to the sense strand of the 2C19 sequence to hybridize therewith. The primers usually comprise first and second subsequences from opposite strands of a double-stranded 2C19 DNA sequence. Isolated points of mismatch between a primer and a corresponding 2C19 subsequence can usually be tolerated but are not preferred. It is particularly important to avoid mismatches in the two nucleotides at the 3' end of the primer (especially the terminal nucleotide).

Because allelic variants of 2C19 exhibit at least about 97% sequence identity to each other, it is not critical which variant is selected as a source of subsequences for incorporation into forward and reverse primers. For example, suitable subsequences can be obtained from the genomic 2C19 sequence defined as wildtype in FIGS. 15–17. FIG. 15 provides genomic sequence immediately flanking the 681 mutation, and FIG. 16 provides more distal flanking sequences. FIG. 17 provides genomic sequence flanking the 636 mutation. These figures provide sufficient sequence for selection of a multitude of paired primers for amplification of a sequence spanning the 681 and/or 636 polymorphisms. Although there is no apparent advantage for doing so, additional genomic sequence flanking the regions already sequenced could easily be determined by PCR-based gene walking. See Parker et al., *Nucl. Acids Res.* 19:3055–3060. A specific primer for the sequenced region is primed with a general primer that hybridizes to the flanking region.

Figure 19:
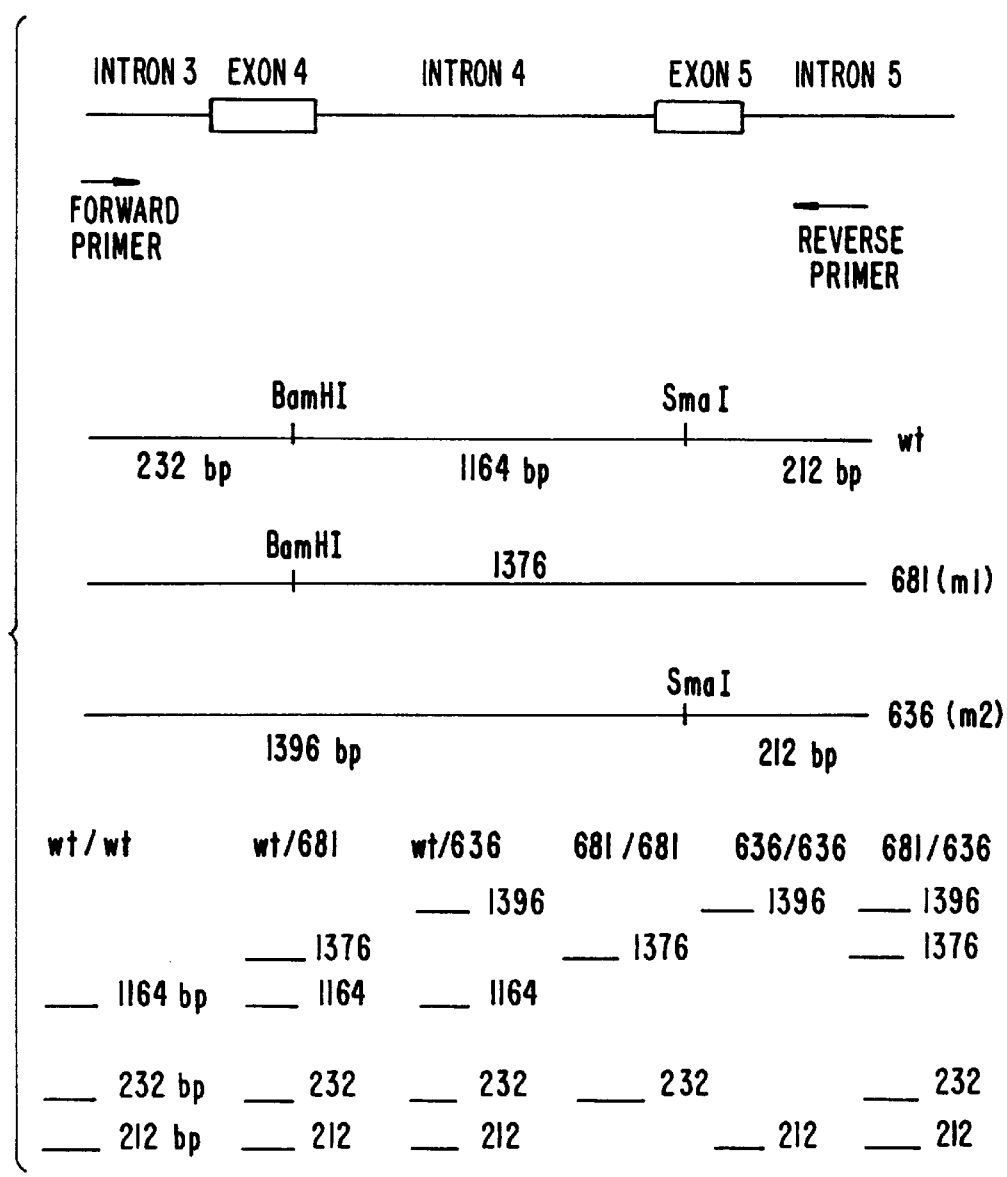
FIG. 19 Simultaneous detection of the 636 and 681 mutations.

Forward primers often comprise about 10–50 and preferably 15–30 contiguous nucleotides from the wildtype 2C19 sequences shown in FIGS. 15–17 (which is the coding or sense sequence). Reverse primers often comprise about 10–50 or 15–30 nucleotides from the complement of the wildtype 2C19 sequence shown in FIGS. 15–17. The complement of the sequence shown in FIGS. 15–17 is also referred to as the antisense sequences. A primer (or its complement) preferably exhibits 100% sequence identity with a corresponding 2C19 subsequence to which it hybridizes over a window of about 15–30 bp. For amplification of the 681 polymorphism, forward primers preferably comprise a segment of contiguous nucleotides from the fourth intronic region and reverse primers a segment of contiguous nucleotides from the fifth exonic or intronic region. For amplification of the 636 polymorphism, forward primers preferably comprise a segment of contiguous nucleotides from the third intronic region and reverse primers a segment of contiguous nucleotides from the fourth intronic region. For amplification of both the 636 and 681 polymorphisms, forward primers preferably comprise a segment of contiguous nucleotides from the third intronic region and reverse primers a segment of contiguous nucleotides from the fifth exonic region or fifth intronic region. See FIG. 19. As noted above, the spacing of the subsequences is not critical, but a separation of about 50–2000 bp. For simultaneous amplification of the 636 and 681 mutations, the spacing is typically 1000–1500 bp. For amplification of either mutation alone, a spacing of about 400 bp is typical.

Preferred primers exhibit perfect sequence identity to 2C19 and lesser sequence identity to corresponding regions of related genes, such as 2C9 and 2C18. Such primers are designed by comparison of the wildtype 2C19 sequence shown in FIG. 15–17 with corresponding sequences from 2C9 and 2C18 described by de Morais et al., supra. In general, sequence divergence between the three genes is expected to be greater in intronic sequences. An exemplary pair of primers for amplifying a segment spanning the 681 mutation is described in Example 7. A forward primer, 5'-AATTACAACCAGAGCTTGGC-3' (SEQ. ID. No. 55), exhibits perfect sequence identity to a subsequence from the wildtype 2C19 sense strand within intron 4. A reverse primer 5'-TATCACTTTCCATAAAAGCAAG-3' (SEQ. ID No. 56) exhibits perfect sequence identity to the antisense strand of the wildtype 2C19 sequence within exon 5. The amplification product from these primers has a length of 169 bp. An exemplary pair of primers for amplifying a segment spanning the 636 mutation is described in Example 8. A forward primer, 5'-TATTATCTGTTAACTAATATGA-3' (SEQ ID No. 57) exhibits perfect sequence identity to a subsequence from the wildtype 2C19 sense strand within intron 3. A reverse primer 5'-ACTTCAGGGCTTGGTCAATA-3' (SEQ. ID. No. 58) exhibits perfect sequence identity to the antisense strand of the wildtype 2C19 sequence within intron 4. The amplification product from these primers has a length of 329 bp.

Having amplified a segment of a 2C19 gene known to span a polymorphism, a variety of assays are available for determining whether a mutation is present in an individual under test. A generally applicable, but relatively laborious assay, is to sequence the amplified fragment across the polymorphic locus and compare the resulting sequence with the wildtype 2C19 sequence shown in FIG. 15–17.

A simpler assay, but one applicable to only certain mutations, is to compare the size or restriction profile of the amplified segment, optionally in comparison with a corresponding wildtype 2C19 segment. For the 681 polymorphism, restriction analysis provides a rapid and clear-cut means of identifying a mutant allele. The 681 polymorphism results in loss of a SmaI site and acquisition of an EcoRII site in mutant alleles. Thus, SmaI digestion of a wildtype allele produces an extra band compared with a mutant allele. For the amplification product obtained using the exemplified primers discussed above, SmaI digestion of the wildtype product yields fragments of 120 and 49 bp, whereas the mutant amplification product remains uncut yielding a single fragment of 169 bp. In individuals homozygous for the wildtype allele, only the 120 bp and 49 bp bands are present. In individuals homozygous for the mutant allele, only the 169 bp band is present. In heterozygotes, all three bands (i.e., 169, 120 and 49 bp) are present. The bands can usually be detected by agarose or acrylamide gel electrophoresis and ethidium bromide staining. If greater sensitivity is needed, the amplification product is labelled and the bands detected by, e.g., autoradiography. Of course, the assay can also be performed using an isoschizomer of SmaI with identical results. The assay can also be performed by digesting with EcoRII or an isoschizomer thereof. In this case, one obtains a mirror image of the results obtained for SmaI digestion, because the mutant 2C19 allele contains an additional EcoRII site relative to the wildtype allele. As a quality control measure, both SmaI and EcoRII digestions can be performed on separate aliquots of a test sample. Of course, any other enzyme that recognizes a site that includes the 681 polymorphism can also be used. For example, alternatives to SmaI (i.e., that cleave only the wildtype allele) include AvaI, MspI, NciI, ScrFI and TspEI).

The 636 polymorphism can be similarly analyzed by digestion with e.g., BamHI. BamHI digestion of a wildtype allele produces an extra band compared with a mutant allele. For the amplification product obtained using the exemplified primers discussed above, BamHI digestion of the wildtype product yields fragments of 233 and 96 bp, and digestion of the mutant product yields a single fragment of 329 bp. In individuals homozygous for the wildtype allele, only the 233 bp and 96 bp bands are present. In individuals homozygous for the mutant allele, only the 329 band is present. In heterozygotes, all three bands are present. Of course, other enzymes that cut the wildtype allele at the polymorphic locus but not the 636 mutant allele, or vice versa, can also be used. For example, alternatives to BamHI include AlwI, BsaJI, BstVI, DpnI, EcoRII, NlaIV, Sau3AI and ScrFI. Enzymes that recognize a site on the mutant allele including nucleotide 636, but do not recognize the wildtype allele, include HinfI and TfiI.

For simultaneous detection of the 681 and 636 polymorphisms after amplification of a fragment spanning both polymorphism, the DNA can be double digested with two of the enzymes mentioned above. One enzyme should distinguish between the mutant 681 allele from a wildtype allele and the other should distinguish the mutant 636 allele from a wildtype allele. For example, double digestion with SmaI and BamHI is suitable. The double digestion generates six different restriction patterns corresponding to the six possible genotypes: wt/wt, wt/681, wt/636, 681/681, 636/636 and 681/636. See FIG. 19.

In another assay, amplification products are subjected to single-stranded conformational analysis. See, e.g., Hayashi, *PCR Methods & Applications* 1, 34–38 (1991); Orita, *Proc. Natl. Acad. Sci. USA* 86, 2766–2270 (1989); Orita et al., *Genomics* 5, 874–879 (1989). This method is capable of detecting many single base mutations in DNA fragments up to 200 bp irrespective whether the mutation causes a change in restriction fragment profile. In this method, the PCR reaction is performed using at least one labelled nucleotide or labelled primer to obtain a labelled amplified fragment. The amplification product is then denatured and the strands resolved by polyacrylamide gel electrophoresis under non-denaturing conditions. Mutations are detected by altered mobility of separated single strands.

b. Selective Amplification of an Allelic Variant

An alternative method for detecting defined mutations in a 2C19 gene employs a selective strategy whereby a wildtype allele is amplified without amplification of a mutant allele (or vice versa). This is accomplished by designing one of the primers to hybridize to a subsequence overlapping a defined polymorphism (for example, the 681 polymorphism). Such a primer can be designed to hybridize to one polymorphic allele without hybridizing to the other. Thus, when such a primer is paired with a second primer hybridizing distal to the polymorphic region, amplification will only occur for one polymorphic allele.

For diagnosis of the 681 polymorphism, selective amplification of the wildtype allele of 2C19 can be accomplished using a forward primer that has about 10–50, and usually 15–30 nucleotides from the wildtype 2C19 sequence shown in FIG. 15 or 16, including nucleotide 681. Such a forward primer when paired with any suitable reverse primer downstream from nucleotide 681 (i.e., sufficiently complementary to the sense strand of 2C19 to hybridize therewith) can be used to amplify selectively the wildtype allele without amplifying a mutant allele. The selectivity between amplification of wildtype and mutant alleles is greatest when the 681 nucleotide occurs near, or preferably, at the 3' end of the primer. Because the extension forms from the 3' end of the primer, a mismatch at or near this position is most inhibitory of amplification. The same result can be achieved by using a reverse primer that has about 10–50 or usually 15–30 contiguous nucleotides from the complement of the wildtype 2C19 sequence shown in FIG. 15 or 16 (i.e., the antisense strand) including the nucleotide at position 681. Such a reverse primer can be paired with any suitable forward primer sufficiently complementary to a subsequence of the antisense strand of the 2C19 gene upstream from nucleotide 681 to hybridize therewith. The 681 nucleotide should again be at or near the 3' end of the reverse primer.

Selective amplification of a 681 mutant allele is accomplished by an analogous strategy in which primers are designed to hybridize to the mutant allele without hybridizing to the wildtype. A suitable forward primer for amplification comprises about 10–50 or usually 15–30 contiguous nucleotides from the mutant 2C19 sequence shown in FIG. 15 of 16 (i.e., the sense strand). The forward primer can be paired with any suitable reverse primer sufficiently complementary to the sense strand of a downstream 2C19 subsequence to hybridize therewith. Alternatively, the same result can be achieved using a reverse primer comprising about 10–50 or 15–30 contiguous nucleotides from the complement of the mutant 2C19 sequence shown in FIG. 15 or 16 (i.e., the antisense strand). Such a reverse primer can be paired with any suitable forward primer sufficiently complementary to the antisense strand of an upstream 2C19 subsequence to hybridize therewith.

For diagnosis of the 636 polymorphism, selective amplification of the wildtype allele of the 2C19 allele can be accomplished using a forward primer that has about 10–50, and usually 15–30 nucleotides from the wildtype 2C19 genomic sequence shown in FIG. 17, including nucleotide 636. Such a forward primer when paired with any suitable reverse primer downstream from nucleotide 636 (i.e., sufficiently complementary to the sense strand of 2C19 to hybridize therewith) can be used to amplify selectively the wildtype allele without amplifying a mutant allele. The 636 nucleotide usually occurs near, or preferably, at the 3' end of the primer. The same result can be achieved by using a reverse primer that has about 10–50 or usually 15–30 contiguous nucleotides from the complement of the wildtype 2C19 genomic sequence shown in FIG. 17 (i.e., the antisense strand) including the nucleotide at position 636. Such a reverse primer can be paired with any suitable forward primer sufficiently complementary to a sequence of the antisense strand of the 2C19 gene upstream from nucleotide 636 to hybridize therewith. The 636 nucleotide should again be at or near the 3' end of the reverse primer.

For selective amplification of a 636 mutant allele a suitable forward primer for amplification comprises about 10–50 or usually 15–30 contiguous nucleotides including nucleotide 636 from the mutant 2C19 genomic sequence shown in FIG. 17 (i.e., the sense strand). The forward primer can be paired with any suitable reverse primer sufficiently complementary to the sense strand of a 2C19 genomic subsequence downstream from nucleotide 636 to hybridize therewith. Alternatively, the same result can be achieved using a reverse primer comprising about 10–50 or 15–30 contiguous nucleotides including nucleotide 636 from the complement of the mutant 2C19 sequence shown in FIG. 17 (i.e., the antisense strand). Such a reverse primer can be paired with any suitable forward primer sufficiently complementary to the antisense strand of a 2C19 subsequence upstream from nucleotide 636 to hybridize therewith.

Following amplification, the sample under test is characterized as wildtype or mutant by the presence or absence of an amplification product. With a primer designed for selective amplification of the wildtype allele, the presence of an amplification product is indicative of that allele and the absence of an amplification product indicative of a mutant allele. The converse applies for primers designed for selective amplification of a mutant allele. In preferred assay, a sample is divided into two aliquots, one of which is amplified using primers for wildtype allele amplification, the other of which is amplified using primers appropriate for mutant allele amplification. The presence of an amplification product in one but not both of the aliquots indicates that the individual under test is either wildtype or a homozygous for the mutation (depending on aliquot in which the amplification product occurred). The presence of amplification product in both aliquots indicates that the individual is heterozygous. The absence of an amplification product in both aliquots would indicate either the absence of a 2C19 gene or a quality control problem in the amplification procedure requiring that the assay be repeated. Coamplification of a second known standard human gene using a second set of primers can aid in distinguishing between these possibilities. If both bands are missing, the problem is probably quality control, while amplification of only the standard gene is suggestive that the CYP2C19 gene may be deleted.

The presence or absence of amplification products can be detected by gel electrophoresis. Gels are usually visualized by ethidium bromide staining. However, if greater sensitivity is required fragments can be labelled in the course of amplification. Amplified fragments can be electrophoresed directly or can be cut with any restriction enzyme that releases fragments of a convenient size from the amplification products. For the simultaneous analysis of multiple samples, the dot-blot method may be advantageous. In the dot blot method, multiple unlabelled amplification mixtures are bound to discrete locations on a solid support, such as a membrane. The membrane is incubated with labeled probe under suitable hybridization conditions, the unhybridized probe removed by washing, and the filter monitored for the presence of bound probe.

c. Southern Blotting

For polymorphic mutations resulting in loss or acquisition of a restriction site (such as the 681 and 636 polymorphisms), samples of genomic DNA can also be analyzed by m Southern blotting without the need for prior amplification. The DNA is digested with an enzyme that cuts a wildtype allele but not a mutant allele or vice versa (e.g., BamHI, SmaI, EcoRII or HinfI, or isoschizomers of any of these). For analysis of the 681 polymorphism, digestion with SmaI or isoschizomers results in an additional fragment from the wildtype allele compared with the mutant allele. Digestion with EcoRII or isoschizomers results in an additional fragment from the mutant allele. Digestion products are detected with a 2C19 probe. For analysis of the 636 polymorphism, digestion with BamHI or isoschizomers results in an additional fragment from the wildtype allele compared with the mutant allele. Digestion with HinfI results in an additional fragment from the mutant allele. The probe can be any segment of a 2C19 DNA sequence that includes the polymorphism and extends for at least about 20 nucleotides on either side.

2. cDNA Assays

Defined polymorphisms can also be detected by analysis of cDNA by similar strategies to those employed for genomic DNA. However, the primers appropriate for amplification procedures are not necessarily interchangeable for the two substrates. Suitable primers for analysis of the 681 and 636 polymorphisms in cDNA are described below.

a. Amplification of Segments Spanning a Defined Mutation

The 681 polymorphism in genomic DNA results in a 40 bp deletion of cDNA comprising nucleotides 643–682 of the wildtype 2C19 cDNA or genomic sequence shown in FIG. 12. The forward primer and reverse primers are therefore designed to hybridize to 2C19 subsequences on opposite sides of this deletion. Thus, for example, a forward primer can hybridize to the antisense strand of a 2C19 sequence upstream from nucleotide 643 of the coding region. Such a forward primer should be paired with a reverse primer that hybridizes to the sense strand of the 2C19 sequence downstream from nucleotide 682. Nucleotides in a 2C19 DNA sequence are designated the numbers of corresponding nucleotides in the wildtype cDNA sequence shown in SEQ. ID. No. 2 (or FIG. 12, which shows a subsequence of SEQ. ID. No. 2), when the sequences are maximally aligned. Preferably, the forward primer comprises about 10–50 or 15–30 contiguous nucleotides upstream of nucleotide 645 from the wildtype 2C19 cDNA sequence shown in FIG. 12 or SEQ. ID. No. 2. Analogously, the reverse primer preferably comprises about 10–50 or 15–30 contiguous nucleotides from the complement of the wildtype 2C19 cDNA sequence shown in FIG. 12 or SEQ. ID. No. 2 downstream from nucleotide 682 of the coding region. For example, a forward primer comprising 5'-ATTGAATGAAAACATCAGGATTG-3' (SEQ. ID No. 59) and a reverse primer comprising 5'-GTAAGTCAGCTGCAGTGATTA-3' (SEQ. ID. No. 60) form a suitable pair. The amplification product from such primers is 40 bp longer for the wildtype 2C19 cDNA sequence than for the 681 mutant sequence.

For detection of the 636 polymorphism, the forward primer and reverse primers are designed to hybridize to 2C19 subsequences on opposite sides of nucleotide 636. Thus, for example, a forward primer can hybridize to the antisense strand of a 2C19 sequence upstream from nucleotide 636 of the coding region. Such a forward primer should be paired with a reverse primer that hybridizes to the sense strand of the 2C19 sequence downstream from nucleotide 636 (SEQ. ID. No. 2 or FIG. 12). Preferably, the forward primer comprises about 10–50 or 15–30 contiguous nucleotides upstream of nucleotide 636 from the wildtype 2C19 cDNA sequence shown in FIG. 12 or SEQ. ID. No. 2. Analogously, the reverse primer preferably comprises about 10–50 or 15–30 contiguous nucleotides from the complement of the wildtype 2C19 cDNA sequence shown in FIG. 12 or SEQ. ID. No. 2 downstream from nucleotide 636 of the coding region.

For simultaneous detection of the 636 and 681 polymorphisms, the forward primer should be as described for detection of the 636 polymorphism and the reverse primer as described for detection of the 681 polymorphism. These primers will amplify a segment of DNA spanning both the 636 and 681 polymorphisms.

Amplification products are usually analyzed by gel electrophoresis. The products can be analyzed uncut or can be cleaved with any restriction enzyme having a site in the amplification product. For detection of the 681 polymorphism, SmaI and its isoschizomers are particularly useful because of the presence of a restriction site present in wildtype 2C19 DNA that is not present in the mutant form. See FIG. 12. Similarly, BamHI and its isoschizomers are particularly useful for detection of the 636 polymorphism. Analysis of fragments allows distinction between wildtype, homozygous and heterozygous mutations as discussed for the corresponding genomic assay.

b. Selective Amplification of an Allelic Variant

For analysis of the 681 polymorphism, selective amplification of the wildtype variant is achieved by selecting a forward or reverse primer that overlaps nucleotides 643–682 of the wildtype 2C19 cDNA sequence (FIG. 12). This segment of nucleotides is not present in a mutant allele. Thus, a primer hybridizing to this segment of the wildtype allele will not hybridize to the mutant allele. Accordingly, such primers can be used to prime amplification of the wildtype allele without priming amplification of the mutant allele. For example, a forward primer that hybridizes to the complement of the wildtype 2C19 cDNA sequence shown in FIG. 12 between nucleotides 643–682 without hybridizing to the complement of the mutant 2C19 DNA sequence shown in FIG. 12 is suitable. Such a forward primer can be paired with any suitable reverse primer sufficiently complementary with a downstream subsequence of the sense strand of the 2C19 cDNA to hybridize therewith.

Alternatively, a reverse primer is designed that hybridizes to the wildtype 2C19 cDNA sequence shown in FIG. 12 between nucleotides 643 and 682 without hybridizing to the mutant 2C19 cDNA sequence shown in FIG. 12. Such a reverse primer can be paired with any suitable forward primer sufficiently complementary with an upstream subsequence of the antisense strand of the 2C19 cDNA to hybridize therewith.

Primers for selective amplification of the mutant allele can also be designed. A suitable primer hybridizes to two 2C19 subsequences, of about 1–50, 5–30 or 10–20 nucleotides, which subsequences are separated by nucleotides 643–682 in the wildtype sequence, but which are contiguous in the mutant sequence. Such primers hybridize to mutant 2C19 cDNA sequences without hybridizing to wildtype sequences. For example, a forward primer comprising a subsequence of nucleotides 633–642 of the wildtype 2C19 cDNA sequence shown in FIG. 12 joined to a second subsequence of nucleotides 684–693 of this sequence is suitable. This primer can be paired with any suitable reverse primer sufficiently complementary to a downstream subsequence of the sense strand of the 2C19 cDNA to hybridize therewith.

For analysis of the 636 polymorphism, primers can designed using the same strategy as discussed for selective amplification of genomic DNA except that the primers, which include nucleotide 636, are formed from nucleotide segments from cDNA rather than genomic sequences.

Amplification products are analyzed using the same methods as described for corresponding genomic amplification products.

F. Diagnostic Kits

The invention also provides kits comprising useful components for practicing the diagnostic methods of the invention. The kits comprise at least one of the primers discussed above. Kits usually contain a matched pair of forward and reverse primers as described above for amplifying a segment encompassing the 681 and/or the 636 polymorphism. Some kits contain two matched pairs of primers, e.g., one pair for analysis of the 681 polymorphism, the other pair for analysis of the 636 polymorphism. For selective amplification of mutant or wildtype alleles, kits usually contain a pair of primers for amplification of the mutant allele and/or a separate pair of primers for amplification of the wildtype allele. Optional additional components of the kit include, for example, restriction enzymes for analysis of amplification products, such as BamHI, SmaI, HinfI and/or EcoRII (or isoschizomers of any of these), reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

G. Nucleic Acid Fragments

In another aspect, the invention provides fragments of a mutant 2C19 allele spanning the 681 polymorphism and/or 636 polymorphism. The fragments usually have up to about 50, 100, 200, 500, 1000, 2000 or 10,000 bp of 2C19 sequence. Some fragments comprise at least about ten contiguous nucleotides including nucleotide 681 from the mutant 2C19 allele shown in FIG. 15. Other fragments comprise at least about ten contiguous nucleotides including nucleotide 636 from the mutant 2C19 allele shown in FIG. 17. The fragments can be single or double stranded. The fragments are provided in substantially purified form. Usually, the fragments are the result of PCR amplification. The fragments are useful in the diagnostic assays discussed above.

The following examples are provided to illustrate but not to limit the invention.

EXAMPLES

Materials. Human liver samples were obtained from organ donors through the National Disease Research Interchange in Philadelphia, Pa., and from the Human Liver Research Facility, Stanford Research Institute, Life Sciences Division, Menlo Park, Calif. Restriction endonucleases were purchased from Pharmacia LKB Biotechnology, Inc. (Piscataway, N.J.). [$\alpha$-$^{33}$] dCTP (3000 Ci/mmol) and [$\tau$-$^{32}$P] ATP (500 Ci/mmol) and [$\alpha$-$^{32}$S] dATP (650 Ci/mmol) were from Amersham Corp. (Arlington Heights, Ill.). All other reagents were of the highest quality available.

Conditions. Hybridization and washing conditions for screening libraries with random-labeled cDNAs for 2C13(g) or 254c used the same solutions as described for actin, but were performed at nonstringent temperatures (42° C.). Conditions for hybridization of clones with T300R were identical with those described above. Hybridization of cDNA clones with M300R (recognizes 2C9, 2C10, and 2C19) (5'-ACTTTTCAATGTAAGCAAAT-3') (SEQ. ID. No. 17) was identical except that for each oligomer the hybridization temperature and the high-stringency wash were 5° C. below the calculated melting temperatures.

Example 1

Construction and Screening of Human Liver cDNA Libraries

Two cDNA libraries were constructed from human livers 860624 and S33, which differed phenotypically in the hepatic content of P450 HLx (2C8) (SEQ. ID. No. 8). Several partial cDNA clones were found but no full-length clones.

A second cDNA library (from a liver phenotypically high in HLx) was then screened. Eighty-three essentially full-length (>1.8 kb) clones belonging to the 2C subfamily were isolated from this library. These include full-length clones for two additional new members of the 2C subfamily.

The majority of the cDNAs characterized in the high-HLx library (60%) were one of two allelic variants of 2C9, while 35% represented 2C8 (SEQ. ID. No. 8). Two new genes were identified (two allelic variants of 2C18 and 2C19).

The two cDNA libraries from individuals phenotypically high and low in HLx were examined to determine whether a variant mRNA for 2C8 (SEQ. ID. No. 8) was responsible for the polymorphic expression of HLx and to identify additional members of the 2C subfamily. No clones for 2C8 (SEQ. ID. No. 8) were isolated from the individual phenotypically high individual. Two allelic variants for 2C9 were isolated. In addition, full-length cDNAs for two additional new members (2C18 and 2C19) were isolated. These new members of the 2C subfamily were expressed in COS-1 cells and shown to be immunochemically distinct from HLx and 2C9, and 2C18 metabolized racemic mephenytoin.

Total human liver RNA was prepared by the guanidine hydrochloride method (Cox, *Methods Enzymol.* 12:120–129 (1968)) from two human livers either low (860624) or high (S33) in HLx as identified by immunoblot analysis. Poly (A+)RNA was then isolated by two passages over an oligo (dT)-cellulose column (Aviv et al., *Proc. Natl. Acad. Sci. U.S.A.* 69:1408–1412 (1972)). The low-HLx cDNA library was prepared by Stratagene Cloning systems (La Jolla, Calif.), and the double-stranded cDNA was treated with S1 nuclease. Following the addition of EcoRI linkers, the double-stranded cDNA was size-fractionated on a CL-4B Sepharose column. The largest fraction was ligated into $\lambda$ZAPII and then transfected into XL1-Blue. The high-HLx cDNA library was constructed following the methods of Watson et al., in *DNA Cloning* (Glover, D. M., Ed.) 1:79–88, IRL Press, Washington, D.C. (1985)). Double-stranded cDNA was ligated to EcoRI linkers, size-fractionated on an agarose gel (1.8–2.4 kb), and then ligated into $\lambda$ZAPII (Stratagene) and transfected into XL1-Blue.

The low-HLx library was screened under conditions of low stringency with a $^{32}$P-labeled rat P450 2C13 cDNA probe and with oligonucleotides for human 2C8 (SEQ. ID. No. 8) (T300R) (5'-TTAGTAATTCTTTGAGATAT-3') (SEQ. ID. No. 18) and 2C9 (M300R) (5'-CTGTTAGCTCTTTCAGCCAG-3')(SEQ. ID. No. 19). The high-HLx library was screened under conditions of low stringency using a $^{32}$P-labeled 254C cDNA probe derived from the first library and M300R (2C9). Positive clones were isolated, transfected into XL1-Blue, and excised into the plasmid Bluescript, according to Stratagene's excision protocol.

Screening the cDNA library constructed from a low-HLx individual with a cDNA for rat 2C13 under nonstringent conditions and with oligonucleotide probes specific for 2C8 (SEQ. ID. No. 8) and 2C9 yielded several clones for 2C9 and a partial DNA, clone 254c, which now appears to be an incompletely characterized splice variant of the P450 2C subfamily. None of the clones identified in this library were full-length. Clone 186 was identical with but 25 base pairs longer than MP-4, a 2C9 clone previously described by Ged et al. (1988).

Approximately 40000 plaques were then screened from the library from liver S33 with the cDNA for 254c under non-stringent conditions and with an oligonucleotide probe specific for 2C9. Eighty-three essentially full-length 2C clones (>1.8 kb) were isolated, purified, and partially or completely sequenced (Table I). Of these, 29 clones were found to encode cytochrome P450 2C8 (SEQ. ID. No. 8). One clone (7b) of 2C8 (SEQ. ID. No. 8) was isolated which was similar to Hpl-1 and Hpl-2 reported by Okino et al.(1987), but different by having a tyrosine at position 130 instead of an asparagine and an isoleucine at 264 instead of a methionine.

TABLE I

Distribution of P450 2C cDNA Clones from Human Liver S33*

|  | No. of Clones | % Distribution |
|---|---|---|
| 2C8 (SEQ. ID. No.8) | 29 | 35 |
| 2C9 |  |  |
| 65 (SEQ. ID. No. 10) | 39 | 47 |
| 25 (SEQ. ID. No. 4) | 11 | 13 |
| 2C10 | 0 | 0 |
| 2C18 |  |  |
| 29c (SEQ. ID. No. 6) | 1 | 1.2 |
| 6b (SEQ ID No. 12) | 2 | 2.5 |
| 2C19 (11A) (SEQ ID No. 2) | 1 | 1.2 |
| Total | 83 | 100 |

*Clones were classified by hybridization with specific oligonucleotide probes and partial sequencing.

There are a number of polymorphisms in the human CYP2C subfamily. These include variations in the hepatic levels of HLx (Wrighton et al., *Arch. Biochem. Biophys.* 306:240–245 (1987)) and metabolic variations in the hepatic metabolism of S-mephenytoin. The molecular basis for these polymorphisms has not been characterized. 2C8 (SEQ. ID. No. 8) appears to encode the protein for HLx on the basis of its N-terminal amino acid sequence (Okino et al., *J. Biol. Chem.* 262:16072–16079 (1987); Wrighton et al., supra; Lasker et al., *Biochem. Biophys. Res. Commun.* 148:232–238 (1987)).

Example 2

Sequence Analysis

The Bluescript plasmids containing the positive cDNA inserts from the low-HLx library were purified by CsCl gradients, while the plasmids containing cDNA inserts from the high-HLx library were purified by using Qiagen plasmid purification kits (Qiagen, Inc., Studio city, Calif.). The double-stranded cDNA inserts were sequenced by the dideoxy chain termination method reported in Sanger et al., *J. Mol. Biol.* 162:729–773 (1982), using Sequenase kits (U.S. Biochemical Corp., Cleveland, Ohio). The full-length clones 65 (SEQ. ID. No. 10), 25 (SEQ. ID. No. 4), 7b, 11a (SEQ. ID. No. 2), 29c (SEQ. ID. No. 6) and 6b (SEQ. ID. No. 12) were sequenced completely in both directions with primers spaced approximately 20 bases apart. The remaining positive clones from the high-HLx cDNA library were sequenced in both directions through both the 5' and 3' ends and through all the regions which would identify any of the known allelic variants.

The majority of the clones (50) isolated from the library from liver S33 coded for 2C9. Interestingly, all of the 50 clones appeared to be 1 of 2 2C9 allelic variants, typified by the full-length clones 65 (SEQ. ID. No. 10) and 25 (SEQ. ID. No. 4). All of these clones were sequenced through the 5' and 3' ends and through regions which would identify known allelic variants. Thirty-nine of the 2C9 clones were identical with clone 65 (SEQ. ID. No. 10), and 11 were identical with clone 25 (SEQ. ID. No. 10).

The nucleotide sequence for clone 65 (SEQ. ID. No. 10) and clone 25 (SEQ. ID. No. 4) is shown in FIG. 2. Clones 25 (SEQ. ID. No. 4) and 65 (SEQ. ID. No. 10) were identical in the 5'- and 3'-noncoding regions but contained two single-base changes at positions 1075 and 1425. One of these base changes was conservative, but the second would result in one amino acid difference at position 359 (isoleucine versus leucine). clone 65 (SEQ. ID. N. 9) is identical in amino acid sequence with human form 2, although it differs by two silent changes in the coding region and four differences in the noncoding region (Yasumori et al., 1987). Clone 65 (SEQ. ID. No. 9) contained a leucine instead of a isoleucine at position 4, a valine instead of a serine at position 6, and an arginine instead of a cysteine at position 144 compared to the 2C9 sequenced by Kimura et al. (1987). The 2C9 reported by Meehan et al. has substitutions at positions 144, 175, and 238 compared to the clones obtained in this invention (Meehan et al., *Am J Hum Genet.*, 42:26–37 (1988)).

The remaining clones characterized from the human liver S33 cDNA library encode several novel P450 2C cDNAs. Their DNA sequences are shown in FIG. 2 and their percent homology with other known 2C members shown in Table II. Two of these clones, 29c (SEQ. ID. No. 6) and 6b (SEQ. ID. No. 12), differ by one nucleotide in the coding region (position 1154), which would result in a single amino acid change (threonine vs methionine at position 385). Clone 29c (SEQ. ID. No. 6) had a very long (198 bp) 5'-noncoding sequence and a polyadenylation signal 21 bases from the poly (A) tail. Clone 6b (SEQ. ID. No. 12) had an unusually long 3'-noncoding region containing three possible polyadenylation signals with no poly(A) tail. The differences in the 3'-noncoding region could represent alternate splicing, allelic variants, or possibly separate genes. However, these clones are designated as allelic variants of (2C18) because they differ by only one base in the coding region. They are most similar to 2C9 (82% amino acid homology) and 2C19 (SEQ. ID. No. 2) (81% amino acid homology) (Table II).

A third unique P450 2C cDNA, clone 11a (SEQ. ID. No. 2) (designated 2C19), was also identified. 2C19 is 92% homologous in its amino acid sequence to 2C9, 81% homologous to 2C18, and 79% homologous to 2C8 (SEQ. ID. No. 8). Clone 11a (SEQ. ID. No. 2) had a short 5'-leader sequence and contained the stop codon, but did not have a polyadenylation signal or poly(A) tail. Interestingly, no clones for 2C10 (MP-8) were isolated from either library, despite the sequencing of the 3' region of all 50 putative 2C9 clones.

TABLE II

Percent Homology for Nucleotide and Amino Acid Sequences of P450 2C cDNAs*

| Clone | 2C8 (SEQ ID NO.8) | 2C9 | 29c (SEQ ID NO.6) (2C18) | 11a (SEQ ID NO.2) (2C19) |
|---|---|---|---|---|
| 29c (2C18) | 84 | 86 | 100 | 86 |
| (SEQ ID NO.6) | 89 | 93 | 100 | 93 |
| 11a (2C19) | 83 | 94 | 86 | 100 |
| (SEQ ID NO.2) | 91 | 96 | 93 | 100 |

*For each comparison, the upper value represents percent nucleotide homology, and the lower value represents percent amino acid homology. The nucleic acid comparisons include both the coding and 3'-non-coding regions. The 2C9 sequence used in this comparison was the cDNA sequence for clone 65.

FIG. 4 shows the alignment comparisons for the deduced amino acid sequences of all known members of the human CYP2C family, including the three new P450s of the present invention. The 7 proteins, along with the consensus sequence, can be aligned with no gaps, and each is predicted to be 490 amino acids long. The amino acid sequences show marked similarities with many regions of absolute conservation. Regions of marked conservation are noted form 131 to 180, and from 302 to 460. These human P450 2C protein sequences also demonstrate hypervariable regions which may be important for interactions between the enzyme and substrate. These include the region from 181–120 and 220–248 as well as 283–296 and a short region near the carboxyl terminus at 461–479. Notably, it has been reported that a putative recognition site for phosphorylation of P450 by cAMP-dependent kinase for P450 2B1 (Arg-Arg-Phe-Ser) at positions 124–127 was conserved in 2C8 (SEQ. ID. No. 8), 2C9, and 11 (2C19), suggesting that these cytochromes might be regulated by phosphorylation (Muller et al., *FEBS Lett.* 187:21–24 (1985).

However, 2C18 did not contain a serine at this site. The overall percent homology for both nucleic acid and protein sequences is summarized in Table II.

Two additional full-length allelic variants of 2C9 have been isolated. One of these clones is identical with MP-4, but is full-length. It varies from the almost full-length human form 2 isolated by Yasumori et al., supra, by only two silent base changes in the coding region and by four changes in the noncoding region. The number of differences in the nucleic acid sequences of the presumed allelic variants isolated by different laboratories range from 4 to 17 and the amino acid changes vary from 0 to 4, as illustrated in FIG. 3. Two of the amino acid differences occur within the first six N-terminal residues, the others occurring singly throughout the sequence. The effect of these changes on catalytic activity has not been systematically studied. In Relling et al., *J. Pharmacol. Exp. Ther.* 252:442–447 (1990), it was reported that when the cDNAs for 2C8 (SEQ. ID. No. 8) and 2C9 4-hydroxylated racemic mephenytoin but did not metabolize (S)-mephenytoin. However, the form of isolated 2C9 (human form 2) which is described in Yasumori et al. (1990), metabolized (S)-mephenytoin preferentially when expressed in yeast. These forms differed by only three amino acids. In contrast, Brian et al., *Biochemistry* 28:4993–4999 (1989) found that when a full-length MP-8 (constructed with the first 15 nucleotides predicted from the known amino acid sequence of P450$_{mp-1}$) was expressed in yeast, it did not metabolize (S)-mephenytoin. This form would differ from human form 2 by only two amino acids. Thus, the role of 2C9 in (S)-mephenytoin metabolism remains controversial.

Example 3

Human RNA Blot Analysis and Hybridization Conditions

Poly(A+) RNA (10 μg) was electrophoresed in a 1% agarose gel under denaturing conditions and transferred to a Nytran filter (Micron Separation, Inc., Westboro, Mass.), and filters were then baked for 2 h at 80° C. The filters were prehybridized for 2 h, then hybridized overnight with a $^{32}$P-labeled specific oligonucleotide probe for 2C8 (SEQ. ID. No. 8) (T300R) at 42° C., washed 3×5 min at room temperature and 1×5 min at 42° C. with 2× SSC/0.1% SDS, and radioautographed. Filters were then stripped with 5 mM Tris (pH 8.0), 0.2 mM EDTA, 0.05% sodium pyrophosphate, and 0.1× Denhardt's for 2 h at 65° C. and rehybridized with a random-primed actin cDNA (Oncor, Gaithersburg, Md.) at 50° C. using 6× SSC, 4× Denhardts, and 0.5% SDS. These filters were washed 1×5 min at room temperature, 1×10 min at 48° C., and 4×15 min at 48° C. and radioautographed as before. The 2C8 mRNA band was quantitated by scanning with an LKB Ultrascan laser densitometer, and the values of the integrated peaks were divided by those of the actin peaks.

Hybridization with T300R was negligible in mRNA from 860624 compared to S33 and a number of other liver samples (FIG. 5). When corrected for hybridization with the actin probe, the amounts of 2C8 (SEQ. ID. No. 8) mRNA were consistent with the relative amounts of HLx observed in Western blot analysis. Laser scans of the autoradiographs indicated that 2C8 (SEQ. ID. No. 8) mRNA levels in sample 860624 were at least 70-fold lower than in S33 and 3 to 15-fold lower than in any of the remaining samples.

Example 4

Cell Expression Studies cDNA inserts were ligated into the cloning region of the expression plasmids pSVL (Pharmacia LKB biotechnology, Inc., Piscataway, N.J.) or pcD (Okayama et al., *Mol. Cell. Biol.* 3:280–289 (1983)) and used to transform COS-1 cells. COS-1 cells were placed at (1–2)×10$^6$ cells per 1-cm dish and grown for 24 h in Dulbecco's-modified Eagle's medium with 10% fetal bovine serum (DMEM). The cells were then washed with Dulbecco's phosphate-buffered saline (PBS) and transfected with recombinant plasmid (3 μg per dish) in DEAE-dextran (500 μg/mL) for 30 min-1 h at 37° C. The transfected cells were then treated with chloroquine (52 μg/mL) in DMEM for 5 h (Luthman et al., *Nucleic Acids Res.* 11:1295–1308 (1983)), washed with PBS, refed with DMEM, and incubated for 72 h prior to harvest. Typically, 15–20 dishes were transfected with each recombinant plasmid. For Western blot analysis of the recombinant transformed COS-1 cells, cells were scraped from the dishes into buffer (50 mM Tris-HCl, pH 7.5, 150 mM KCl, and 1 mM EDTA) and lysed with 3×5 s bursts with a polytron. A portion of each lysate was centrifuged at 9000 g and then 10000 g for the preparation of a microsomal fraction. Western blots were then performed as described above. Total RNA was isolated from transfected COS-1 cells, and Northern blots were performed as described for human samples. The filters were hybridized with a $^{32}$P-labeled oligonucleotide probe which hybridizes with all 2C clones isolated (2C500R) (5'-GGAGCACAGCCCAGGATGAA-3') (SEQ. ID. No. 20) at 55° C., and radioautographed.

The two variant cDNAs for 2C9, the two variant cDNAs for 2C18, and the cDNA for 2C19 were inserted into expression vectors and transfected into COS-1 cells. Cell lysates were prepared and immunoblotted by using antibody to HLx and P450 2C9. The results are shown in FIG. 4. Transfection of COS-1 cells with the two variants of 2C9 (25 (SEQ. ID. No. 4) and 65 (SEQ. ID. No. 10)) resulted in the expression of a protein (SEQ. ID. No. 3) with a molecular weight equal to that of pure 2C9. In contrast, neither 2C18 (either variant) nor 2C19 was detected by antibody to HLx or 2C9. However, Northern blot analysis indicated that all three cDNAs had been successfully transfected into these cells. The sizes of the transcripts were those expected for the constructs. The somewhat lesser hybridization of the 2C oligoprobe with RNA from cells transfected with 11a (SEQ. ID. No. 2) reflects a lower amount of RNA in this sample as shown by the hybridization with the actin probe.

Example 5

Expression of Cytochrome P450 2C19 and 2C18 Polypeptides in a Stable Cell Line

1. Materials (a) Liver Samples and Chemicals

Human liver samples were obtained from Dr. Fred Guengerich, University of Vanderbilt, Nashville, Tenn. Restriction endonucleases were purchased from Stratagene Cloning Systems (La Jolla, Calif.). [α-$^{32}$P]dCTP (3000

Ci/mmol), [τ³²P]ATP (5000 Ci/mmol) and [α-³⁵S]dATP (650 Ci/mmol) were from Amersham Corp. (Arlington Heights, Ill.). Nirvanol was obtained from Adrian Küpfer, University of Berne, Switzerland and separated into its R- and S- enantiomers as described by Sobotka et al., *J. Amer. Chem. Soc.* 54:4697–4702 (1932). Radiolabelled S- and R-mephenytoin (N-methyl-¹⁴C) were synthesized by E.I. DuPont de Nemours & Co., Inc. (Wilmington, Del.) by methylation of R- and S-nirvanol. The radiochemical purity of both isomers was greater than 90% as assessed by HPLC. A single impurity which accounted for less than 2% of the parent compound was not characterized, since it eluted after the metabolites and parent compound. Moreover, the percentage of the impurity remained the same (less than 2%) before and after incubations. All sequencing was done by the dideoxymethod using Sequenase Kits (U.S. Biochemical Corp., Cleveland, Ohio). The specific activities of the S- and R-enantiomers were 20.7 and 20.9 mCi/mmol respectively. All other reagents used are listed below or were of the highest quality available.

(b) Additional Sequences of 2C cDNAs Used in the Expression Studies

Two full-length clones of 2C8 (7b and 7c) described in Romkes et al., *Biochemistry* 30:3247–3255 (1991), were sequenced through the coding region in the present study. The sequences were similar to that of the 2C8(HP1–1) reported by Okino et al., supra; however, both clones had coding changes at position 390 (A→C) (Asn¹³⁰Thr) and G→C at position 792 (Met²⁶⁴→Ile) and a change in the noncoding region at 1497(T→C). These changes presumably represent a second allelic variant of 2C8. The Thr¹³⁰ and Ile²⁶⁴ amino acids found in our 2C8 clones are conserved in the remainder of the human P450 2C subfamily (2C9, 2C18, and 2C19) and are therefore consistent with the amino acid substitutions in other members of this subfamily.

(c) Yeast Strains and Media

*Saccharomyces cerevisiae* 334 (MAT α, pep 403, prb1-1122, ura 3-52, leu 2-3, 112, reg1-501,gal1), a protease deficient strain kindly provided by Dr. Ed Perkins (NIEHS), was used as the recipient strain in these studies and propagated non-selectively in YPD medium (1% yeast extract, 2% peptone, 2% dextrose) (Hovland et al., *Gene* 83:57–64 (1989)). For the selection of Leu⁺ transformants, the cells were grown in synthetic complete medium minus leucine (Rose et al., *Methods in Yeast Genetics* (Rose et al., eds.) pp. 180–187, C.S.H.P., NY 1990). Plates were made by the addition of 2% agar.

2. Methods (a) Amplification of 2C18 and 2C9 RNA for Direct Sequencing

Total RNA from selected human liver samples was isolated by the single-step method (Chomozynski et al., *Anal. Biochem.* 163:156–159 (1987), using TRIREAGEN™ (Mol. Res. Center, Inc., Ohio). RNA (10 µg) was reverse transcribed using 2.6 µM random hexamers as the 3'-primer by incubating for 1 hour at 42° C. using 2.5 U/µl of M-MLV reverse transcriptase (BRL, Grand Island, N.Y.) in 10 mM Tris-HCl, pH 8.3, 5 mM KCl, 5 mM MgCl₂, 1 U/µl RNase inhibitor (Promega, Madison, Wis.) and 1 mM each of DATP, dCTP, dGTP, and dTTP (Perkin Elmer Cetus, Norwalk, Conn.). The samples were then heated for 5 minutes at 99° C. to terminate the reverse transcription.

The cDNA was then amplified for a region containing the allelic differences in 2C18 and 2C9 using a nested PCR method. The DNA was amplified in 1× PCR buffer (50 mM KCl, 10 mM Tris-HCl, pH 8.3) containing 1 mM MgCl₂, 0.2 mM each of dATP, dCTP, dGTP, dTTP and 20 pmol of each of the 5' and 3' primers in a final reaction volume of 100 µl. The reaction mixture was heated at 94° C. for 5 minutes before addition of 2.5 U of AmpliTaq DNA polymerase (Perkin Elmer Cetus). For PCR of 2C18, the 3'-primer was 5'-TGGCCCTGATAAGGGAGAAT-3' (SEQ. ID. No. 23) and the 5'-primers were 5'-ATCCAGAGATACATTG ACCTC-3' (SEQ. ID. No. 24) (outer) and 5'-CCATGAAG TGACCTGTGATG-3' (SEQ. ID. No. 25) (inner). For 2C9, the 3'-primer was 5'-AAAGATGGATAATGCCCCAG-3' (SEQ. ID. No. 26) and the 5'-primers were 5'-GAAGGAGATCCGGCGTTTCT-3' (SEQ. ID. No. 27) (outer) and 5'-GGCGTTTCTCCCTCATGACG-3' (SEQ. ID. No. 28) (inner). The outer amplification was performed for 20 cycles consisting of denaturation at 94° C. for 1 minute, annealing at the appropriate temperature for 30 seconds, and extension at 72° C. for 1 min. After a 50-fold dilution, PCR was carried out similarly with the inner primers for 35 additional cycles.

The PCR products were purified using a Centricon-30, dried, suspended in 40 µl of sterile water, and sequenced using Sequenase Kits and a P³³-end labeled sequencing primer. For 2C18, the primer used was 2C18.1184R 5'-TTGTCATTGTGCAG-3' (SEQ. ID. No. 29). Sequencing primers for 2C9 were 2C9.1030F 5'-CACATGCCCT ACACA-3' (SEQ. ID. No. 30), 2C9.385F 5'-TGACGCT GCGGAATT-3' (SEQ. ID. No. 3), and 2C9.783F 5'-GGACTTTATTGATTG-3(SEQ. ID. No. 32).

Full length 2C9 cDNA was also amplified by PCR from a human liver with high S-mephenytoin 4'-hydroxylase activity using the primers 5'-ATGATTCTCTTGTGGTCCT-3' (SEQ. ID. No. 33) and 5'-AAAGATGGATAATGC CCCAG-3' (SEQ. ID. No. 34). The PCR reaction was similar to above, except that the primer concentrations were increased 10-fold (0.25 µM). The PCR products were then cloned into the pCR1000 vector using the TA Cloning System (In Vitrogen, San Diego, Calif.) and sequenced to identify the allelic variant present.

(b) Plasmid Construction and Methods for Amplifying Full-length 2C18 and 2C19 cDNAs by PCR The strategy for cloning the P450 2C cDNAs into the yeast vector pAAH5 is described below. The 5'-noncoding sequence of the P450 2C cDNAs was eliminated by PCR amplification to optimize expression in yeast cells. The 5'-primer introduced a Hind III cloning site and a six A-residue consensus sequence upstream of the ATG codon to promote efficient translation in yeast (Hamilton et al., *Nucl. Acids Res.* 15:3581–3593 (1987), Cullin et al., *Gene* 65:203–217 (1988)). The 3'- primer was positioned between the stop codon and polyadenylation site and introduced a second Hind III site. cDNA inserts in the pBluescript vector (0.1 µg) (Romkes et al., (1991), supra) were amplified by PCR as described before except that the reaction contained 3.5 mM MgCl₂, 0.25 µM each of the 5'- and 3'- primers, and 1 µl PerfectMatch (Stratagene, La Jolla, Calif.). Amplification was performed in sequential cycles, with the first cycle including denaturation for 1 min. at 94° C., annealing at the appropriate temperature for 1 min., and polymerization at 72° C. for 3 min. The remaining 24 cycles consisted of a denaturation step at 94° C. for 1 min. and a combined annealing/extension step at 72° C. for 3 min. After the last cycle, all samples were incubated an additional 10 min. at 72° C. The primers used were: 2C8: 5'-GCAAGCTTAAAAAAATGGAACCTTTTGTGGTCCT-3' (SEQ. ID. No. 35) and 5'-GCAAGCTTGCCAGATGGGC TAGCATTCT-3' (SEQ. ID. No. 36); 2C9: 5'-GCAAGCTTAAAAAAATGGATTCTCTTGTGGTCCT-3' (SEQ. ID. No. 37) and 5'-GCAAGCTTGCCAGG CCATCTGCTCTTCT-3' (SEQ. ID. No. 38); 2C19: 5'-GCAAGCTTAAAAAAATGGATTCTCTTGTGGTCCT-3' (SEQ. ID. No. 39) and 5'-GCAAGCTTGCCA GACCATCTGTGCTTCT-3' (SEQ. ID. No. 40).

The PCR products were cloned into the pCR1000 vector (InVitrogen, San Diego, Calif.). Recombinant plasmids were isolated from E. coli (INVαF') cells using Qiagen plasmid purification kits, and the PCR products were completely sequenced as described above to verify the fidelity of the PCR reaction. A mutation of $ASP^2 \rightarrow Val$ was initially introduced inadvertently in 29c via the primers utilized due to an error in the original sequencing at this position. Therefore, the correct 2C18-$Asp^2$ cDNAs were cloned into the pAAH5 vector by an alternate strategy. The 3'-end was cut with NdeI, blunted, and ligated to a SmaI/HindIII adapter. The clone was then partially digested with BamHI which cuts after the initiation ATG as well as internally, and the intact 1700 fragment get purified. A BamHI/HindIII linker was prepared from the oligos 5'-AGCTTAAAAAAATG-3' (SEQ. ID. No. 41) (upper) and 5'-GATCCATTTTTTTA-3' (SEQ. ID. No. 42) (lower), annealed, and ligated to the cDNA fragment to introduce a HindIII cloning site and regenerate the ATG codon.

The PCR amplified cDNAs were isolated by Hind III digestion, ligated into the pAAH5 yeast expression vector, and the proper orientation confirmed by restriction analysis and sequencing. The expression vector pAAH5, which contains the yeast ADH1 promoter and terminator regions and the Leu2 selectable marker, was kindly provided by Dr. M. Negishi (NIEHS). The recombinant plasmids were isolated from E. coli Dh5α cells using Qiagen plasmid purifications kits and transformed into yeast as described previously (Faletto et al., J. Biol. Chem. 267:2032–2037 (1992), using the lithium acetate method of Ito et al., J. Bacteriol. 153:163–168 (1983).

(c) Immunoblots and Cytochrome P450 Determinations

Yeast microsomes or whole cell lysates were prepared from transformed cells isolated at mid-logarithmic phase as described previously (Oeda et al., supra) with slight modifications (Faletto et al., supra) and stored at –80° C. in 0.1M phosphate (pH 7.4) containing 20% glycerol and 0.1 mM EDTA. Protein concentrations were determined by the method of Bradford et al., Anal. Biochem. 72:248–254 (1976). SDS-polyacrylamide gel electrophoresis and Western blots were performed on yeast microsomes or whole cell lysates (Faletto et al., supra) and immunoblots probed with antibody to the appropriate P450 as described (Yeowell et al., Arch. Biochem. Biophys. 243:408–419 (1985). Cytochromes P450 2C8, P450 2C9 and NADPH:P450 reductase were purified from human liver microsomes (Raucy et al., Methods in Enzymol. 208:577–587 (1991) and antibodies to 2C8 and 2C9 prepared in rabbits as previously described (Leo et al., Arch. Biochem. Biohys. 269:305–312 (1988)). Specific peptides $NH_2$-CIDYLPGSHNKIAENFA-COOH (SEQ. ID. No. 43) (amino acids 231–249) for P450 2C18 and $NH_2$-CLAFMESDILEKVK-COOH (SEQ. ID. No. 44) (amino acids 236–249) for 2C19 were selected from amino regions where these P450s vary from other known 2C subfamily members (Romkes et al., (1991), supra). These peptides were synthesized, conjugated to bovine serum albumin via m-maleimidobenzoyl-N-hydroxysuccinimide ester, and antibodies to the conjugates raised in rabbits by BIOSYNTHESIS INC. (Denton, Tex.). E. coli lysate (4 mg/ml) was added to the primary peptide antibody in first step of the immunoblot procedure to block non-specific reactions of these rabbit antibodies to yeast cell wall proteins. Cytochrome P450 concentrations of microsomes were determined by dithionite-reduced carbon monoxide difference spectra by the method of Omura et al., J. Biol. Chem. 239:2370–2378 (1964) using an extinction coefficient of 91 mM-1 $cm^{-1}$.

Microsomes of human livers were prepared as described by Raucy et al., supra. SDS-polyacrylamide gel electrophoresis and immunoblot analysis was performed as above except that immunoblots were developed using the ECL (enhanced chemiluminescence) Western blotting kit from Amersham (UK). Immunoblots were scanned with a laser densitometer (LKB Instruments).

(d) Purification of Cytochromes from Recombinant Yeast Microsomes

Recombinant yeast microsomes were prepared from a 10–12 l culture, and recombinant P450s were purified by aminooctylsepharose chromatography as described by Iwasaki et al., J. Biol. Chem. 226:3380–3382 (1991). The Emulgen was then removed from protein by adsorption of the protein to a 4 g hydroxylapatite column (Hypatite C, Clarkson Chemical Company, Williamsport, Pa.) equilibrated with 10 mM potassium phosphate buffer (pH 7.2), 20% glycerol, 0.1 mM EDTA, and 0.1 mM DTT and washing the column with the same buffer until the absorbance at 280 nm returned to zero. The P450 was then eluted with 4090 mM DTT, and dialyzed overnight against 100 mM potassium phosphate buffer (pH 7.4, 20% glycerol and 0.1 mM EDTA. Absolute and CO difference spectra of purified P450s were determined in the same buffer but containing 0.2% Emulgen and 0.5% cholate.

(e) Tolbutamide Hydroxylase Assays

Tolbutamide hydroxylase activity was measured according to Knodell et al., J. Pharmacol. Exper. Ther. 241:1112–1119 (1987), with several modifications. Yeast microsomes (1 mg protein) were preincubated with 300 pmol hamster P450 reductase in 0.2 ml of the incubation buffer (below) for 3 min at 37° C. The reaction was then placed on ice and incubated in 0.2 ml of 50 mM HEPES buffer (pH 7.4) containing 1.5 mM $MgCl_2$, 0.1 mM EDTA in a final volume of 1 ml and 1 mM sodium tolbutamide. The reaction was initiated with 0.5 mM NADPH. Human liver microsomes (0.22 mg protein) were incubated without reductase. Incubations with reconstituted recombinant P450s contained 50 pmol purified P450 enzyme, 150 pmol P450 reductase, and 15 μg dilauroylphosphatidyl-choline, and were performed in 100 mM potassium phosphate buffer (pH 7.4). Reactions were terminated after 60 min at 37° C. by the addition of 50 μl of 4N HCl, followed by extraction with 3 ml of water-saturated ethyl acetate. The ethyl acetate extracts were dried under nitrogen at 40° C., the residue resolubilized in 200 μl methanol, and 4-hydroxytolbutamide then assayed using HPLC by injecting 50 μl of the solubilized extract onto a μBONDAPAK $C_{18}$ column (4.6×300 mm) using 0.05% phosphoric acid, pH 2.6: acetonitrile (6:4, v/v) as the mobile phase with a flow rate of 1 ml/min. The column eluate was monitored at 230 nm and rates of product formation were determined from standard curves prepared by adding varying amounts of 4-hydroxytolbutamide to incubations conducted without NADPH. Preliminary experiments confirmed that 4-hydroxytolbutamide formation by human liver microsomes (30–120 pmol P450) was linear for up to 90 min. Samples were analyzed in triplicate.

(f) Mephenytoin 4'-Hydroxylase Assay

Mephenytoin 4'-hydroxylase activity was measured by a modification of the radiometric HPLC assay described by Shimada et al., J. Biol. Chem. 261:909–921 (1986), as described below. Purified or recombinant yeast microsomes (10–50 pmol) were preincubated with dilauroylphosphatidylcholine (15 μg per 50 pmol P450), P450 reductase (500 U per 50 mol P450), and human cytochrome $b_5$ (2:1 molar ratio when added). The reconstituted mixture was preincubated for 5 min at 37° C., and then placed on ice. A final concentration of 0.4 mM radiolabelled S- or R-mephenytoin (20.7 mCi/mM and 20.9 mCi/mMol) was added to 50 mM HEPES buffer (pH 7.4) containing 0.1 mM EDTA and 1.5 mM $MgCl_2$ for recombinant 2C proteins. The mixture was then incubated at 37° with shaking for 3 min, and the reaction started with the addition of 2mM NADPH and terminated after 30 min with an equal volume of methanol. Cytochrome $b_5$ was not included in all CYP2C18 reactions, since it had no effect or produced a slight inhibition on the activity of this CYP protein. Reaction volumes were generally 0.25 ml except when the volume of recombinant purified cytochrome or yeast microsomes was greater than 50 μl. In these cases, the volume was increased to 0.5 ml to limit the volume of glycerol from the purified preparation to <4% of the final volume. Incubations with human microsomes did not contain exogenous P450 reductase or cytochrome $b_5$, and they were carried out in 0.1M phosphate buffer (pH 7.4) instead of HEPES buffer. Initial experiments shows that S-mephenytoin hydroxylase activity of human liver microsomes was linear for at least 60 minutes and from 0.05 through 0.2 mg microsomal protein, and that of the R-enantiomer was linear through 1 mg microsomal protein.

At the end of the incubation period, the reactions were terminated with an equal volume of methanol. The incubation mixture was centrifuged at 10,000 g for 10 min and an aliquot assayed directly using HPLC without extraction. Samples with particularly low activity were concentrated by lyophilization and redissolved in a small volume of methanol:water (1:1) before assay. The HPLC system consisted of a reverse phase C18 (10 μm) Versapak, 300 mm×4.1 mm column (Altech Associates, Deerfield, Ill.) using an isocratic solvent consisting of methanol:water (45:55) with a flow rate was kept of 1 ml/min for 25 min. Detection of radioactive peaks was accomplished using an on-line Flow-One radiochemical detector (Radiomatic Instruments Co., Tampa, Fla. Detection of the unlabeled 4'-hydroxymephenytoin authentic standard was performed using an on-line multiwavelength UV detector at both 211 and 230 nm.

(g) Statistical analyses

Tolbutamide hydroxylase and mephenytoin hydroxylase activities of microsomes prepared from different recombinant yeasts were compared by analysis of variance and by Fisher's least significant difference test (Carmer et al., *Am. Stat. Ass.* 68:66–74 (1973)).

3. Results (a) Expression of P450 2C cDNAs in yeast

Western blot analysis confirmed the expression of the recombinant human CYP2C proteins in the recombinant yeast (FIG. 6). Antibodies to 2C8 and 2C9 recognized polypeptide bands of approximately 50,000 daltons (2C8) and 55,000 daltons (2C9) which corresponded in mobility to those of the recombinant proteins purified from yeast microsomes. These mobilities corresponded to those of the corresponding 2C8 and 2C9 proteins purified from human liver. 2C19 was recognized by antibodies to both the 2C9 and the 2C19 peptides. This protein corresponded in mobility (<50,000 daltons) to the lowest of three bands in Western blots of human liver microsomes probed with antibody to human 2C9. The mobility of 2C18 was intermediate between that of 2C8 and 2C19. Antibodies to 2C18 and 2C19 peptides were specific for their antigen; however, antibody to 2C9 cross-reacted strongly with 2C19 and weakly with 2C8 and 2C18.

CO difference spectral analysis indicated that the recombinant P450 2C proteins were expressed at levels as high as 160–250 pmol/mg protein in some yeast microsomal preparations. 2C18, 65 (2C9), and 25 (2C9) were expressed at levels of 20 to 60 pmol/mg microsomal protein. Initially, lla (2C19) was expressed extremely poorly, and the CO difference spectrum of the recombinant 2C19 yeast was indistinguishable from that of control yeast (<7 pmol/mg protein). However, after repeated transfections and selection, expression of 2C19 at ~17 pmol/mg protein was achieved. All of the CYP2C proteins were low spin hemoproteins. CYP2C18 appeared to be somewhat unstable in yeast microsomes with a large proportion (~⅓ to ½) of the P450 being converted to P420 in the presence of dithionite and carbon monoxide. None of the other recombinant CYP2C proteins showed this lack of stability.

(b) Optimization of Tolbutamide and S-Mephenytoin Hydroxylase Assays

Figure 7:
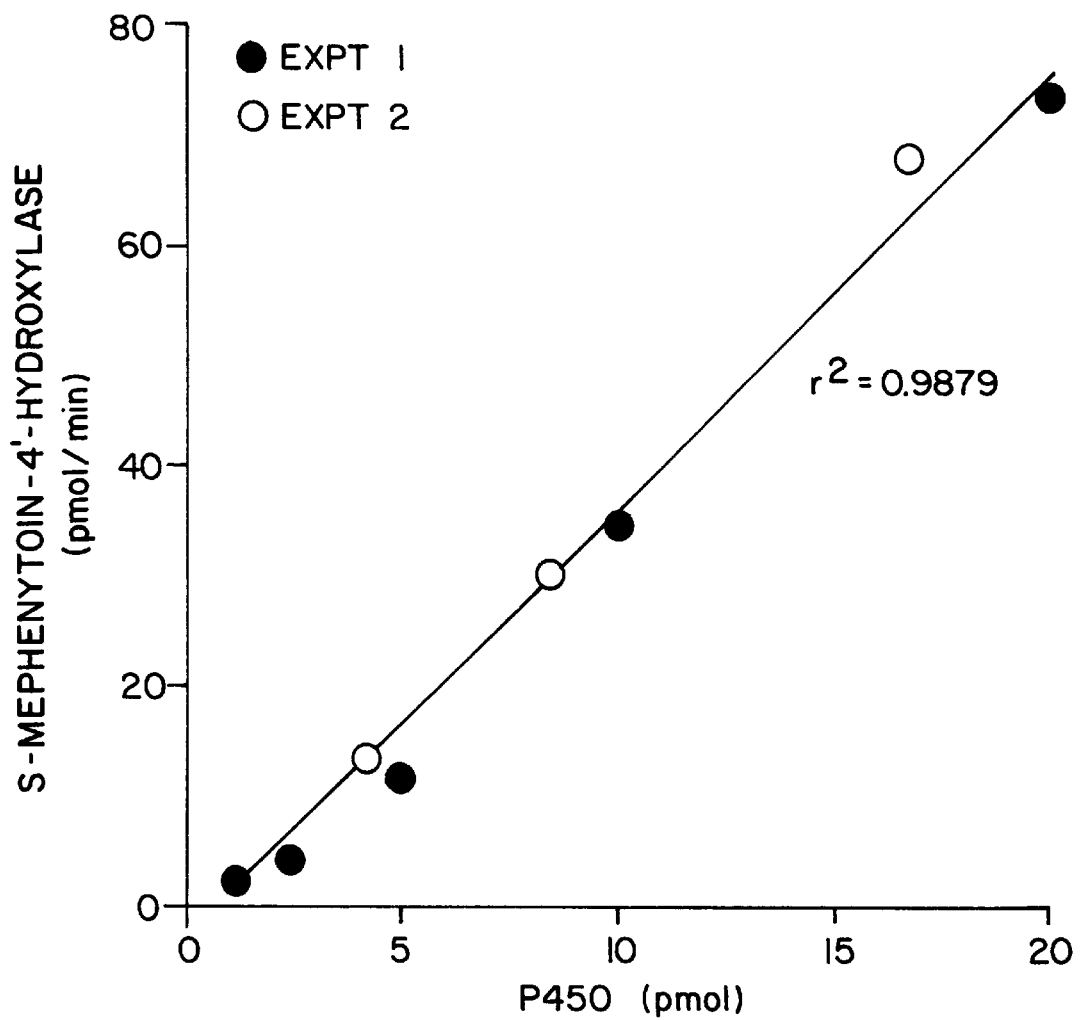
FIG. 7 Linearity of S-mephenytoin 4'-hydroxylase activity and amount of recombinant cytochrome P450 2C19.
Figure 8:
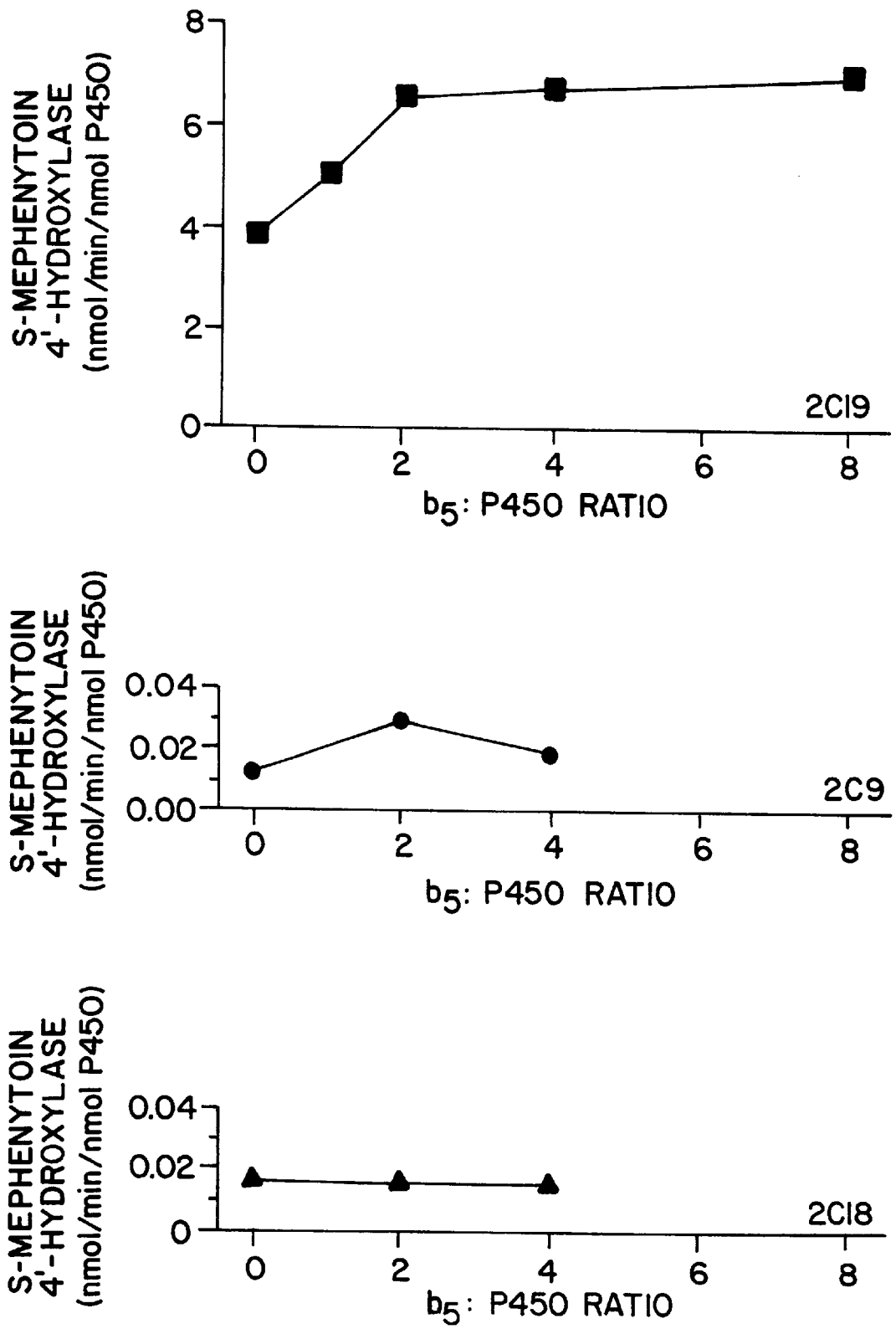
FIG. 8 S-mephenytoin 4'-hydroxylase activity as a function of the molar ratio of cytochrome $b_5$ to recombinant cytochrome P450.

Preliminary studies indicated that exogenous P450 reductase (500 U/50 pmol P450) stimulated metabolism of tolbutamide by recombinant 2C9 in yeast microsomies >10-fold and stimulated S-mephenytoin hydroxylase activity approximately 2-fold. Activity of the recombinant 2C proteins was linear with amount of P450 for 30 minutes through at least 20 pmol P450 for 2C19 (FIG. 7) and 50 pmol for the other CYP2C forms. Cytochrome bs stimulated S-mephenytoin hydroxylase activity of both 2C9 and 2C19 in yeast microsomes and the optimal ratio of $b_5$ to P450 was approximately 2:1, but it generally had no effect or produced a slight inhibition of mephenytoin hydroxylase activity of 2C18 (FIG. 8). This difference is consistent with the fact that all of the CYP2C proteins except 2C18 contain a Ser at position 128 which is a recognition site for CAMP protein kinase ($^{125}$Arg-Arg-Phe-Ser$^{128}$) (Müller et al., *FEBS Lett.* 187:21–24 (1985), and this sequence is also thought to be part of a $b_5$ binding site (Jansson et al., *Arch. Biochem. Biophys.* 259:441–448 (1987); 2C18 contains Cys at position 125.

Mephenytoin 4'-hydroxylase activity of recombinant yeast microsomes was consistently higher in HEPES than phosphate buffer, while activity of human liver microsomes was ~2-fold higher in phosphate buffer (pH 7.4). Therefore, recombinant proteins were subsequently assayed in HEPES buffer with exogenous reductase and cytochrome $b_5$ except for 2C18 which was tested both with and without cytochrome $b_5$. Human liver microsomal activities were assayed in phosphate buffer.

(c) Mephenytoin hydroxylase activity of recombinant human 2C proteins

Figure 9:
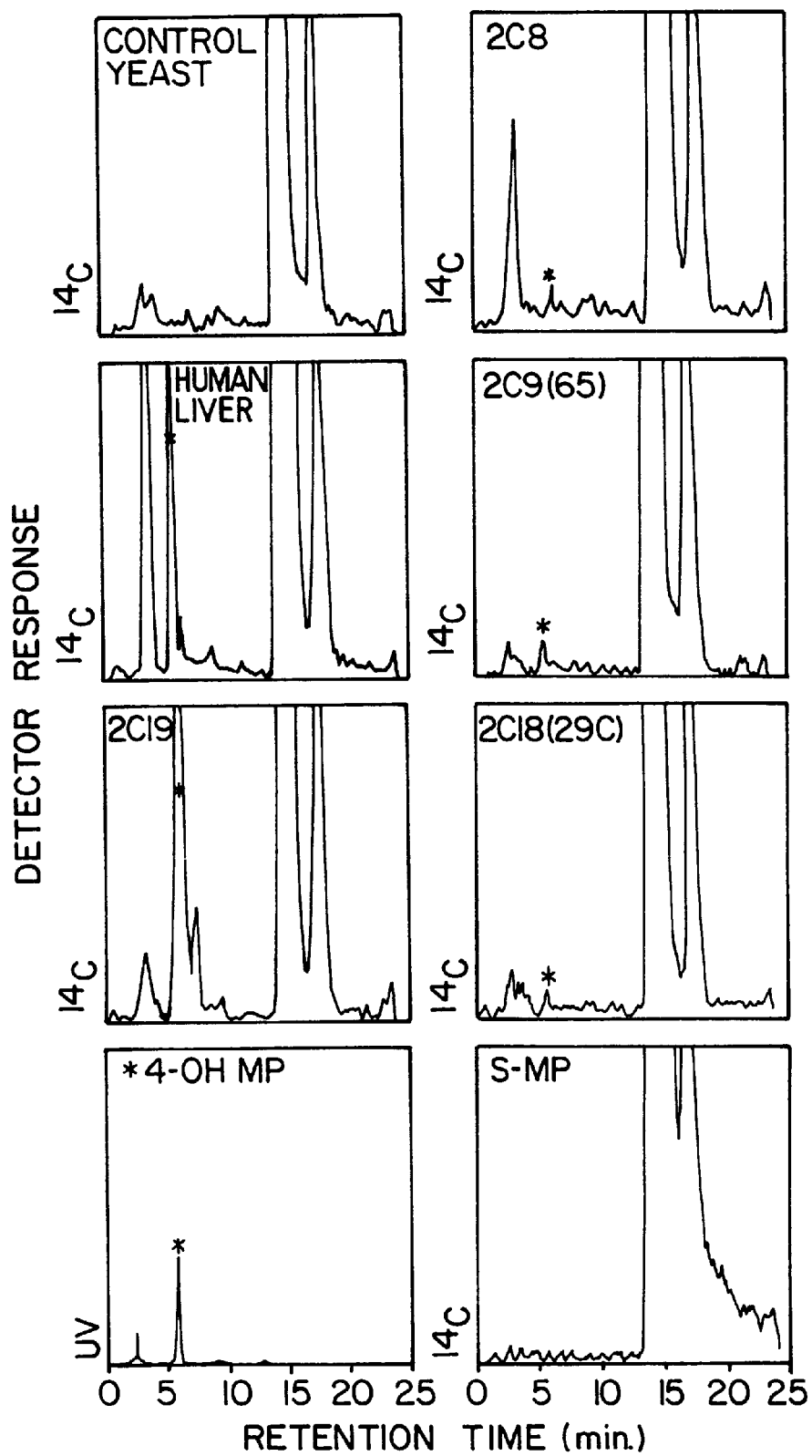
FIG. 9 HPLC radiochromatograms of metabolites formed after incubation of labelled mephenytoin with P450 2C enzymes, human liver microsomes and yeast control.

S-mephenytoin 4'-hydroxylase activities of yeast microsomes containing recombinant human CYP2C proteins were compared under optimized conditions described above. HPCL profiles of the metabolites of S-mephenytoin produced by human liver microsomes and recombinant human CYP2C proteins are shown in FIG. 9 and the results summarized in Table III. Recombinant 2C19 4'-hydroxylated S-mephenytoin at a rate of ~5 nmol/min/nmol P450 which was an order of one magnitude higher than the rate of 4'-hydroxylation in human liver microsomes (Table III and FIG. 9). The retention time (5–6 min) of the 4'-hydroxymephenytoin metabolite was identical to that of the authentic unlabeled standard. 2C19 also produced small quantities of two unknown metabolites eluted at 3–4 and 7–8 min. These unknown metabolites were also produced by liver microsomes, and the metabolite with the shorter retention time was the principal metabolite produced by 2C8. Parent S-mephenytoin eluted at 14–15 min. followed by the unknown impurity which eluted at 16–17 min. Similar retention times were observed for R-mephenytoin and its metabolites.

The rate of 4'-hydroxymephenytoin formation by 2C19 was at least 100-fold higher than that of 2C9 (both alleles), 2C18 (both alleles) and 2C8 (Table III). The rate of 4'-hydroxylation of S-mephenytoin by 2C8 appeared to be lower than that of 2C9 (0.02 nmol/min/nmol). The 4'-hydroxylation of mephenytoin by 2C19 was stereospecific; the rate of S-hydroxylation was at least 30-fold higher than that of R-hydroxylation (Table III). In contrast, the 4'-hydroxylation of mephenytoin by the other human CYP2C proteins did not appear to be stereospecific.

TABLE III

S-Mephenytoin 4'-Hydroxylase Activities in
Recombinant Human CYP2C Yeast Microsomes

| | Mephenytoin 4'-Hydroxylase Activity nmol/min/nmol P450 | | R/S |
|---|---|---|---|
| Microsomes | S | R | Ratio |
| Controls | 0.028 ± 0.001 | 0.024 ± 0.003 | 0.9 |
| 2C9-Ile$^{359}$ (65) | 0.043 ± 0.000 | 0.041 ± 0.005 | 0.9 |
| 2C9-Leu$^{359}$ (25) | 0.031 ± 0.009 | 0.040 ± 0.01 | 1.3 |
| 2C8 | 0.037 ± 0.001 | 0.016 ± 0.001 | 0.4 |
| 2C18-Thr$^{385}$ (29c) + b5 | 0.042 ± 0.004 | 0.054 ± 0.003$^a$ | 1.3 |
| 2C18-Thr$^{385}$ (29c), no b5 | 0.034 ± 0.008 | — | |
| 2C18-Met$^{385}$ (6b) | 0.023 ± 0.004 | 0.019 ± 0.005 | 0.9 |
| 2C19 (11a) | 4.6 ± 0.3$^{a,b,d}$ | 0.014 ± 0.02$^a$ | 0.03 |
| Human liver microsomes HB1 6 | 0.283 ± 0.037$^{a,c,d}$ | 0.117 ± 0.017$^{a,c}$ | 0.4 |

TABLE III-continued

S-Mephenytoin 4'-Hydroxylase Activities in
Recombinant Human CYP2C Yeast Microsomes

| | Mephenytoin 4'-Hydroxylase Activity nmol/min/nmol P450 | | R/S |
|---|---|---|---|
| Microsomes | S | R | Ratio |

S-Mephenytoin hydroxylase assayed as described in Methods. Reaction mixtures contained 10 pmol of recombinant CYP2C19 or 50 pmol of other recombinant CYP2C yeast microsomes, 500 U of purified P450 reductase and 15 μg phospholipid per 50 pmol of P450, and 0.4 mM radioactive substrate in 0.1M HEPES buffer (pH 7.4). Unless otherwise stated recombinant yeast microsomes were also reconstituted with a 2:1 molar ratio of cytochrome $b_5$. Reactions were incubated at 37° C. for 30 min with 1 mM NADPH. Control reactions contained the same reaction mixture and were incubated similarly with an equivalent amount of control yeast microsomal protein (1 mg). Specific content of P450 of the recombinant yeast microsomes ranged from 35–48 pmol/mg except for 2C8 (191 pmol/mg) and 2C19 (17 pmol/mg). Control liver reactions contained 0.1 mg microsomal protein but were not fortified with reductase, cytochrome $b_5$, or phospholipid and were incubated with 0.1M phosphate buffer (pH 7.4). Values represent the means ± SE.
$^a$Activity significantly higher than that of control yeast microsomes, $P < 0.05$. Analysis of variance and Fisher's Least Significant difference test.
$^b$2C19 activity significantly higher than activities of all other recombinant CYP2C proteins or human liver microsomes, $P < 0.05$.
$^c$Human liver microsomes significantly higher than recombinant microsomes except 2C19, $P < 0.05$.
$^d$Significant difference between S- and R-Mephenytoin hydroxylase activities, $P < 0.05$.

TABLE IV

Mephenytoin 4'-Hydroxylase and Tolbutamide Hydroxylase Activities
of Purified Recombinant Human P450s from the 2C Subfamily

| P450 2C (clone) | Mephenytoin 4'-Hydroxylase Activity (nmol/min/nmol P450) | | R/S Ratio | Tolbutamide Hydroxylase Activity (pmol/min/nmol P450) |
|---|---|---|---|---|
| | S | R | | |
| 2C19 | 6.17 ± 0.24$^{a,b,c}$ | 0.19 ± 0.04$^a$ | 0.03 | ND |
| 2C9-Ile$^{359}$ (65) | 0.081 ± 0.006$^a$ | 0.063 ± 0.003$^a$ | 0.77 | 122 + 29$^{a,d}$ |
| 2C9-Leu$^{359}$ (25) | ND | ND | | 10 + 2 |
| 2C18-Asp$^2$Thr$^{385}$ (29c-1a) | 0.116 ± 0.010$^a$ | 0.147 ± 0.025$^a$ | 1.3 | ND |
| 2C18-Val$^2$Thr$^{385}$ (29c) | 0.019 ± 0.001 | 0.073 ± 0.009$^{a,c}$ | 2.7 | 102 ± 2$^{a,d}$ |
| 2C18-Asp$^2$Met$^{385}$ (6b) | 0.103 ± 0.016$^a$ | 0.107 ± 0.005$^c$ | 1.0 | ND |
| 2C8 | 0.057 ± 0.009$^{a,c}$ | 0.023 ± 0.004 | 0.4 | 12 ± 4 |
| 2C8 Purified from Human Liver | 0.032 ± 0.003 | 0.051 ± 0.030 | 1.6 | ND |
| 2C9 Purified from Human Liver | 0.033 ± 0.001 | 0.051 ± 0.007$^{a,c}$ | 1.6 | 109 ± 16 (390, 2,840)$^{a,d,e}$ |
| Human Liver Microsomes HB16 | 0.46 ± 0.02$^a$ | 0.28 ± 0.01 | 0.6 | ND |
| Human Liver Microsomes UC8936 | — | — | | 408 ± 21 |

Recombinant P450s were purified from yeast microsomes and assays performed as described in Methods. 2C9 were purified from human liver (Raucy and Lasker, 1991). Assays were performed in triplicate and values represent means ± SE. Blank reactions (containing all components except the P450) were subtracted (22 ± 5) from tolbutamide hydroxylase values. Blank reactions for the S-mephenytoin assay were not subtracted since no distinct peaks with the exact retention times of 4'-hydroxymephenytoin were observed; however, background radioactivity was in the range of ⁻0.025 ± 0.01 nmol/min/nmol. ND = Not determined.
$^a$Increased over blank values, $P < 0.05$
$^b$S-Mephenytoin hydroxylase activity of 2C19 significantly greater than all other values, $P < 0.05$
$^c$S-Mephenytoin hydroxylase activity of significantly different from R-mephenytoin values, $P < 0.05$.
$^d$Tolbutamide hydroxylase activity of 65 and 29c were significantly greater than 25, or 2C8 ($P < 0.0001$).
$^e$Tolbutamide hydroxylase activity of two other 2C9 preparations derived from different human livers in parentheses.

Recombinant CYP2C proteins were purified from yeast microsomes and their ability to 4'-hydroxylate the S- and R-enantiomers of mephenytoin were also examined in a reconstituted system (Table IV). 2C19 had similar turnover numbers for S-mephenytoin 4'-hydroxylation in the reconstituted system and in recombinant yeast microsomes fortified with reductase. This turnover number was at least 10-times higher than that of human liver microsomes, and it was 50–100 times higher than that of recombinant 2C9, 2C18 or 2C8. The turnover number of recombinant 2C9 was ~100 times higher than the activity of a preparation of 2C9 purified from human liver. 4'-hydroxylation of mephenytoin by 2C19 was stereospecific for the S-enantiomer, while metabolism by 2C9 was not stereospecific. Surprisingly, 2C18 appeared to be stereoselective for the R-enantiomer of mephenytoin. The turnover number of 2C19 for S-mephenytoin 4'-hydroxylase was also ~30 times higher than the turnover numbers reported for a preparation P450$_{MP}$ purified from human liver by Srivastava et al., *Mol. Pharmacol.* 40:69–79 (1991) (0.21 nmol/min/nmol P450).

Although 2C9 exhibits poor catalytic activity toward S-mephenytoin, this cytochrome appears to be the principal tolbutamide hydroxylase (Table IV and V). The turnover numbers for hydroxylation of tolbutamide by the purified recombinant 2C9 were somewhat lower than those of 2C9 purified form human liver in the absence of exogenous reductase. The Ile$^{359}$ allele of 2C9 had a 3-fold higher turnover number for tolbutamide than the Leu$^{359}$ allele when activity of the recombinant microsomes were adjusted for P450 content (Table V). 2C19 also appeared to metabolize tolbutamide at a rate comparable to that of 2C9, although this rate was difficult to estimate due to the low specific content of P450 in the recombinant 2C19 yeast clone available at the time of these assays. The two alleles of 2C18 exhibited lower tolbutamide hydroxylase activity than 2C9 in recombinant yeast microsomes.

number appreciably higher than that of human liver microsomes. Other 2C proteins showed a 100-fold reduced activity relative to 2C19. One of the 2C9 variants tested (Ile$^{359}$) is identical to that reported by Yasumori et al., supra to show a low level of S-mephenytoin 4'-hydroxylase activity. The low rate of 4'-hydroxylation of S-mephenytoin by 2C9 detected in the present study with high specific activity $^{14}$C-labeled S-mephenytoin undoubtedly explains the conflicting reports from various laboratories concerning the ability of this cytochrome to metabolize mephenytoin (Yasumori et al., supra; Srivastava et al., supra; Relling et al., supra).

(d) Comparisons of Immunoblot Analysis of CYP2C Proteins in Human Livers with Liver Microsomal S-Mephenytoin 4'-Hydroxylase Activities Microsomes from 16 human liver donor samples previously assayed for S- and R-mephenytoin 4'-hydroxylase activities were analyzed for CYP2C proteins by Western blot analysis (FIG. 10) using an antibody to 2C8 and a polyclonal antibody to 2C9 and 2C19. Both 2C18 and 2C19 have mobilities similar to that of the low molecular weight band recognized in human microsomes by most antibodies to 2C9. However, an antibody to a 2C19 peptide was specific for 2C19. 2C18 could not be detected in human liver samples using a peptide antibody to 2C18 (~5 pmol detection limit), indicating that this polypeptide is expressed poorly (<50 pmol/mg).

Figures 1, 10:
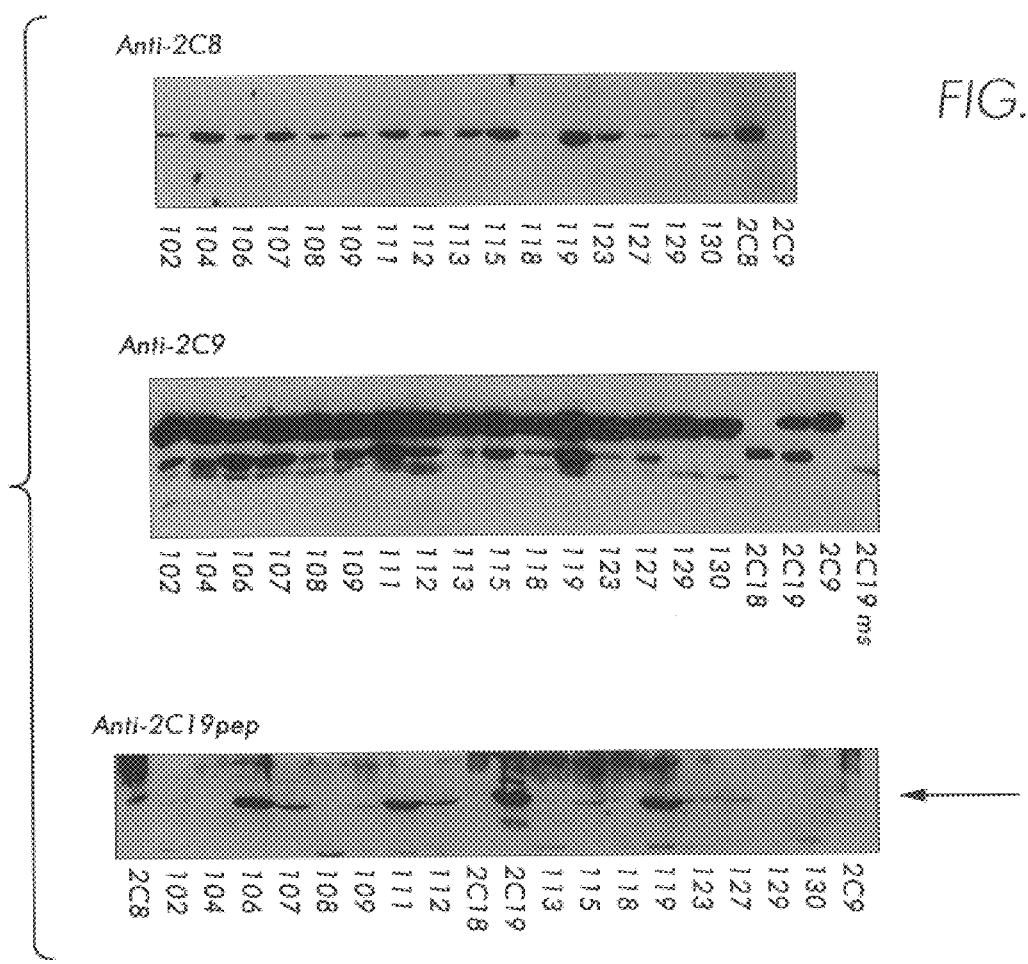
FIG. 1 shows Western blots of human liver microsomal proteins. Microsomal proteins were separated by SDS-polyacrylamide gel electrophoresis. Blot A was performed using polyclonal antibody to 2C9 and blot B with anti-2C8 (HLx). Each lane represents 20 µg of microsomal protein from an individual liver. The 2C8 antibody also recognized purified rat P450 2C13(g). cDNA libraries were constructed from livers 860624 (low HLx) and S33 (high HLx).
FIG. 10 Comparison of liver content of cytochrome P450 2C enzymes with S-mephenytoin 4'-hydroxylase activity. The upper part of the figure shows Western blots of liver samples from 16 individuals. The lower part of the figure shows the S-mephenytoin 4'-hydroxylation activity and ratios of S/R mephenytoin 4'-hydroxylase activity in each sample.
Figures 2, 10:
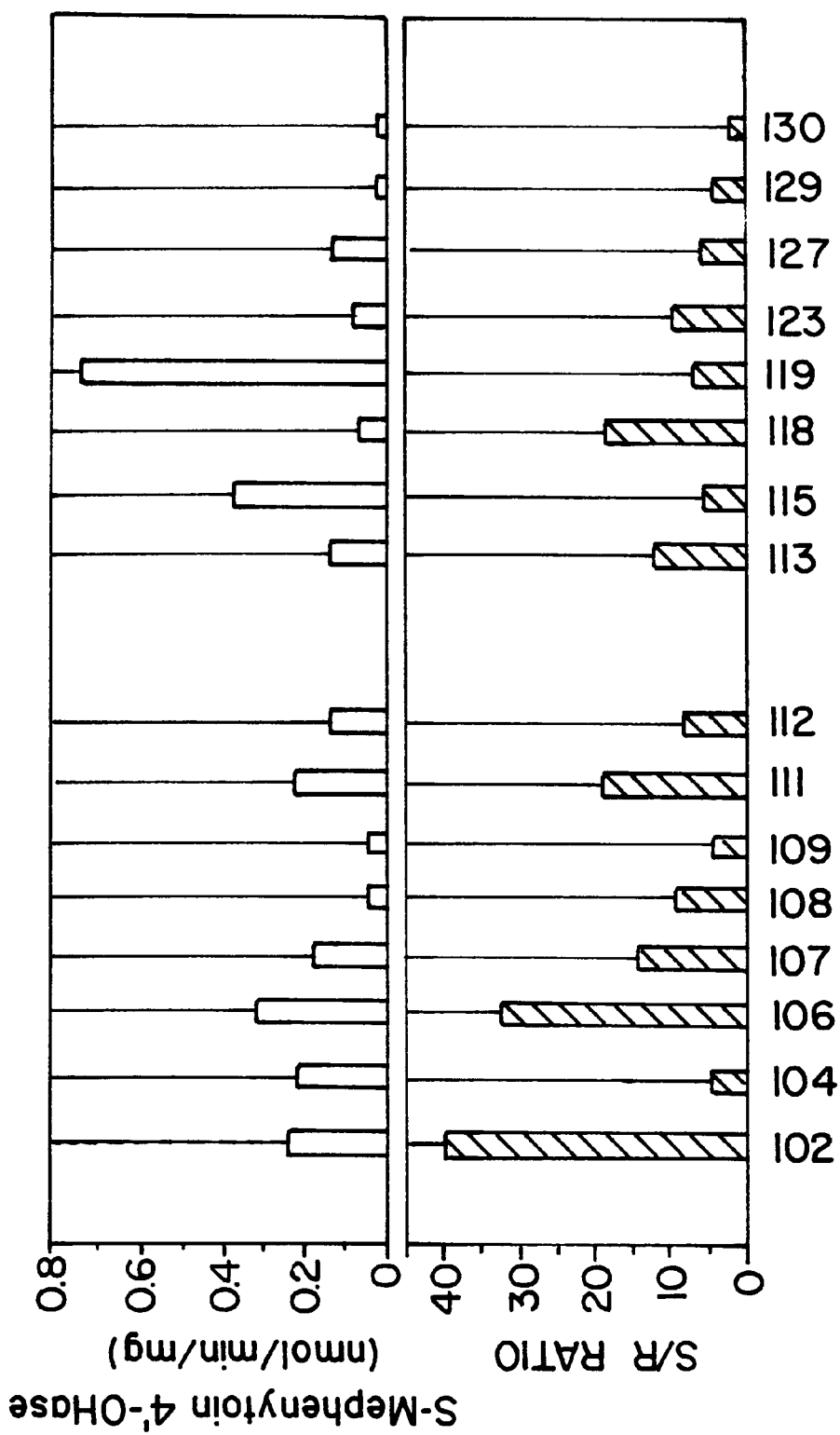
FIG. 2 contains nucleotide sequences of human P450 2C cDNAs. 2c (SEQ. ID. No. 14) is indicated in the top line and represents the consensus sequence where information from more than one sequence is available. Sequences were determined by the dideoxy chain termination method. The differences observed for clones 25 (SEQ. ID. No. 4) and 65 (SEQ. ID. No. 10) are underlined. The termination codons are starred. The heme binding region and polyadenylation signals are underlined. The one-base difference between 29c (SEQ. ID. No. 6) and 6b (SEQ. ID. No. 12) are also underlined. The termination codon is starred. The new allelic variant proteins of 2C18, referred to as 29c (SEQ. ID. No. 5) and 6b (SEQ. ID. No. 11), and the new protein of 2C19, referred to as 11a (SEQ. ID. No. 1), are compared with the protein of 2C8, referred to as 2C8 (SEQ. ID. No. 7), and the allelic variant proteins of 2C9, referred to as 65 (SEQ. ID. No. 9) and 25 (SEQ. ID. No. 3).
Figure 11:
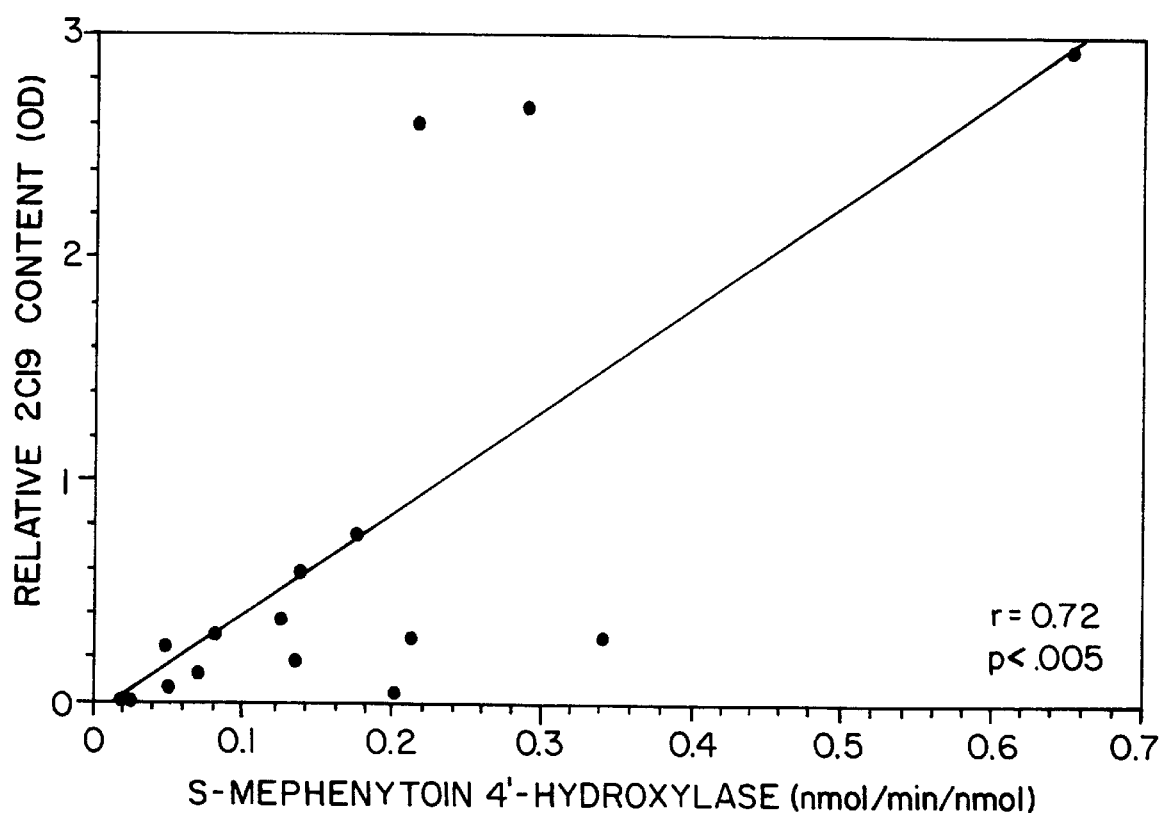
FIG. 11 Correlation between hepatic 2C19 content and S-mephenytoin hydroxylase activity based on the data shown in FIG. 10.

The 2C19 content of liver microsomes was consistent with their S-mephenytoin 4'-hydroxylase activities (FIG. 10). In particular, samples 129 and 130 had extremely low S-mephenytoin 4'-hydroxylase values, low S/R ratios, and 2C19 appeared to be essentially absent in these microsomal samples. Densitometric analysis of immunoblots revealed that 2C19 content of the 16 human liver microsomes correlated significantly with S-mephenytoin 4'-hydroxylase activity ($r=0.718$, $P<0.005$) (FIG. 11), but that the content of

TABLE V

Tolbutamide Hydroxylase Activities of
Recombinant Human CYP2C Yeast Microsomes

| Microsomes | P450 Content (pmol/mg) | Tolbutamide Hydroxylase Activity (nmol/min/mg protein) | (nmol/min/nmol P450) |
|---|---|---|---|
| Control Yeast | <5 | 0.3 ± 0.01 | — |
| 2C9-Ile$^{359}$ (65) | 55 | 169.8 ± 7.4$^{a,b}$ | 3.4 ± 0.15 |
| 2C9-Leu$^{359}$ (25) | 20 | 14.8 ± 0.3$^{a,c}$ | 0.99 ± 0.02 |
| 2C8 | 80 | 8.5 ± 0.2$^a$ | 0.11 ± 0.003 |
| 2C18-Asp$^2$Thr$^{385}$ (29c-1a) | 53 | 9.3 ± 0.7$^a$ | 0.19 ± 0.02 |
| 2C18-Asp$^2$Met$^{385}$ (6b-9) | 34 | 11.1 ± 1.2$^a$ | 0.37 ± 0.04 |
| 2C19 (11a-3) | <7 | 18.4 ± 2.4$^{a,d}$ | ND |
| UC8936 Human Liver Microsomes | 227 | 116 ± 0.8$^a$ | 2.3 ± 0.02 |

Tolbutamide hydroxylase activities measured as described in methods. Reaction mixtures contained 1 mg yeast microsomal protein or 0.2 mg UC8936 human liver microsomal protein (50 pmol P450). Purified P450 reductase (1,000 units) was included in reactions with yeast microsomes but not human microsomes. Values were the means ±SE.
ND = Not calculated due to low specific content of 2C19 in yeast in this experiment.
$^a$Significantly higher than control yeast microsomes, P < 0.05. Pairwise comparisons using Fisher's Least Significant Difference test.
$^b$Clone 65 significantly higher than all other clones (P < 0.0001).
$^c$Clone 25 significantly greater than 2C8 (P < 0.0005).
$^d$Clone 11a significantly higher than 2C8 (P < 0.0001).

The data show that CYP2C19 stereospecifically hydroxylates S-mephenytoin at the 4'- position at a rate which is at least 10 times higher than the rate in human liver microsomes. This is the first example of a human CYP protein which metabolizes S-mephenytoin with a turnover 2C9 did not correlate with this catalytic activity ($r=0.49$, $P>0.05$). There was also a significant correlation between 2C8 content and S-mephenytoin 4'-hydroxylase activity ($r=0.82$, $P<0.0001$). However, this correlation was probably fortuitous, because 2C8 shows very low S-mephenytoin 4'-hydroxylase activity either in recombinant form or when purified from human liver. Alternatively, the correlation may indicate an indirect regulatory role for 2C8 in controlling S-mephenytoin 4'-hydroxylase activity.

(e) Sequences of 2C9 and 2C18 mRNAs in Livers with High or Low S-mephenytoin 4'-Hydroxylase Activities 2C18 and 2C9 mRNAs from six of the above livers were amplified by PCR and directly sequenced through areas of known allelic variation to determine whether there was a relationship between S-mephenytoin 4'-hydroxylase activity and the presence of a particular allelic variant (Table VI). When the total 2C18 PCR products were sequenced, the two individuals with the highest S-mephenytoin hydroxylase activity were homozygous for $Thr^{385}$(ACG). Of the two individuals with the lowest activity, one was homozygous for $Met^{385}$, and one was heterozygous for Thr/$Met^{385}$(AC/TG). Two individuals with intermediate activity were also homozygous for $Thr^{385}$. Similarly, when 2C9 mRNA from these same individuals was amplified and sequenced through known allelic variations, sample 108 (low S-mephenytoin 4'-hydroxylase activity) was heterozygous at C/$T^{430}$ (coding for Cys/$Arg^{144}$), while the other five individuals were homozygous for $C^{430}$ ($Arg^{144}$). Sequencing samples through bases 1072–1077, all samples except for 106 (high activity) read $^{1072}TACATT^{1077}$, coding for $Tyr^{358}Ile^{359}$. Sample 106 read TACA/CTT indicating that it was heterozygous for Ile/$Leu^{359}$. These data indicate that there is no relationship between S-mephenytoin 4'-hydroxylase activity of human liver microsomes and the identity of the allelic variants of 2C18 (Thr/$Met^{385}$) or 2C9 (Arg/$Cys^{144}$, Tyr/$Cys^{358}$, Ile/$Leu^{359}$) in these tissues.

(a) Analysis of full-length cDNA

Liver microsomes were prepared by standard differential centrifugation methods (2) from human liver samples previously characterized as varying markedly in S-mephenytoin 4'-hydroxylase in vitro. Total liver RNA was isolated from the liver samples with trireagent (Molecular Research Center, Inc.) and reversed transcribed using random hexamers as 3' primers. Overlapping CYP2C19 cDNA fragments from five human liver samples that showed poor metabolism of S-mephenytoin in vitro were amplified by the polymerase chain reaction (PCR). PCR was performed on an aliquot of the cDNA in 1× PCR buffer (67 mM Tris-HCl pH 8.8, 17 mM $(NH_4)_2SO_4$, 10 mM β-mercaptoethanol, 7 μM EDTA, 0.2 mg bovine serum albumin/ml), 50 μM dATP, dCTP, dGTP and dTTP, 0.25 μM of both PCR primers, 2.5 U AmpliTaq DNA polymerase (Perkin Elmer Cetus) and 1.0 mM $MgCl_2$. The PCR conditions were: initial denaturation at 94° C. for 3 min; 35 cycles consisting of: denaturation at 94° C. for 30 sec, annealing at 53° C. for 30 sec and extension at 72° C. for 30 sec; final extension at 72° C. for 10 min; using a Perkin Elmer thermocycler. PCR products (20 μl) were analyzed on 3% agarose gels stained with ethidium bromide.

The PCR fragments were purified using Microcon filters (Amicon Inc.) and used in the cycle sequencing reaction employing fluorescence-tagged dye terminators (PRISM, Applied Biosystems)ed and sequenced. One partial CYP2C19 cDNA was isolated which exhibited aberrant splicing of exon 5 (FIG. 12). This cDNA was missing the initial 40 bases of exon 5, and was also missing a SmaI site (FIG. 12). This deletion would be predicted to produce an early stop codon resulting in a truncated defective protein.

TABLE VI

Alleles in Human Livers with Varying S-Mephenytoin 4'-Hydroxylase Phenotypes

| Pheno-type | S-MPOHase nmol/min/mg | Liver donor | 2C18 allele | | 2C9 allele | | | |
|---|---|---|---|---|---|---|---|---|
| High | 0.286 | 106 | $Thr^{385}$ | | $Arg^{144}$ | $His^{276}$ | $Tyr^{358}$ | Ile/$Leu^{359}$ |
| High | 0.351 | 115 | $Thr^{385}$ | | $Arg^{144}$ | $His^{276}$ | $Tyr^{358}$ | $Ile^{359}$ |
| Intermediate | 0.070 | 118 | $Thr^{385}$ | | $Arg^{144}$ | $His^{276}$ | $Tyr^{358}$ | $Leu^{359}$ |
| Intermediate | 0.081 | 123 | $Thr^{385}$ | | $Arg^{144}$ | $His^{276}$ | $Tyr^{358}$ | $Ile^{359}$ |
| Low | 0.051 | 108 | Thr/$Met^{385}$ | | Arg/$Cys^{144}$ | $His^{276}$ | $Tyr^{358}$ | $Ile^{359}$ |
| Low | 0.025 | 129 | Met/$Met^{385}$ | | $Arg^{144}$ | $His^{276}$ | $Tyr^{358}$ | $Ile^{359}$ |

4. Conclusion

These results show that 2C19 has a turnover number for the 4'-hydroxylation of S-mephenytoin about 100-fold higher than that of 2C9, 2C18, or 2C8. 2C19 hydroxylation was stereospecific for the S- enantiomer. The hepatic content of 2C19 in 16 liver microsomal samples correlated with their S-mephenytoin 4'-hydroxylase activities. 2C9 appeared to be the primary tolbutamide hydroxylase, although 2C19 may also contribute to this catalytic activity. The identity of the allelic variant of 2C9 or 2C18 did not influence S-mephenytoin 4'-hydroxylase activity. These data strongly indicate that 2C19 is the key determinant of S-mephenytoin 4'-hydroxylase activity in human liver.

Example 6
Diagnostic Assays for Detecting Individuals Deficient in S-Mephenytoin 4'-Hydroxylase Activity Individuals deficient in S-mephenytoin 4'-hydroxylase activity are identified by comparing analysis of their genomic or cDNA encoding 2C19.

(b) Rapid Assay for Identifying 40 bp Deletion in cDNA

The analysis of full-length cDNAs identified a 40 bp deletion as a likely cause of S-mephenytoin 4'-hydroxylase activity deficiency. A rapid assay was therefore devised to analyze the specific region of a 2C19 cDNA molecule spanning the 40 bp deletion.

Specific PCR primers were designed to amplify the region of the CYP2C19 cDNA spanning the deletion (FIGS. 12 and 13). mRNA from 13 human livers previously characterized for extensive or poor metabolism of S-mephenytoin in vitro were reverse transcribed and amplified by PCR. Liver samples with the highest S-mephenytoin hydroxylase activity contained only the normally spliced mRNA. By contrast, sample 35 (a probable poor metabolizer) produced an amplification product containing the 40 bp deletion. Samples with intermediate S-mephenytoin 4'-hydroxylase activity and low amounts of CYP2C19 protein exhibited both the normal 2C19 cDNA and 2C19 cDNA containing the 40 bp deletion.

(c) Genomic Sequencing of 2C19

Because human tissue samples containing genomic 2C19 DNA are much more easily obtained than samples containing 2C19 mRNA, it is preferable to diagnose a polymorphic defect from genomic DNA. Genomic DNA was isolated from the blood of human volunteers previously characterized as poor or extensive metabolizers of S-mephenytoin in vivo. The in vivo phenotype of most Swiss subjects was based on a hydroxylation index, with a value above 5.6 identifying a poor metabolizer (Kupfer et al., Eur. J. Clin. Pharmacol. 26:753–759 (1984)). The in vivo phenotype of American, Oriental and one Swiss subject was based on the urinary S/R ratio (Wedlund et al., Clin. Pharmacol. Ther. 36:773–780 (1984))—a poor metabolizer (PM) being defined as having a ratio >0.95. An extensive metabolizer is defined as having a ratio <0.8. An intermediate phenotype (IM) has been previously described with the extent of 4'-hydroxylation being greater than in PMS but with the rate of metabolite formation being slower than EMS (Arns et al., Pharmacologist 32:140 (1990)).

It was believed that the 40 bp deletion identified in 2C19 cDNA occurred in exon 5, near the border with intron 4 based on a comparison of the gene structure of CYP2C9 and CYP2C18 (de Morais et al., supra). Thus, a segment of genomic 2C19 DNA across the intron 4/exon 5 border was amplified to identify the corresponding genetic defect in genomic DNA. In the initial assays, the untranslated regions of the genomic 2C19 sequence were not known. However, intron 4 primers could be designed based on the corresponding sequences from CYP2C9, which are expected to show about 95% sequence identity based on comparison with partial genomic sequences of 2C19. The primer for exon 5 was based on the cDNA sequence of CYP2C19 (see Example 1). The amplified DNA fragment was found to have the same size in both poor and extensive metabolizers. However, on restriction analysis, it was found that only the fragment from extensive metabolizers could be digested with SmaI. The amplified DNA fragment was sequenced in extensive and poor metabolizers.

Provision of genomic 2C19 DNA sequence in the intron 4 region, allowed the design of a specific intron primer exhibiting perfect complementarity to the 2C19 DNA sequence in subsequent experiments. The forward PCR primer from intron 4 was 5'-AATTACAACCAGAGCTTGGC-3' and the reverse primer from exon 5 was 5'-TATCACTTTCCATAAAAGCAAG-3'. The forward primer anneals 81 bp upstream of the intron 4/exon 5 junction. PCR conditions were as for amplification of cDNA except that reactions used 200 ng of genomic DNA and an initial denaturation at 96° C. for 5 min. PCR products were restricted with SmaI in the PCR buffer, without purification. Uncut products had the same size (168 bp) in all samples. Digested PCR products were analyzed on 4% agarose gels stained with ethidium bromide.

Figures 14C, 14D:
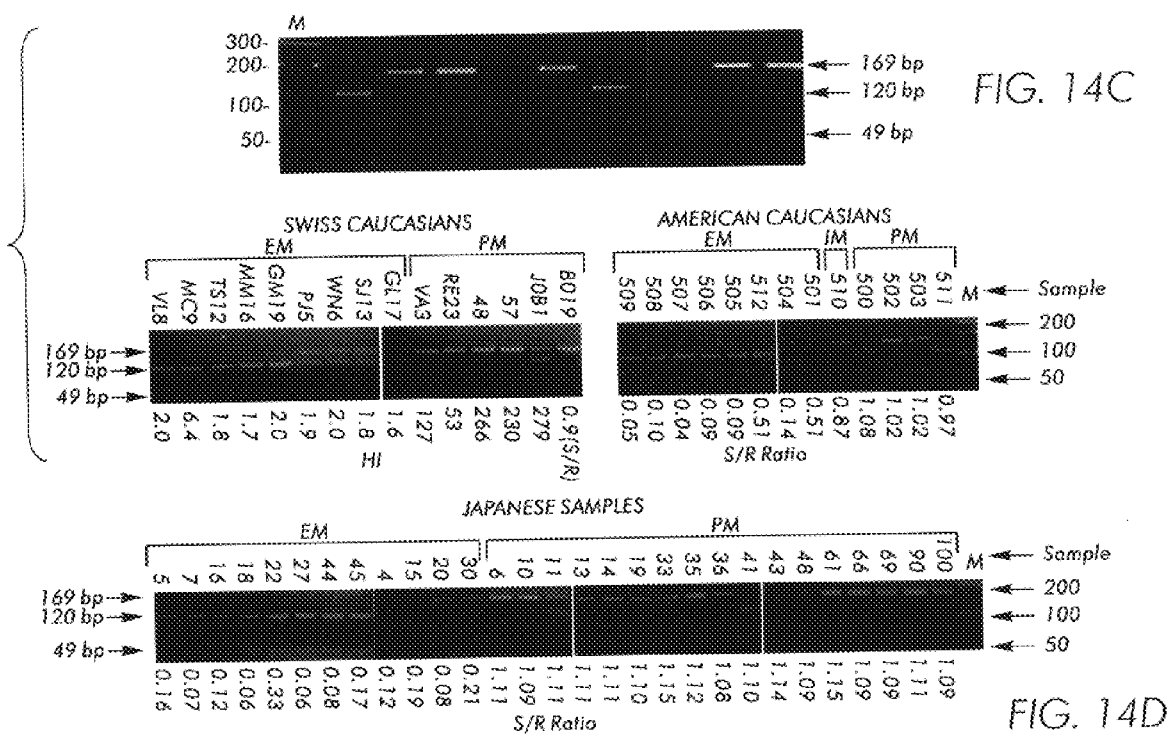
FIG. 14(A–D) A. Diagram showing strategy used to genotype genomic DNA from human blood. B. Diagram of family of propositus 61 (arrow) showing the pedigree and the gel of SmaI-digested PCR products. C. Analysis of genomic DNA from selected Caucasians subjects from United States or from Switzerland. The phenotype (EM, IM or PM) is indicated in the brackets above the gel. D. Analysis of genomic DNA from selected Oriental subjects.

DNA from 18 unrelated Caucasian extensive metabolizers and 10 unrelated Caucasian poor metabolizers was analyzed by this strategy. (FIG. 14C). All extensive metabolizers were either homozygous or heterozygous for the normal CYP2C19 gene, defined here as CYP2C19$_{wt}$(wild type). Among the 10 poor metabolizers, 7 were homozygous for the defective gene, defined as CYP2C19$_m$(poor mephenytoin hydroxylation). One poor metabolizer was heterozygous (CYP2C19$_{wt}$/CYP2C19$_m$), and two were homozygous (CYP2C19$_{wt}$/CYP2C19$_{wt}$), indicating that CYP2C19$_m$ accounted for 15 of 20 alleles tested (75%) in Caucasian poor metabolizers. The presence of 5 CYP2C19$_{wt}$ alleles in poor metabolizers suggests that additional mutations may exist in the Caucasian population, but that 2C19$_m$ represents the predominant defect.

Segments of DNA spanning the intron 4/exon 5 boundary were also amplified from 17 unrelated Oriental subjects. FIG. 14D shows that 10/17 Oriental poor metabolizers are homozygous for CYP2C19$_m$ and CYP2C19$_m$ accounts for 25 of 34 alleles (74%) in Oriental poor metabolizers. All 12 unrelated Oriental extensive metabolizers were either homozygous or heterozygous for the CYP2C19$_{wt}$ gene. Thus, the major mutation responsible for the poor metabolizer phenotype in Oriental is identical to that found in Caucasians.

The inheritance of CYP2C19$_m$ in one Oriental family previously characterized with respect to the PM trait was also examined. FIG. 14B shows that the poor metabolizer proband (arrow) and two other related poor metabolizers are homozygous for CYP2C19$_m$. Two individuals identified earlier as obligate heterozygotes (family C) (Ward et al., Clin. Pharmacol. Ther. 42:96–99 (1987)) were indeed found to be CYP2C19$_m$/CYP2C19$_{wt}$. Thus, the inheritance of the genotype agrees with the Mendelian autosomal-recessive inheritance of phenotype.

The DNA of three individuals (CYP2C19$_{wt}$/CYP2C19$_{wt}$, CYP$^2$C19$_m$/CYP$^2$C19$_m$, and CYP2C19$_{wt}$/CYP2C19$_m$) was amplified as described above and sequenced directly using an automated sequencer (Applied Biosystems) (FIG. 15). Surprisingly, the sequence of intron 4 of the defective gene was identical to that of the normal gene. The only alteration found in CYP2C19$_m$ was a G→A change in exon 5 corresponding to position 681 of the cDNA. This mutation introduces a cryptic splice site in this exon. This mutation also abolishes a SmaI site at this position (CCCGGG→CCCAGG). The cryptic splice site shows slightly greater sequence identity to the consensus sequence for mammalian splice sites (Green, Ann. Rev. Cell Biol. 7:559–599 (1991)) than the normal splice site. A second potential branch point is also seen near the cryptic splice site. Surprisingly, the cDNA sequences from CYP2C8 and CYP2C18 have a comparable potential cryptic splice site at the same point in exon 5 to that of CYP2C19$_m$, but the presence of the full-length 2C8 protein on immunoblots of human liver microsomes indicates that the majority of this protein is spliced correctly.

Figures 13A, 13B:
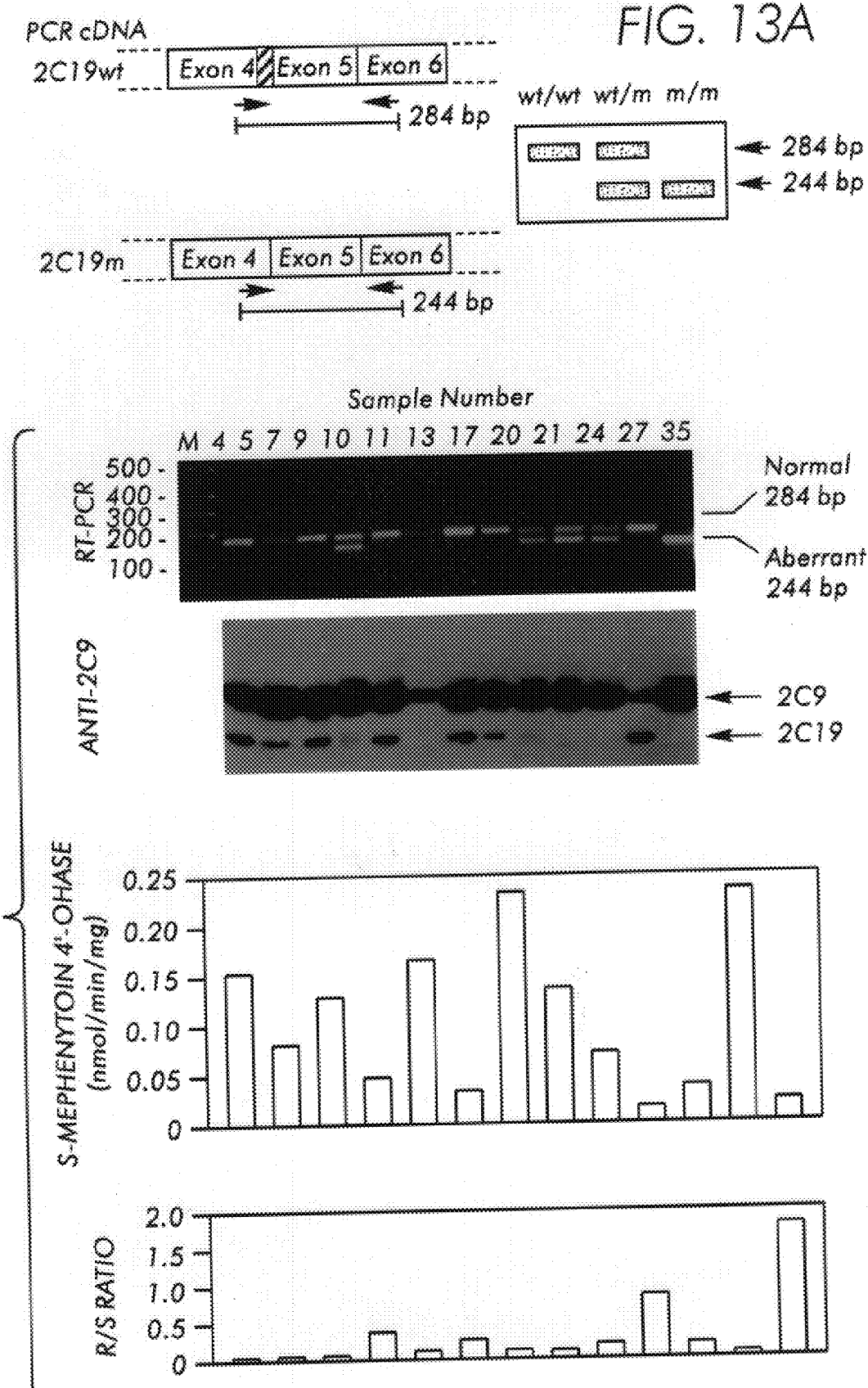
FIG. 13(A–B) A. Diagram of strategy to amplify CYP2C19 cDNA transcripts from human liver samples. The sequence for the PCR primers is indicated in FIG. 12. This strategy yielded a 284 bp band for the normal cDNA, a 244 bp band for the aberrant cDNA and both bands with cDNA from heterozygous individuals. The hatched area indicates the 40 bp deleted in exon 5 of the aberrant cDNA. B. Relation between genotype as assessed by reverse transcription PCR (RT-PCR) of human liver mRNA, CYP2C19 protein estimated by immunoblotting, S-mephenytoin hydroxylation activity, and the ratio of metabolism of the R/S enantiomers. In vitro phenotype was based on high (E), intermediate (I) or low (P) S-mephenytoin 4'-hydroxylase activity.

Three of the samples tested by cDNA analysis in FIG. 13 (sample 13, predicted genotype CYP2C19$_{wt}$/CYP2C19$_{wt}$), sample 21, predicted genotype CYP2C19$_{wt}$/CYP2C19$_m$, and sample 35, predicted genotype CYP2C19$_m$/CYP2C19$_m$) were retested by genomic analysis. Perfect agreement was observed. The cryptic splice site appeared to be used exclusively in sample 35 which is a predicted poor metabolizer and also in liver RNA of an additional CYP2C19$_m$/CYP2C19$_m$ individual. The selection of the cryptic splice site results in the absence of CYP2C19 in liver microsomes from poor metabolizers (FIG. 13).

(d) Conclusion

The principal genetic defect (CYP2C19$_m$) which is responsible for the poor metabolism of S-mephenytoin is a G-A mutation at position 681 of the coding sequence (within exon 5). CYP2C19$_m$ accounts for 75% of the defective alleles in both Caucasian and Oriental poor metabolizers. The single base change generates a cryptic internal splice site, which is used exclusively to produce an aberrantly spliced mRNA containing a 40 bp deletion. The CYP2C19 protein is virtually absent in livers of poor metabolizers. The mutation at position 681 is easily detected by PCR amplification of a segment of genomic 2C19 DNA spanning the mutation.

Example 7

Identification and Diagnostic Assay for a Second Polymorphism (designated 636) in 2C19

A second mutation designated the 636 polymorphism (also known as CYP2C19$_{m2}$) has identified. Genomic DNA from a Oriental poor metabolizer (subject 43 in Example 6) was amplified by PCR using a forward primer complementary to the antisense strand of intron 3 extending from bases −79 to −55 and a reverse primer complementary to the sense strand extending from 79–89 bases into intron 4 (forward primer 5'-TATTATCTGTTAACTAATATGA-3' (SEQ. ID. No. 57) and reverse primer 5'-ACTTCAGGGCTTGGTCAATA-3' (SEQ. ID. No. 58). These primers were selected to amplify a 329 base pair product containing all of exon 4 and the surrounding intron/exon junctions. See FIG. 17. Sequencing of the PCR products with an Applied Biosystems sequencer identified two mutations in exon 4 of the Oriental poor metabolizer. A second mutation at nucleotide 636 entailed a G→A transition at the nucleotide level and the conversion of a tryptophan codon at position 212 (TGG→TGA) to a premature stop codon. This change would result in a truncated 211 amino acid polypeptide containing only the first 4 exons, which would not contain the heme-binding region and would be inactive. The change at position 636 also destroys a BamHI site (GGATCC→GAATCC) (or its isoschizomer BstI) at positions 635–640.

Figure 18:
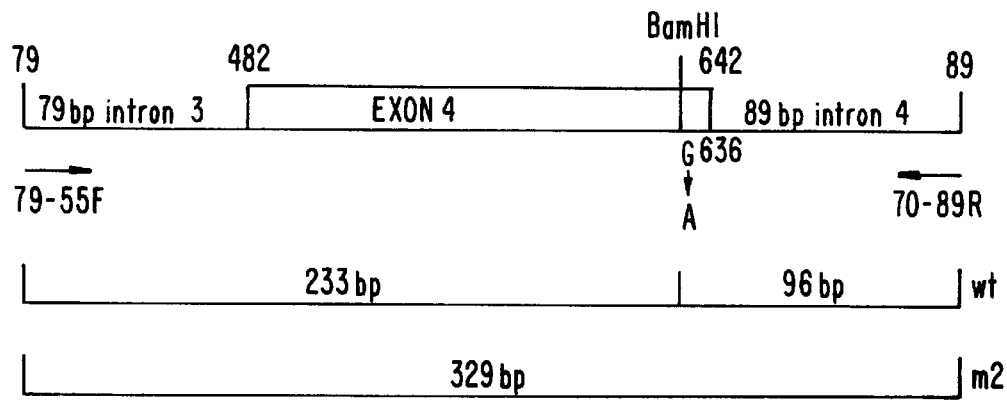
FIG. 18 Diagnosis of 636 mutation in 2C19. The position of the PCR primers is indicated by arrows at 79–55 base pairs in intron 3 and 70–89 bp in intron 4. The size of the PCR products expected in the wild type gene (wt) and the size of the product in the 636 mutant allele are shown in the bottom lines.

A PCR test was developed using the primers described above to amplify a 329 base pair product. The PCR product from the wild-type DNA from extensive metabolizers was cut with BamHI to yield two expected fragments with sizes of 233 base pairs and 96 base pairs (FIG. 18). The PCR fragment amplified from the individual with the 636 mutation (i.e., Oriental subject #43) could not be restricted, indicating that he was homozygous for the 636 mutation. Genotyping of 7 Oriental poor metabolizers whose phenotype could not be explained by the previous 681 mutation indicated that subjects 41 and 43 were homozygous for the 636 mutation, while subjects 36, 48, 11, 69, and 100, were heterozygous for bearing both 636 and 681 mutant alleles. The DNA in homozygous 636 mutant subjects 41 and 43 was not cut by BamHI. The DNA in the heterozygotes yielded three bands at 327, 232, and 95 bp. The DNA from these heterozygotes also yielded three bands from SmaI site (169, 120, and 49 bp) indicating they were also heterozygous for the 681 base pair mutation named CYP2C19$_m$). These data show that the 636 and 681 mutations completely account for the low phenotypes in all of the Oriental poor metabolizers of S-mephenytoin tested (17 individuals with 34 alleles).

Three Caucasian poor metabolizers who were not homozygous for the 681 mutation were also genotyped for the 636 mutation. These were subjects JOB1, 502 and 503. One of these individuals (JOB1) was heterozygous for the 681 mutation while the other two did not contain the 681 mutation in either allele. None of these individuals exhibited a 636 mutation. Thus, there is probably at least one additional polymorphism in 2C19 in Caucasians.

In summary, the 681 and 636 mutations explain 100% of Oriental poor metabolizers, and the 681 mutation alone accounts for about 75% of Caucasian poor metobilizers.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of diagnosing a patient having a deficiency in S-mephenytoin 4'-hydroxylase activity, the method comprising:

obtaining a sample of nucleic acids from the patient; and
    analyzing a cytochrome P450 2C19 DNA sequence from the nucleic acids in the sample for the presence of a polymorphism indicative of the deficiency;
    wherein the polymorphism occurs at nucleotide 681 or nucleotide 636 of the coding region of the P450 2C19 DNA genomic or cDNA sequence,
    wherein each nucleotide in the coding region of the genomic sequence is designated the same number as the corresponding nucleotide in the coding region of the cDNA sequence in FIG. 2, clone 11a (SEQ. ID. No. 2) when the genomic sequence and cDNA sequence are maximally aligned and the nucleotides in the coding region of the cDNA sequence are assigned successive numbers starting at 1 for the A residue of the initiating methionine codon.

2. The method of claim 1, further comprising the step of amplifying the cytochrome P450 2C19 DNA sequence.

3. The method of claim 2, wherein the P450 2C19 DNA sequence is genomic.

4. The method of claim 3, wherein the amplifying step is primed from a forward primer sufficiently complementary to a first subsequence of the antisense strand of the 2C19 sequence to hybridize therewith, and a reverse primer sufficiently complementary to a second subsequence of the sense strand of the 2C19 sequence to hybridize therewith.

5. The method of claim 4, wherein the polymorphism occurs at nucleotide 681 of the coding region of the P450 2C19 DNA genomic sequence.

6. The method of claim 5, wherein the first subsequence of the sense strand is upstream from nucleotide 681 of the coding region, and the second subsequence of the antisense strand is downstream of nucleotide 681 of the coding region.

7. The method of claim 6, wherein the analyzing step comprises digesting the amplified DNA segment with a restriction enzyme that recognizes a site including nucleotide 681 of the coding region.

8. The method of claim 4, wherein the polymorphism occurs at nucleotide 636 of the coding region of the P450 2C19 DNA genomic sequence.

9. The method of claim 8, wherein the first subsequence of the sense strand is upstream from nucleotide 636 of the coding region, and the second subsequence of the antisense strand is downstream of nucleotide 636 of the coding region.

10. The method of claim 9, wherein the analyzing step comprises digesting the amplified DNA segment with a restriction enzyme that recognizes a site including nucleotide 636 of the coding region.

11. The method of claim 4, wherein the first subsequence of the sense strand is upstream from nucleotide 636 of the coding region, and the second subsequence of the antisense strand is downstream of nucleotide 681 of the coding region.

12. The method of claim 5, wherein the forward primer has about 10–50 contiguous nucleotides from the wildtype 2C19 sequence (SEQ. ID. No. 51) shown in FIG. 16 including the nucleotide at position 681 of the coding region;
    wherein the forward primer primes amplification from the complement of the wildtype 2C19 sequence without priming amplification from the complement of the mutant 2C19 sequence (SEQ. ID. No. 61) shown in FIG. 16.

13. The method of claim 12, wherein the 3' nucleotide of the forward primer is the nucleotide at position 681.

14. The method of claim 5, wherein the reverse primer has
   about 10–50 contiguous nucleotides from the complement of the wildtype 2C19 sequence (SEQ. ID. No. 51) shown in FIG. 16 including the complement to nucleotide 681 of the coding region;
   wherein the reverse primer primes amplification from the wildtype 2C19 sequence without priming amplification from the mutant 2C19 sequence (SEQ. ID. No. 61) shown in FIG. 16.

15. The method of claim 14, wherein the 3' nucleotide of the reverse primer is the complement of the nucleotide at position 681.

16. The method of claim 5, wherein the forward primer has
   about 10–50 contiguous nucleotides from the mutant 2C19 sequence (SEQ. ID. No. 61) shown in FIG. 16 including the nucleotide at position 681 of the coding sequence,
   wherein the forward primer primes amplification from the complement of the mutant 2C19 sequence without priming amplification from the complement of the wildtype 2C19 sequence (SEQ. ID. No. 51) shown in FIG. 16.

17. The method of claim 16, wherein the 3' nucleotide of the forward primer is the nucleotide at position 681.

18. The method of claim 5, wherein the reverse primer has
   about 10–50 contiguous nucleotides from the complement of the mutant 2C19 sequence (SEQ. ID. No. 61) shown in FIG. 16 including the complement to nucleotide 681 of the coding region;
   wherein the reverse primer primes amplification from the mutant 2C19 sequence without priming amplification from the wildtype 2C19 sequence (SEQ. ID. No. 51) shown in FIG. 16.

19. The method of claim 18, wherein the 3' nucleotide of the reverse primer is the complement of the nucleotide at position 681.

20. The method of claim 8, wherein the forward primer has
   about 10–50 contiguous nucleotides from the wildtype 2C19 sequence (SEQ. ID. No. 52) shown in FIG. 17 including the nucleotide at position 636 of the coding region;
   wherein the forward primer primes amplification from the complement of the wildtype 2C19 sequence without priming amplification from the complement of the mutant 2C19 sequence (SEQ. ID. No. 54) shown in FIG. 17.

21. The method of claim 8, wherein the reverse primer has
   about 10–50 contiguous nucleotides from the complement of the wildtype 2C19 sequence (SEQ. ID. No. 52) shown in FIG. 17 including the complement to nucleotide 636 of the coding region;
   wherein the reverse primer primes amplification from the wildtype 2C19 sequence without priming amplification from the mutant 2C19 sequence (SEQ. ID. No. 54) shown in FIG. 17.

22. The method of claim 8, wherein the forward primer has
   about 10–50 contiguous nucleotides from the mutant 2C19 sequence (SEQ. ID. No. 54) shown in FIG. 17 including the nucleotide at position 636 of the coding sequence,
   wherein the forward primer primes amplification from the complement of the mutant 2C19 sequence without priming amplification from the complement of the wildtype 2C19 sequence (SEQ. ID. No. 52) shown in FIG. 17.

23. The method of claim 8, wherein the reverse primer has
   about 10–50 contiguous nucleotides from the complement of the mutant 2C19 sequence (SEQ. ID. No. 54) shown in FIG. 17 including the complement to nucleotide 636 of the coding region;
   wherein the reverse primer primes amplification from the mutant 2C19 sequence without priming amplification from the wildtype 2C19 sequence (SEQ. ID. No. 52) shown in FIG. 17.

24. The method of claim 2, wherein the segment of the 2C19 sequence to be amplified is a cDNA sequence, and the method further comprises the step of reverse transcribing mRNA in the sample to produce the cDNA sequence.

25. The method of claim 24, wherein the forward primer comprises about 10–50 contiguous nucleotides upstream of nucleotide 643 of the coding region of the wildtype 2C19 cDNA sequence (SEQ. ID. No. 49) shown in FIG. 12 and hybridizes to the complement of the 2C19 sequence upstream from nucleotide 643 of the coding region, and the reverse primer comprises about 10–50 contiguous nucleotides from the complement of the wildtype 2C19 cDNA sequence (SEQ. ID. No. 49) shown in FIG. 12 and hybridizes to the 2C19 sequence downstream from nucleotide 682 of the coding region.

26. The method of claim 24, wherein the forward primer hybridizes to the complement of the wildtype 2C19 cDNA sequence (SEQ. ID. No. 49) shown in FIG. 12 between nucleotides 643 and 682 without hybridizing to the complement of the mutant 2C19 cDNA sequence (SEQ. ID. No. 50) shown in FIG. 12.

27. The method of claim 26, wherein the reverse primer hybridizes to the wildtype 2C19 cDNA sequence (SEQ. ID. No. 49) shown in FIG. 12 between nucleotides 643 and 682 without hybridizing to the mutant 2C19 cDNA sequence (SEQ. ID. No. 50) shown in FIG. 12.

28. The method of claim 24, wherein the forward primer comprises about 10–50 contiguous nucleotides upstream of nucleotide 636 of the coding region of the wildtype 2C19 cDNA sequence (SEQ. ID. No. 49) shown in FIG. 12, and the reverse primer comprises about 10–50 contiguous nucleotides from the complement of the wildtype 2C19 cDNA sequence (SEQ. ID. No. 49) shown in FIG. 12 downstream from nucleotide 636 of the coding region.

29. The method of claim 24, wherein the full-length 2C19 cDNA sequence is amplified.

30. The method of claim 29, further comprising the step of sequencing a segment of the 2C19 cDNA sequence.

31. The method of claim 1 further comprising the step of:
   digesting the 2C19 DNA sequence with a restriction enzyme that recognizes a site including nucleotide 636 or 681 of the 2C19 DNA sequence;
   wherein:
   the 2C19 DNA sequence is genomic; and
   the analyzing step comprises detecting the products resulting from the digestion by Southern blotting with a labelled segment of the 2C19 DNA sequence as a probe, wherein each nucleotide in the coding region of the DNA is designated the same number as the corresponding nucleotide in the coding region of the cDNA sequence in FIG. 2, clone 11a (SEQ. ID. No. 2), when the DNA and the cDNA sequence are maximally aligned, and the nucleotides in the coding region of the cDNA sequence are assigned successive numbers starting at 1 for the A residue of the initiating methionine codon.

32. A diagnostic kit comprising:

a forward primer sufficiently complementary with a first subsequence of the antisense strand of a double-stranded 2C19 genomic DNA sequence to hybridize therewith, and a reverse primer sufficiently complementary with a second subsequence of the sense strand of the 2C19 genomic sequence to hybridize therewith;

wherein the first subsequence is upstream of nucleotide 681 of the coding region, and second subsequence is downstream of nucleotide 681 of the coding region, wherein each nucleotide in the coding region of the genomic DNA sequence is designated the same number as the corresponding nucleotide in the coding region of the cDNA sequence in FIG. 2, clone 11a (SEQ. ID. No. 2), when the genomic DNA and the cDNA sequence are maximally aligned, and the nucleotides in the coding region of the cDNA sequence are assigned successive numbers starting at 1 for the A residue of the initiating methionine codon wherein said subsequences are within a segment bordered by the 5' end of the third and 3' end of the fifth intronic regions of the 2C19 genomic DNA sequence.

33. The diagnostic kit of claim 32, wherein the first subsequence is upstream from nucleotide 636 of the coding region.

34. The diagnostic kit of claim 32, wherein the forward primer has about 10–50 contiguous nucleotides from the wildtype 2C19 sequence shown in FIG. 16 (SEQ. ID. No. 51), and the reverse primer has about 10–50 contiguous nucleotides from the complement of the wildtype 2C19 sequence shown in FIG. 16.

35. The diagnostic kit of claim 34, further comprising a second forward primer sufficiently complementary to a first subsequence of the antisense strand of a double-stranded 2C19 genomic DNA sequence to hybridize therewith, and a a second reverse primer sufficiently complementary with a second subsequence of the sense strand of the 2C19 genomic sequence to hybridize therewith;

wherein the first subsequence is upstream of nucleotide 636 of the coding region, and second subsequence is downstream of nucleotide 636 of the coding region wherein said subsequences of the second forward and second reverse primers are within a segment bordered by the 5' end of the third and 3' end of the fourth intronic regions of the 2C19 genomic DNA sequence.

36. The diagnostic kit of claim 35, further comprising a restriction enzyme that recognizes a site that includes nucleotide 681 or nucleotide 636 of the coding region.

37. A diagnostic kit comprising:

a forward primer sufficiently complementary with a first subsequence of the antisense strand of a double-stranded 2C19 genomic DNA sequence to hybridize therewith, and a reverse primer sufficiently complementary with a second subsequence of the sense strand of the 2C19 genomic sequence to hybridize therewith;

wherein the first subsequence is upstream of nucleotide 636 of the coding region, and second subsequence is downstream of nucleotide 636 of the coding region, wherein each nucleotide in the coding region of the genomic DNA sequence is designated the same number as the corresponding nucleotide in the coding region of the cDNA sequence in FIG. 2, clone 11a (SEQ. ID. No. 2), when the genomic DNA and the cDNA sequence are maximally aligned, and the nucleotides in the coding region of the cDNA sequence are assigned successive numbers starting at 1 for the A residue of the initiating methionine codon wherein said subsequences are within a segment bordered by the 5' end of the third and 3' end of the fourth intronic regions of the 2C19 genomic DNA sequence.

* * * * *

SEQUENCE LISTING (1) GENERAL INFORMATION:

(iii) NUMBER OF SEQUENCES: 61

(2) INFORMATION FOR SEQ ID NO:1:

(i) SEQUENCE CHARACTERISTICS:
      (A) LENGTH: 490 amino acids
      (B) TYPE: amino acid
      (D) TOPOLOGY: unknown (ii) MOLECULE TYPE: protein (xi) SEQUENCE DESCRIPTION: SEQ ID NO:1:

```
Met Asp Pro Phe Val Val Leu Val Leu Cys Leu Ser Cys Leu Leu Leu
1               5                  10                  15

Leu Ser Ile Trp Arg Gln Ser Ser Gly Arg Gly Lys Leu Pro Pro Gly
                20                  25                  30

Pro Thr Pro Leu Pro Val Ile Gly Asn Ile Leu Gln Ile Asp Ile Lys
            35                  40                  45

Asp Val Ser Lys Ser Leu Thr Asn Leu Ser Lys Ile Tyr Gly Pro Val
        50                  55                  60

Phe Thr Leu Tyr Phe Gly Leu Glu Arg Met Val Val Leu His Gly Tyr
65                  70                  75                  80
```

```
Glu Val Val Lys Glu Ala Leu Ile Asp Leu Gly Glu Glu Phe Ser Gly
                85                  90                  95

Arg Gly His Phe Pro Leu Ala Glu Arg Ala Asn Arg Gly Phe Gly Ile
            100                 105                 110

Val Phe Ser Asn Gly Lys Arg Trp Lys Glu Ile Arg Arg Phe Ser Leu
            115                 120                 125

Met Thr Leu Arg Asn Phe Gly Met Gly Lys Arg Ser Ile Glu Asp Arg
        130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe Gln Lys Arg Phe Asp Tyr Lys Asp Gln
                180                 185                 190

Gln Phe Leu Asn Leu Met Glu Lys Leu Asn Glu Asn Ile Arg Ile Val
            195                 200                 205

Ser Thr Pro Trp Ile Gln Ile Cys Asn Asn Phe Pro Thr Ile Ile Asp
        210                 215                 220

Tyr Phe Pro Gly Thr His Asn Lys Leu Leu Lys Asn Leu Ala Phe Met
225                 230                 235                 240

Glu Ser Asp Ile Leu Glu Lys Val Lys Glu His Gln Glu Ser Met Asp
                245                 250                 255

Ile Asn Asn Pro Arg Asp Phe Ile Asp Cys Phe Leu Ile Lys Met Glu
                260                 265                 270

Lys Glu Lys Gln Asn Gln Gln Ser Glu Phe Thr Ile Glu Asn Leu Val
            275                 280                 285

Ile Thr Ala Ala Asp Leu Leu Gly Ala Gly Thr Glu Thr Thr Ser Thr
        290                 295                 300

Thr Leu Arg Tyr Ala Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Gly His Met Pro Tyr Thr Asp Ala Val Val
            340                 345                 350

His Glu Val Gln Arg Tyr Ile Asp Leu Ile Pro Thr Ser Leu Pro His
        355                 360                 365

Ala Val Thr Cys Asp Val Lys Phe Arg Asn Tyr Leu Ile Pro Lys Gly
370                 375                 380

Thr Thr Ile Leu Thr Ser Leu Thr Ser Val Leu His Asp Asn Lys Glu
385                 390                 395                 400

Phe Pro Asn Pro Glu Met Phe Asp Pro Arg His Phe Leu Asp Glu Gly
                405                 410                 415

Gly Asn Phe Lys Lys Ser Asn Tyr Phe Met Pro Phe Ser Ala Gly Lys
            420                 425                 430

Arg Ile Cys Val Gly Glu Gly Leu Ala Arg Met Glu Leu Phe Leu Phe
        435                 440                 445

Leu Thr Phe Ile Leu Gln Asn Phe Asn Leu Lys Ser Leu Ile Asp Pro
450                 455                 460

Lys Asp Leu Asp Thr Thr Pro Val Val Asn Gly Phe Ala Ser Val Pro
465                 470                 475                 480

Pro Phe Tyr Gln Leu Cys Phe Ile Pro Val
                485                 490
```

(2) INFORMATION FOR SEQ ID NO:2:

(i) SEQUENCE CHARACTERISTICS:
        (A) LENGTH: 1746 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Region
        (B) LOCATION: 1..5
        (D) OTHER INFORMATION: /note= "Corresponds to positions -5 to-1
            for 11a of Figure 2."

(xi) SEQUENCE DESCRIPTION: SEQ ID NO:2:

```
CTTCAATGGA TCCTTTTGTG GTCCTTGTGC TCTGTCTCTC ATGTTTGCTT CTCCTTTCAA       60

TCTGGAGACA GAGCTCTGGG AGAGGAAAAC TCCCTCCTGG CCCCACTCCT CTCCCAGTGA      120

TTGGAAATAT CCTACAGATA GATATTAAGG ATGTCAGCAA ATCCTTAACC AATCTCTCAA      180

AAATCTATGG CCCTGTGTTC ACTCTGTATT TTGGCCTGGA ACGCATGGTG GTGCTGCATG      240

GATATGAAGT GGTGAAGGAA GCCCTGATTG ATCTTGGAGA GGAGTTTTCT GGAAGAGGCC      300

ATTTCCCACT GGCTGAAAGA GCTAACAGAG GATTTGGAAT CGTTTTCAGC AATGGAAAGA      360

GATGGAAGGA GATCCGGCGT TTCTCCCTCA TGACGCTGCG GAATTTTGGG ATGGGGAAGA      420

GGAGCATTGA GGACCGTGTT CAAGAGGAAG CCCGCTGCCT TGTGGAGGAG TTGAGAAAAA      480

CCAAGGCTTC ACCCTGTGAT CCCACTTTCA TCCTGGGCTG TGCTCCCTGC AATGTGATCT      540

GCTCCATTAT TTTCCAGAAA CGTTTCGATT ATAAAGATCA GCAATTTCTT AACTTGATGG      600

AAAAATTGAA TGAAACATC AGGATTGTAA GCACCCCCTG GATCCAGATA TGCAATAATT      660

TTCCCACTAT CATTGATTAT TTCCCGGGAA CCCATAACAA ATTACTTAAA AACCTTGCTT      720

TTATGGAAAG TGATATTTTG GAGAAAGTAA AGAACACCA AGAATCGATG GACATCAACA       780

ACCCTCGGGA CTTTATTGAT TGCTTCCTGA TCAAAATGGA GAAGGAAAAG CAAAACCAAC      840

AGTCTGAATT CACTATTGAA AACTTGGTAA TCACTGCAGC TGACTTACTT GGAGCTGGGA      900

CAGAGACAAC AAGCACAACC CTGAGATATG CTCTCCTTCT CCTGCTGAAG CACCCAGAGG      960

TCACAGCTAA AGTCCAGGAA GAGATTGAAC GTGTCATTGG CAGAAACCGG AGCCCCTGCA     1020

TGCAGGACAG GGGCCACATG CCCTACACAG ATGCTGTGGT GCACGAGGTC CAGAGATACA     1080

TCGACCTCAT CCCCACCAGC CTGCCCCATG CAGTGACCTG TGACGTTAAA TTCAGAAACT     1140

ACCTCATTCC CAAGGGCACA ACCATATTAA CTTCCCTCAC TTCTGTGCTA CATGACAACA     1200

AAGAATTTCC CAACCCAGAG ATGTTTGACC CTCGTCACTT TCTGGATGAA GGTGGAAATT     1260

TTAAGAAAAG TAACTACTTC ATGCCTTTCT CAGCAGGAAA ACGGATTTGT GTGGGAGAGG     1320

GCCTGGCCCG CATGGAGCTG TTTTTATTCC TGACCTTCAT TTTACAGAAC TTTAACCTGA     1380

AATCTCTGAT TGACCCAAAG GACCTTGACA CAACTCCTGT TGTCAATGGA TTTGCTTCTG     1440

TCCCGCCCTT CTATCAGCTG TGCTTCATTC CTGTCTGAAG AAGCACAGAT GGTCTGGCTG     1500

CTCCTGTGCT GTCCCTGCAG CTCTCTTTCC TCTGGTCCAA ATTTCACTAT CTGTGATGCT     1560

TCTTCTGACC CGTCATCTCA CATTTTCCCT TCCCCCAAGA TCTAGTGAAC ATTCAGCCTC     1620

CATTAAAAAA GTTTCACTGT GCAAATATAT CTGCTATTCC CCATACTCTA TAATAGTTAC     1680

ATTGAGTGCC ACATAATGCT GATACTTGTC TAATGTTGAG TTATTAACAT ATTATTATTA     1740

AATAGA                                                                1746
```

(2) INFORMATION FOR SEQ ID NO:3:

(i) SEQUENCE CHARACTERISTICS:
    (A) LENGTH: 490 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:3:

```
Met Asp Ser Leu Val Val Leu Val Leu Cys Leu Ser Cys Leu Leu Leu
1               5                  10                  15

Leu Ser Leu Trp Arg Gln Ser Ser Gly Arg Gly Lys Leu Pro Pro Gly
            20                  25                  30

Pro Thr Pro Leu Pro Val Ile Gly Asn Ile Leu Gln Ile Gly Ile Lys
        35                  40                  45

Asp Ile Ser Lys Ser Leu Thr Asn Leu Ser Lys Val Tyr Gly Pro Val
    50                  55                  60

Phe Thr Leu Tyr Phe Gly Leu Lys Pro Ile Val Val Leu His Gly Tyr
65                  70                  75                  80

Glu Ala Val Lys Glu Ala Leu Ile Asp Leu Gly Glu Glu Phe Ser Gly
                85                  90                  95

Arg Gly Ile Phe Pro Leu Ala Glu Arg Ala Asn Arg Gly Phe Gly Ile
            100                 105                 110

Val Phe Ser Asn Gly Lys Lys Trp Lys Glu Ile Arg Arg Phe Ser Leu
        115                 120                 125

Met Thr Leu Arg Asn Phe Gly Met Gly Lys Arg Ser Ile Glu Asp Arg
    130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
            180                 185                 190

Gln Phe Leu Asn Leu Met Glu Lys Leu Asn Glu Asn Ile Lys Ile Leu
        195                 200                 205

Ser Ser Pro Trp Ile Gln Ile Cys Asn Asn Phe Ser Pro Ile Ile Asp
    210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Met Asp
                245                 250                 255

Met Asn Asn Pro Gln Asp Phe Ile Asp Cys Phe Leu Met Lys Met Glu
            260                 265                 270

Lys Glu Lys His Asn Gln Pro Ser Glu Phe Thr Ile Glu Ser Leu Glu
        275                 280                 285

Asn Thr Ala Val Asp Leu Phe Gly Ala Gly Thr Glu Thr Thr Ser Thr
    290                 295                 300

Thr Leu Arg Tyr Ala Leu Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Ser His Met Pro Tyr Thr Asp Ala Val Val
            340                 345                 350

His Glu Val Gln Arg Tyr Leu Asp Leu Leu Pro Thr Ser Leu Pro His
        355                 360                 365
```

```
       Ala Val Thr Cys Asp Ile Lys Phe Arg Asn Tyr Leu Ile Pro Lys Gly
           370                 375                 380

Thr Thr Ile Leu Ile Ser Leu Thr Ser Val Leu His Asp Asn Lys Glu
       385                 390                 395                 400

Phe Pro Asn Pro Glu Met Phe Asp Pro His His Phe Leu Asp Glu Gly
                       405                 410                 415

Gly Asn Phe Lys Lys Ser Lys Tyr Phe Met Pro Phe Ser Ala Gly Lys
                   420                 425                 430

Arg Ile Cys Val Gly Glu Ala Leu Ala Gly Met Glu Leu Phe Leu Phe
                   435                 440                 445

Leu Thr Ser Ile Leu Gln Asn Phe Asn Leu Lys Ser Leu Val Asp Pro
       450                 455                 460

Lys Asn Leu Asp Thr Thr Pro Val Val Asn Gly Phe Ala Ser Val Pro
       465                 470                 475                 480

Pro Phe Tyr Gln Leu Cys Phe Ile Pro Val
                       485                 490
```

(2) INFORMATION FOR SEQ ID NO:4:

(i) SEQUENCE CHARACTERISTICS:
        (A) LENGTH: 1854 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Region
        (B) LOCATION: 1..12
        (D) OTHER INFORMATION: /note= "Corresponds to positions -12
            to-1 for 25 of Figure 2."

(xi) SEQUENCE DESCRIPTION: SEQ ID NO:4:

```
GAGAAGGCTT CAATGGATTC TCTTGTGGTC CTTGTGCTCT GTCTCTCATG TTTGCTTCTC      60

CTTTCACTCT GGAGACAGAG CTCTGGGAGA GGAAAACTCC CTCCTGGCCC CACTCCTCTC     120

CCAGTGATTG GAAATATCCT ACAGATAGGT ATTAAGGACA TCAGCAAATC CTTAACCAAT     180

CTCTCAAAGG TCTATGGCCC TGTGTTCACT CTGTATTTTG GCCTGAAACC CATAGTGGTG     240

CTGCATGGAT ATGAAGCAGT GAAGGAAGCC CTGATTGATC TTGGAGAGGA GTTTTCTGGA     300

AGAGGCATTT TCCCACTGGC TGAAAGAGCT AACAGAGGAT TTGGAATTGT TTTCAGCAAT     360

GGAAAGAAAT GGAAGGAGAT CCGGCGTTTC TCCCTCATGA CGCTGCGGAA TTTTGGGATG     420

GGGAAGAGGA GCATTGAGGA CCGTGTTCAA GAGGAAGCCC GCTGCCTTGT GGAGGAGTTG     480

AGAAAAACCA AGGCCTCACC CTGTGATCCC ACTTTCATCC TGGGCTGTGC TCCCTGCAAT     540

GTGATCTGCT CCATTATTTT CCATAAACGT TTTGATTATA AGATCAGCA ATTTCTTAAC      600

TTAATGGAAA AGTTGAATGA AAACATCAAG ATTTTGAGCA GCCCCTGGAT CCAGATCTGC     660

AATAATTTTT CTCCTATCAT TGATTACTTC CCGGGAACTC ACAACAAATT ACTTAAAAAC     720

GTTGCTTTTA TGAAAGTTA TATTTTGGAA AAAGTAAAAG AACACCAAGA ATCAATGGAC      780

ATGAACAACC CTCAGGACTT TATTGATTGC TTCCTGATGA AAATGGAGAA GGAAAAGCAC     840

AACCAACCAT CTGAATTTAC TATTGAAAGC TTGGAAAACA CTGCAGTTGA CTTGTTTGGA     900

GCTGGGACAG AGACGACAAG CACAACCCTG AGATATGCTC TCCTTCTCCT GCTGAAGCAC     960

CCAGAGGTCA CAGCTAAAGT CCAGGAAGAG ATTGAACGTG TGATTGGCAG AAACCGGAGC    1020

CCCTGCATGC AAGACAGGAG CCACATGCCC TACACAGATG CTGTGGTGCA CGAGGTCCAG    1080

AGATACCTTG ACCTTCTCCC CACCAGCCTG CCCCATGCAG TGACCTGTGA CATTAAATTC    1140
```

```
AGAAACTATC TCATTCCCAA GGGCACAACC ATATTAATTT CCCTGACTTC TGTGCTACAT   1200

GACAACAAAG AATTTCCCAA CCCAGAGATG TTTGACCCTC ATCACTTTCT GGATGAAGGT   1260

GGCAATTTTA AGAAAGTAA ATACTTCATG CCTTTCTCAG CAGGAAAACG GATTTGTGTG   1320

GGAGAAGCCC TGGCCGGCAT GGAGCTGTTT TTATTCCTGA CCTCCATTTT ACAGAACTTT   1380

AACCTGAAAT CTCTGGTTGA CCCAAAGAAC CTTGACACCA CTCCAGTTGT CAATGGTTTT   1440

GCCTCTGTGC CGCCCTTCTA CCAGCTGTGC TTCATTCCTG TCTGAAGAAG AGCAGATGGC   1500

CTGGCTGCTG CTGTGCAGTC CCTGCAGCTC TCTTTCCTCT GGGGCATTAT CCATCTTTCA   1560

CTATCTGTAA TGCCTTTTCT CACCTGTCAT CTCACATTTT CCCTTCCCTG AAGATCTAGT   1620

GAACATTCGA CCTTCATTAC GGAGAGTTTC CTATGTTTCA CTGTGCAAAT ATATCTGCTA   1680

TTCTCCATAC TCTGTAACAG TTGCATTGAC TGTCACATAA TGCTCATACT TATCTAATGT   1740

TGAGTTATTA ATATGTTATT ATTAAATAGA GAAATATGAT TTGTGTATTA TAATTCAAAG   1800

GCATTTCTTT TCTGCATGTT CTAAATAAAA AGCATTATTA TTTGCTGAAA AAAA           1854

(2) INFORMATION FOR SEQ ID NO:5:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Asp Pro Ala Val Ala Leu Val Leu Cys Leu Ser Cys Leu Phe Leu
    1               5                   10                  15

Leu Ser Leu Trp Arg Gln Ser Ser Gly Arg Gly Arg Leu Pro Ser Gly
                20                  25                  30

Pro Thr Pro Leu Pro Ile Ile Gly Asn Ile Leu Gln Leu Asp Val Lys
                35                  40                  45

Asp Met Ser Lys Ser Leu Thr Asn Phe Ser Lys Val Tyr Gly Pro Val
    50                  55                  60

Phe Thr Val Tyr Phe Gly Leu Lys Pro Ile Val Val Leu His Gly Tyr
    65                  70                  75                  80

Glu Ala Val Lys Glu Ala Leu Ile Asp His Gly Glu Glu Phe Ser Gly
                    85                  90                  95

Arg Gly Ser Phe Pro Val Ala Glu Lys Val Asn Lys Gly Leu Gly Ile
                100                 105                 110

Leu Phe Ser Asn Gly Lys Arg Trp Lys Glu Ile Arg Arg Phe Cys Leu
                115                 120                 125

Met Thr Leu Arg Asn Phe Gly Met Gly Lys Arg Ser Ile Glu Asp Arg
    130                 135                 140

Val Gln Glu Glu Ala Arg Cys Leu Val Glu Glu Leu Arg Lys Thr Asn
    145                 150                 155                 160

Ala Ser Pro Cys Asp Pro Thr Phe Ile Leu Gly Cys Ala Pro Cys Asn
                    165                 170                 175

Val Ile Cys Ser Val Ile Phe His Asp Arg Phe Asp Tyr Lys Asp Gln
                180                 185                 190

Arg Phe Leu Asn Leu Met Glu Lys Phe Asn Glu Asn Leu Arg Ile Leu
                195                 200                 205

Ser Ser Pro Trp Ile Gln Val Cys Asn Asn Phe Pro Ala Leu Ile Asp
                210                 215                 220
```

```
Tyr Leu Pro Gly Ser His Asn Lys Ile Ala Glu Asn Phe Ala Tyr Ile
225                 230                 235                 240

Lys Ser Tyr Val Leu Glu Arg Ile Lys Glu His Gln Glu Ser Leu Asp
            245                 250                 255

Met Asn Ser Ala Arg Asp Phe Ile Asp Cys Phe Leu Ile Lys Met Glu
        260                 265                 270

Gln Glu Lys His Asn Gln Gln Ser Glu Phe Thr Val Glu Ser Leu Ile
    275                 280                 285

Ala Thr Val Thr Asp Met Phe Gly Ala Gly Thr Glu Thr Thr Ser Thr
290                 295                 300

Thr Leu Arg Tyr Gly Leu Leu Leu Leu Lys Tyr Pro Glu Val Thr
305                 310                 315                 320

Ala Lys Val Gln Glu Ile Glu Cys Val Val Gly Arg Asn Arg Ser
            325                 330                 335

Pro Cys Met Gln Asp Arg Ser His Met Pro Tyr Thr Asp Ala Val Val
        340                 345                 350

His Glu Ile Gln Arg Tyr Ile Asp Leu Leu Pro Thr Asn Leu Pro His
    355                 360                 365

Ala Val Thr Cys Asp Val Lys Phe Lys Asn Tyr Leu Ile Pro Lys Gly
370                 375                 380

Thr Thr Ile Ile Thr Ser Leu Thr Ser Val Leu His Asn Asp Lys Glu
385                 390                 395                 400

Phe Pro Asn Pro Glu Met Phe Asp Pro Gly His Phe Leu Asp Lys Ser
            405                 410                 415

Gly Asn Phe Lys Lys Ser Asp Tyr Phe Met Pro Phe Ser Ala Gly Lys
        420                 425                 430

Arg Met Cys Met Gly Glu Gly Leu Ala Arg Met Glu Leu Phe Leu Phe
    435                 440                 445

Leu Thr Thr Ile Leu Gln Asn Phe Asn Leu Lys Ser Gln Val Asp Pro
450                 455                 460

Lys Asp Ile Asp Ile Thr Pro Ile Ala Asn Ala Phe Gly Arg Val Pro
465                 470                 475                 480

Pro Leu Tyr Gln Leu Cys Phe Ile Pro Val
            485                 490
```

(2) INFORMATION FOR SEQ ID NO:6:

(i) SEQUENCE CHARACTERISTICS:
  (A) LENGTH: 2009 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: Region
  (B) LOCATION: 1..199
  (D) OTHER INFORMATION: /note= "Corresponds to positions -199to
   -1 for 29c of Figure 2."

(xi) SEQUENCE DESCRIPTION: SEQ ID NO:6:

```
GGCACCGGAA AGAACAAGAA AAAGAACAC CTTATTTTTA TCTTCTTCAG TGAGCCAATG      60

TTCATTCAAA AGAGAGATTA AAGTGCTTTT TGCTGACTAG TCACAGTCAG AGTCAGAATC    120

ACAGGTGGAT TAGTAGGGAG TGTTATAAAA GCCTTGAAGT GAAAGCCCGC AGTTGTCTTA    180

CTAAGAAGAG AAGCCTTCAA TGGATCCAGC TGTGGCTCTG GTGCTCTGTC TCTCCTGTTT    240

GTTTCTCCTT TCACTCTGGA GGCAGAGCTC TGGAAGAGGG AGGCTCCCGT CTGGCCCCAC    300
```

-continued

```
TCCTCTCCCG ATTATTGGAA ATATCCTGCA GTTAGATGTT AAGGACATGA GCAAATCCTT       360

AACCAATTTC TCAAAAGTCT ATGGCCCTGT GTTCACTGTG TATTTTGGCC TGAAGCCCAT       420

TGTGGTGTTG CATGGATATG AAGCAGTGAA GGAGGCCCTG ATTGATCATG GAGAGGAGTT       480

TTCTGGAAGA GGAAGTTTTC CAGTGGCTGA AAAAGTTAAC AAAGGACTTG GAATCCTTTT       540

CAGCAATGGA AAGAGATGGA AGGAGATCCG GCGTTTCTGC CTCATGACTC TGCGGAATTT       600

TGGGATGGGG AAGAGGAGCA TCGAGGACCG TGTTCAAGAG AAGCCCGCT GCCTTGTGGA       660

GGAGTTGAGA AAAACCAATG CCTCACCCTG TGATCCCACT TTCATCCTGG GCTGTGCTCC       720

CTGCAATGTG ATCTGCTCTG TTATTTTCCA TGATCGATTT GATTATAAAG ATCAGAGGTT       780

TCTTAACTTG ATGGAAAAAT TCAATGAAAA CCTCAGGATT CTGAGCTCTC CATGGATCCA       840

GGTCTGCAAT AATTTCCCTG CTCTCATCGA TTATCTCCCA GGAAGTCATA ATAAAATAGC       900

TGAAAATTTT GCTTACATTA AAAGTTATGT ATTGGAGAGA ATAAAAGAAC ATCAAGAATC       960

CCTGGACATG AACAGTGCTC GGGACTTTAT TGATTGTTTC CTGATCAAAA TGGAACAGGA      1020

AAAGCACAAT CAACAGTCTG AATTTACTGT TGAAAGCTTG ATAGCCACTG TAACTGATAT      1080

GTTTGGGGCT GGAACAGAGA CAACGAGCAC CACTCTGAGA TATGGACTCC TGCTCCTGCT      1140

GAAGTACCCA GAGGTCACAG CTAAAGTCCA GGAAGAGATT GAATGTGTAG TTGGCAGAAA      1200

CCGGAGCCCC TGTATGCAGG ACAGGAGTCA CATGCCCTAC ACAGATGCTG TGGTGCACGA      1260

GATCCAGAGA TACATTGACC TCCTCCCCAC CAACCTGCCC CATGCAGTGA CCTGTGATGT      1320

TAAATTCAAA AACTACCTCA TCCCCAAGGG CACGACCATA ATAACATCCC TGACTTCTGT      1380

GCTGCACAAT GACAAAGAAT TCCCCAACCC AGAGATGTTT GACCCTGGCC ACTTTCTGGA      1440

TAAGAGTGGC AACTTTAAGA AAAGTGACTA CTTCATGCCT TTCTCAGCAG GAAAACGGAT      1500

GTGTATGGGA GAGGGCCTGG CCCGCATGGA GCTGTTTTTA TTCCTGACCA CCATTTTGCA      1560

GAACTTTAAC CTGAAATCTC AGGTTGACCC AAAGGATATT GACATCACCC CCATTGCCAA      1620

TGCATTTGGT CGTGTGCCAC CCTTGTACCA GCTCTGCTTC ATTCCTGTCT GAAGAAGGGC      1680

AGATAGTTTG GCTGCTCCTG TGCTGTCACC TGCAATTCTC CCTTATCAGG GCCATTAGCC      1740

TCTCCCTTCT CTCTGTGAGG GATATTTTCT CTGACTTGTC AATCCACATC TTCCCATTCC      1800

CTCAAGATCC AATGAACATC CAACCTCCAT TAAAGAGAGT TTCTTGGGTC ACTTCCTAAA      1860

TATATCTGCT ATTCTCCATA CTCTGTATCA CTTGTATTGA CCACCACATA TGCTAATACC      1920

TATCTACTGC TGAGTTGTCA GTATGTTATC ACTAGAAAAC AAAGAAAAAT GATTAATAAA      1980

TGACAATTCA GAGCCAAAAA AAAAAAAAA                                       2009
```

(2) INFORMATION FOR SEQ ID NO:7:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Glu Pro Phe Val Val Leu Val Leu Cys Leu Ser Phe Met Leu Leu
 1               5                  10                  15

Phe Ser Leu Trp Arg Gln Ser Cys Arg Arg Lys Leu Pro Pro Gly
                20                  25                  30

Pro Thr Pro Leu Pro Ile Ile Gly Asn Met Leu Gln Ile Asp Val Lys
            35                  40                  45
```

```
Asp Ile Cys Lys Ser Phe Thr Asn Phe Ser Lys Val Tyr Gly Pro Val
 50                      55                      60

Phe Thr Val Tyr Phe Gly Met Asn Pro Ile Val Val Phe His Gly Tyr
 65                      70                      75                      80

Glu Ala Val Lys Glu Ala Leu Ile Asp Asn Gly Glu Gly Phe Ser Gly
                 85                      90                      95

Arg Gly Asn Ser Pro Ile Ser Gln Arg Ile Thr Lys Gly Leu Gly Ile
                100                     105                     110

Ile Ser Ser Asn Gly Lys Arg Trp Lys Glu Ile Arg Arg Phe Ser Leu
                115                     120                     125

Thr Asn Leu Arg Asn Phe Gly Met Gly Lys Arg Ser Ile Glu Asp Arg
130                     135                     140

Val Gln Glu Glu Ala His Cys Leu Val Glu Glu Leu Arg Lys Thr Lys
145                     150                     155                     160

Ala Ser Pro Cys Asp Pro Thr Phe Ile Leu Gly Cys Ala Pro Cys Asn
                165                     170                     175

Val Ile Cys Ser Val Val Phe Gln Lys Arg Phe Asp Tyr Lys Asp Gln
                180                     185                     190

Asn Phe Leu Thr Leu Met Lys Arg Phe Asn Glu Asn Phe Arg Ile Leu
                195                     200                     205

Asn Ser Pro Trp Ile Gln Val Cys Asn Asn Phe Pro Leu Leu Ile Asp
210                     215                     220

Cys Phe Pro Gly Thr His Asn Lys Val Leu Lys Asn Val Ala Leu Thr
225                     230                     235                     240

Arg Ser Tyr Ile Arg Glu Lys Val Lys Glu His Gln Ala Ser Leu Asp
                245                     250                     255

Val Asn Asn Pro Arg Asp Phe Met Asp Cys Phe Leu Ile Lys Met Glu
                260                     265                     270

Gln Glu Lys Asp Asn Gln Lys Ser Glu Phe Asn Ile Glu Asn Leu Val
                275                     280                     285

Gly Thr Val Ala Asp Leu Phe Val Ala Gly Thr Glu Thr Thr Ser Thr
290                     295                     300

Thr Leu Arg Tyr Gly Leu Leu Leu Leu Leu Lys His Pro Glu Val Thr
305                     310                     315                     320

Ala Lys Val Gln Glu Glu Ile Asp His Val Ile Gly Arg His Arg Ser
                325                     330                     335

Pro Cys Met Gln Asp Arg Ser His Met Pro Tyr Thr Asp Ala Val Val
                340                     345                     350

His Glu Ile Gln Arg Tyr Ser Asp Leu Val Pro Thr Gly Val Pro His
                355                     360                     365

Ala Val Thr Thr Asp Thr Lys Phe Arg Asn Tyr Leu Ile Pro Lys Gly
                370                     375                     380

Thr Thr Ile Met Ala Leu Leu Thr Ser Val Leu His Asp Asp Lys Glu
385                     390                     395                     400

Phe Pro Asn Pro Asn Ile Phe Asp Pro Gly His Phe Leu Asp Lys Asn
                405                     410                     415

Gly Asn Phe Lys Lys Ser Asp Tyr Phe Met Pro Phe Ser Ala Gly Lys
                420                     425                     430

Arg Ile Cys Ala Gly Glu Gly Leu Ala Arg Met Glu Leu Phe Leu Phe
                435                     440                     445

Leu Thr Thr Ile Leu Gln Asn Phe Asn Leu Lys Ser Val Asp Asp Leu
                450                     455                     460

Lys Asn Leu Asn Thr Thr Ala Val Thr Lys Gly Ile Val Ser Leu Pro
465                     470                     475                     480
```

```
            Pro Ser Tyr Gln Ile Cys Phe Ile Pro Val
                    485                 490

(2) INFORMATION FOR SEQ ID NO:8:

(i) SEQUENCE CHARACTERISTICS:
        (A) LENGTH: 1829 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Region
        (B) LOCATION: 1
        (D) OTHER INFORMATION: /note= "Corresponds to position -1 of
            2c8 of figure 2."

(xi) SEQUENCE DESCRIPTION: SEQ ID NO:8:

AATGGAACCT TTTGTGGTCC TGGTGCTGTG TCTCTCTTTT ATGCTTCTCT TTTCACTCTG      60

GAGACAGAGC TGTAGGAGAA GGAAGCTCCC TCCTGGCCCC ACTCCTCTTC CTATTATTGG     120

AAATATGCTA CAGATAGATG TTAAGGACAT CTGCAAATCT TTCACCAATT TCTCAAAAGT     180

CTATGGTCCT GTGTTCACCG TGTATTTTGG CATGAATCCC ATAGTGGTGT TCATGGATA      240

TGAGGCAGTG AAGGAAGCCC TGATTGATAA TGGAGAGGAG TTTTCTGGAA GAGGCAATTC     300

CCCAATATCT CAAAGAATTA CTAAAGGACT TGGAATCATT TCCAGCAATG AAAGAGATG      360

GAAGGAGATC CGGCGTTTCT CCCTCACAAA CTTGCGGAAT TTTGGGATGG GGAAGAGGAG     420

CATTGAGGAC CGTGTTCAAG AGGAAGCTCA CTGCCTTGTG GAGGAGTTGA GAAAAACCAA     480

GGCTTCACCC TGTGATCCCA CTTTCATCCT GGGCTGTGCT CCCTGCAATG TGATCTGCTC     540

CGTTGTTTTC CAGAAACGAT TGATTATAA AGATCAGAAT TTTCTCACCC TGATGAAAAG      600

ATTCAATGAA AACTTCAGGA TTCTGAACTC CCCATGGATC CAGGTCTGCA ATAATTTCCC     660

TCTACTCATT GATTGTTTCC CAGGAACTCA CAACAAAGTG CTTAAAAATG TTGCTCTTAC     720

ACGAAGTTAC ATTAGGGAGA AAGTAAAAGA ACACCAAGCA TCACTGGATG TTAACAATCC     780

TCGGGACTTT ATGGATTGCT TCCTGATCAA AATGGAGCAG GAAAAGGACA ACCAAAAGTC     840

AGAATTCAAT ATTGAAAACT TGGTTGGCAC TGTAGCTGAT CTATTTGTTG CTGGAACAGA     900

GACAACAAGC ACCACTCTGA GATATGGACT CCTGCTCCTG CTGAAGCACC CAGAGGTCAC     960

AGCTAAAGTC CAGGAAGAGA TTGATCATGT AATTGGCAGA CACAGGAGCC CCTGCATGCA    1020

GGATAGGAGC CACATGCCTT ACACTGATGC TGTAGTGCAC GAGATCCAGA GATACAGTGA    1080

CCTTGTCCCC ACCGGTGTGC CCCATGCAGT GACCACTGAT ACTAAGTTCA GAAACTACCT    1140

CATCCCCAAG GGCACAACCA TAATGGCATT ACTGACTTCC GTGCTACATG ATGACAAAGA    1200

ATTTCCTAAT CCAAATATCT TGACCCTGG CCACTTTCTA GATAAGAATG GCAACTTTAA     1260

GAAAAGTGAC TACTTCATGC CTTTCTCAGC AGGAAAACGA ATTTGTGCAG GAGAAGGACT    1320

TGCCCGCATG GAGCTATTTT TATTTCTAAC CACAATTTTA CAGAACTTTA ACCTGAAATC    1380

TGTTGATGAT TTAAAGAACC TCAATACTAC TGCAGTTACC AAAGGGATTG TTTCTCTGCC    1440

ACCCTCATAC CAGATCTGCT TCATCCCTGT CTGAAGAATG CTAGCCCATC TGGCTGCTGA    1500

TCTGCTATCA CCTGCAACTC TTTTTTTATC AAGGACATTC CCACTATTAT GTCTTCTCTG    1560

ACCTCTCATC AAATCTTCCC ATTCACTCAA TATCCCATAA GCATCCAAAC TCCATTAAGG    1620

AGAGTTGTTC AGGTCACTGC ACAAATATAT CTGCAATTAT TCATACTCTG TAACACTTGT    1680

ATTAATTGCT GCATATGCTA ATACTTTTCT AATGCTGACT TTTTAATATG TTATCACTGT    1740
```

```
AAAACACAGA AAAGTGATTA ATGAATGATA ATTTAGTCCA TTTCTTTTGT GAATGTGCTA    1800

AATAAAAAGT GTTATTAATT GCTGGTTCA                                    1829

(2) INFORMATION FOR SEQ ID NO:9:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Met Asp Ser Leu Val Val Leu Val Leu Cys Leu Ser Cys Leu Leu Leu
    1               5                   10                  15

Leu Ser Leu Trp Arg Gln Ser Ser Gly Arg Gly Lys Leu Pro Pro Gly
                    20                  25                  30

Pro Thr Pro Leu Pro Val Ile Gly Asn Ile Leu Gln Ile Gly Ile Lys
                35                  40                  45

Asp Ile Ser Lys Ser Leu Thr Asn Leu Ser Lys Val Tyr Gly Pro Val
    50                  55                  60

Phe Thr Leu Tyr Phe Gly Leu Lys Pro Ile Val Val Leu His Gly Tyr
    65                  70                  75                  80

Glu Ala Val Lys Glu Ala Leu Ile Asp Leu Gly Glu Glu Phe Ser Gly
                    85                  90                  95

Arg Gly Ile Phe Pro Leu Ala Glu Arg Ala Asn Arg Gly Phe Gly Ile
                    100                 105                 110

Val Phe Ser Asn Gly Lys Lys Trp Lys Glu Ile Arg Arg Phe Ser Leu
                    115                 120                 125

Met Thr Leu Arg Asn Phe Gly Met Gly Lys Arg Ser Ile Glu Asp Arg
    130                 135                 140

Val Gln Glu Glu Ala Arg Cys Leu Val Glu Glu Leu Arg Lys Thr Lys
    145                 150                 155                 160

Ala Ser Pro Cys Asp Pro Thr Phe Ile Leu Gly Cys Ala Pro Cys Asn
                    165                 170                 175

Val Ile Cys Ser Ile Ile Phe His Lys Arg Phe Asp Tyr Lys Asp Gln
                    180                 185                 190

Gln Phe Leu Asn Leu Met Glu Lys Leu Asn Glu Asn Ile Lys Ile Leu
                    195                 200                 205

Ser Ser Pro Trp Ile Gln Ile Cys Asn Asn Phe Ser Pro Ile Ile Asp
    210                 215                 220

Tyr Phe Pro Gly Thr His Asn Lys Leu Leu Lys Asn Val Ala Phe Met
    225                 230                 235                 240

Lys Ser Tyr Ile Leu Glu Lys Val Lys Glu His Gln Glu Ser Met Asp
                    245                 250                 255

Met Asn Asn Pro Gln Asp Phe Ile Asp Cys Phe Leu Met Lys Met Glu
                    260                 265                 270

Lys Glu Lys His Asn Gln Pro Ser Glu Phe Thr Ile Glu Ser Leu Glu
                    275                 280                 285

Asn Thr Ala Val Asp Leu Phe Gly Ala Gly Thr Glu Thr Thr Ser Thr
    290                 295                 300

Thr Leu Arg Tyr Ala Leu Leu Leu Leu Lys His Pro Glu Val Thr
    305                 310                 315                 320

Ala Lys Val Gln Glu Glu Ile Glu Arg Val Ile Gly Arg Asn Arg Ser
                    325                 330                 335
```

```
              Pro Cys Met Gln Asp Arg Ser His Met Pro Tyr Thr Asp Ala Val Val
                      340                 345                 350

His Glu Val Gln Arg Tyr Ile Asp Leu Leu Pro Thr Ser Leu Pro His
                      355                 360                 365

Ala Val Thr Cys Asp Ile Lys Phe Arg Asn Tyr Leu Ile Pro Lys Gly
                      370                 375                 380

Thr Thr Ile Leu Ile Ser Leu Thr Ser Val Leu His Asp Asn Lys Glu
              385                 390                 395                 400

Phe Pro Asn Pro Glu Met Phe Asp Pro His His Phe Leu Asp Glu Gly
                              405                 410                 415

Gly Asn Phe Lys Lys Ser Lys Tyr Phe Met Pro Phe Ser Ala Gly Lys
                              420                 425                 430

Arg Ile Cys Val Gly Glu Ala Leu Ala Gly Met Glu Leu Phe Leu Phe
                      435                 440                 445

Leu Thr Ser Ile Leu Gln Asn Phe Asn Leu Lys Ser Leu Val Asp Pro
                      450                 455                 460

Lys Asn Leu Asp Thr Thr Pro Val Val Asn Gly Phe Ala Ser Val Pro
              465                 470                 475                 480

Pro Phe Tyr Gln Leu Cys Phe Ile Pro Val
                              485                 490

(2) INFORMATION FOR SEQ ID NO:10:

(i) SEQUENCE CHARACTERISTICS:
          (A) LENGTH: 1852 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: Region
          (B) LOCATION: 1..10
          (D) OTHER INFORMATION: /note= "Corresponds to positions -10 to
              -1 for 65 of Figure 2."

(xi) SEQUENCE DESCRIPTION: SEQ ID NO:10:

GAAGGCTTCA ATGGATTCTC TTGTGGTCCT TGTGCTCTGT CTCTCATGTT TGCTTCTCCT      60

TTCACTCTGG AGACAGAGCT CTGGGAGAGG AAAACTCCCT CCTGGCCCCA CTCCTCTCCC     120

AGTGATTGGA AATATCCTAC AGATAGGTAT TAAGGACATC AGCAAATCCT TAACCAATCT     180

CTCAAAGGTC TATGGCCCTG TGTTCACTCT GTATTTTGGC CTGAAACCCA TAGTGGTGCT     240

GCATGGATAT GAAGCAGTGA AGGAAGCCCT GATTGATCTT GGAGAGGAGT TTTCTGGAAG     300

AGGCATTTTC CCACTGGCTG AAAGAGCTAA CAGAGGATTT GGAATTGTTT TCAGCAATGG     360

AAAGAAATGG AAGGAGATCC GGCGTTTCTC CCTCATGACG CTGCGGAATT TGGGATGGG     420

GAAGAGGAGC ATTGAGGACC GTGTTCAAGA GGAAGCCCGC TGCCTTGTGG AGGAGTTGAG     480

AAAAACCAAG GCCTCACCCT GTGATCCCAC TTTCATCCTG GGCTGTGCTC CCTGCAATGT     540

GATCTGCTCC ATTATTTTCC ATAAACGTTT TGATTATAAA GATCAGCAAT TTCTTAACTT     600

AATGGAAAAG TTGAATGAAA ACATCAAGAT TTTGAGCAGC CCCTGGATCC AGATCTGCAA     660

TAATTTTTCT CCTATCATTG ATTACTTCCC GGGAACTCAC AACAAATTAC TTAAAAACGT     720

TGCTTTTATG AAAAGTTATA TTTTGGAAAA AGTAAAAGAA CACCAAGAAT CAATGGACAT     780

GAACAACCCT CAGGACTTTA TTGATTGCTT CCTGATGAAA ATGGAGAAGG AAAAGCACAA     840

CCAACCATCT GAATTTACTA TTGAAAGCTT GGAAAACACT GCAGTTGACT TGTTTGGAGC     900
```

```
TGGGACAGAG ACGACAAGCA CAACCCTGAG ATATGCTCTC CTTCTCCTGC TGAAGCACCC        960

AGAGGTCACA GCTAAAGTCC AGGAAGAGAT TGAACGTGTG ATTGGCAGAA ACCGGAGCCC       1020

CTGCATGCAA GACAGGAGCC ACATGCCCTA CACAGATGCT GTGGTGCACG AGGTCCAGAG       1080

ATACATTGAC CTTCTCCCCA CCAGCCTGCC CCATGCAGTG ACCTGTGACA TTAAATTCAG       1140

AAACTATCTC ATTCCCAAGG GCACAACCAT ATTAATTTCC CTGACTTCTG TGCTACATGA       1200

CAACAAAGAA TTTCCCAACC CAGAGATGTT TGACCCTCAT CACTTTCTGG ATGAAGGTGG       1260

CAATTTTAAG AAAAGTAAAT ACTTCATGCC TTTCTCAGCA GGAAAACGGA TTTGTGTGGG       1320

AGAAGCCCTG GCCGGCATGG AGCTGTTTTT ATTCCTGACC TCCATTTTAC AGAACTTTAA       1380

CCTGAAATCT CTGGTTGACC CAAAGAACCT TGACACCACT CCAGTTGTCA ATGGATTTGC       1440

CTCTGTGCCG CCCTTCTACC AGCTGTGCTT CATTCCTGTC TGAAGAAGAG CAGATGGCCT       1500

GGCTGCTGCT GTGCAGTCCC TGCAGCTCTC TTTCCTCTGG GGCATTATCC ATCTTTCACT       1560

ATCTGTAATG CCTTTTCTCA CCTGTCATCT CACATTTTCC CTTCCCTGAA GATCTAGTGA       1620

ACATTCGACC TCCATTACGG AGAGTTTCCT ATGTTTCACT GTGCAAATAT ATCTGCTATT       1680

CTCCATACTC TGTAACAGTT GCATTGACTG TCACATAATG CTCATACTTA TCTAATGTTG       1740

AGTTATTAAT ATGTTATTAT TAAATAGAGA AATATGATTT GTGTATTATA ATTCAAAGGC       1800

ATTTCTTTTC TGCATGTTCT AAATAAAAAG CATTATTATT TGCTGAAAAA AA              1852

(2) INFORMATION FOR SEQ ID NO:11:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Asp Pro Ala Val Ala Leu Val Leu Cys Leu Ser Cys Leu Phe Leu
    1               5                   10                  15

Leu Ser Leu Trp Arg Gln Ser Ser Gly Arg Gly Arg Leu Pro Ser Gly
                20                  25                  30

Pro Thr Pro Leu Pro Ile Ile Gly Asn Ile Leu Gln Leu Asp Val Lys
                35                  40                  45

Asp Met Ser Lys Ser Leu Thr Asn Phe Ser Lys Val Tyr Gly Pro Val
    50                  55                  60

Phe Thr Val Tyr Phe Gly Leu Lys Pro Ile Val Val Leu His Gly Tyr
    65                  70                  75                  80

Glu Ala Val Lys Glu Ala Leu Ile Asp His Gly Glu Glu Phe Ser Gly
                    85                  90                  95

Arg Gly Ser Phe Pro Val Ala Glu Lys Val Asn Lys Gly Leu Gly Ile
                100                 105                 110

Leu Phe Ser Asn Gly Lys Arg Trp Lys Glu Ile Arg Arg Phe Cys Leu
                115                 120                 125

Met Thr Leu Arg Asn Phe Gly Met Gly Lys Arg Ser Ile Glu Asp Arg
                130                 135                 140

Val Gln Glu Glu Ala Arg Cys Leu Val Glu Glu Leu Arg Lys Thr Asn
    145                 150                 155                 160

Ala Ser Pro Cys Asp Pro Thr Phe Ile Leu Gly Cys Ala Pro Cys Asn
                    165                 170                 175

Val Ile Cys Ser Val Ile Phe His Asp Arg Phe Asp Tyr Lys Asp Gln
                    180                 185                 190
```

```
Arg Phe Leu Asn Leu Met Glu Lys Phe Asn Glu Asn Leu Arg Ile Leu
            195                 200                 205
Ser Ser Pro Trp Ile Gln Val Cys Asn Asn Phe Pro Ala Leu Ile Asp
        210                 215                 220
Tyr Leu Pro Gly Ser His Asn Lys Ile Ala Glu Asn Phe Ala Tyr Ile
225                 230                 235                 240
Lys Ser Tyr Val Leu Glu Arg Ile Lys Glu His Gln Ser Leu Asp
                245                 250                 255
Met Asn Ser Ala Arg Asp Phe Ile Asp Cys Phe Leu Ile Lys Met Glu
                260                 265                 270
Gln Glu Lys His Asn Gln Gln Ser Glu Phe Thr Val Glu Ser Leu Ile
            275                 280                 285
Ala Thr Val Thr Asp Met Phe Gly Ala Gly Thr Glu Thr Thr Ser Thr
        290                 295                 300
Thr Leu Arg Tyr Gly Leu Leu Leu Leu Lys Tyr Pro Glu Val Thr
305                 310                 315                 320
Ala Lys Val Gln Glu Glu Ile Glu Cys Val Val Gly Arg Asn Arg Ser
                325                 330                 335
Pro Cys Met Gln Asp Arg Ser His Met Pro Tyr Thr Asp Ala Val Val
                340                 345                 350
His Glu Ile Gln Arg Tyr Ile Asp Leu Leu Pro Thr Asn Leu Pro His
            355                 360                 365
Ala Val Thr Cys Asp Val Lys Phe Lys Asn Tyr Leu Ile Pro Lys Gly
        370                 375                 380
Met Thr Ile Ile Thr Ser Leu Thr Ser Val Leu His Asn Asp Lys Glu
385                 390                 395                 400
Phe Pro Asn Pro Glu Met Phe Asp Pro Gly His Phe Leu Asp Lys Ser
                405                 410                 415
Gly Asn Phe Lys Lys Ser Asp Tyr Phe Met Pro Phe Ser Ala Gly Lys
                420                 425                 430
Arg Met Cys Met Gly Glu Gly Leu Ala Arg Met Glu Leu Phe Leu Phe
            435                 440                 445
Leu Thr Thr Ile Leu Gln Asn Phe Asn Leu Lys Ser Gln Val Asp Pro
        450                 455                 460
Lys Asp Ile Asp Ile Thr Pro Ile Ala Asn Ala Phe Gly Arg Val Pro
465                 470                 475                 480
Pro Leu Tyr Gln Leu Cys Phe Ile Pro Val
                485                 490
```

(2) INFORMATION FOR SEQ ID NO:12:

(i) SEQUENCE CHARACTERISTICS:
        (A) LENGTH: 2258 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Region
        (B) LOCATION: 1..18
        (D) OTHER INFORMATION: /note= "Corresponds to positions -18 to
           -1 for 6b of Figure 2."

(xi) SEQUENCE DESCRIPTION: SEQ ID NO:12:

```
AGTGAAAGCC CGCAGTTGTC TTACTAAGAA GAGAAGCCTT CAATGGATCC AGCTGTGGCT        60

CTGGTGCTCT GTCTCTCCTG TTTGTTTCTC CTTTCACTCT GGAGGCAGAG CTCTGGAAGA       120
```

```
GGGAGGCTCC CGTCTGGCCC CACTCCTCTC CCGATTATTG GAAATATCCT GCAGTTAGAT      180

GTTAAGGACA TGAGCAAATC CTTAACCAAT TTCTCAAAAG TCTATGGCCC TGTGTTCACT      240

GTGTATTTTG GCCTGAAGCC CATTGTGGTG TTGCATGGAT ATGAAGCAGT GAAGGAGGCC      300

CTGATTGATC ATGGAGAGGA GTTTTCTGGA AGAGGAAGTT TTCCAGTGGC TGAAAAAGTT      360

AACAAAGGAC TTGGAATCCT TTTCAGCAAT GGAAAGAGAT GGAAGGAGAT CCGGCGTTTC      420

TGCCTCATGA CTCTGCGGAA TTTTGGGATG GGGAAGAGGA GCATCGAGGA CCGTGTTCAA      480

GAGGAAGCCC GCTGCCTTGT GGAGGAGTTG AGAAAAACCA ATGCCTCACC CTGTGATCCC      540

ACTTTCATCC TGGGCTGTGC TCCCTGCAAT GTGATCTGCT CTGTTATTTT CCATGATCGA      600

TTTGATTATA AAGATCAGAG GTTTCTTAAC TTGATGGAAA AATTCAATGA AAACCTCAGG      660

ATTCTGAGCT CTCCATGGAT CCAGGTCTGC AATAATTTCC CTGCTCTCAT CGATTATCTC      720

CCAGGAAGTC ATAATAAAAT AGCTGAAAAT TTTGCTTACA TTAAAAGTTA TGTATTGGAG      780

AGAATAAAAG AACATCAAGA ATCCCTGGAC ATGAACAGTG CTCGGGACTT TATTGATTGT      840

TTCCTGATCA AAATGGAACA GGAAAAGCAC AATCAACAGT CTGAATTTAC TGTTGAAAGC      900

TTGATAGCCA CTGTAACTGA TATGTTTGGG GCTGGAACAG AGACAACGAG CACCACTCTG      960

AGATATGGAC TCCTGCTCCT GCTGAAGTAC CCAGAGGTCA CAGCTAAAGT CCAGGAAGAG     1020

ATTGAATGTG TAGTTGGCAG AAACCGGAGC CCCTGTATGC AGGACAGGAG TCACATGCCC     1080

TACACAGATG CTGTGGTGCA CGAGATCCAG AGATACATTG ACCTCCTCCC CACCAACCTG     1140

CCCCATGCAG TGACCTGTGA TGTTAAATTC AAAAACTACC TCATCCCCAA GGGCATGACC     1200

ATAATAACAT CCCTGACTTC TGTGCTGCAC AATGACAAAG AATTCCCCAA CCCAGAGATG     1260

TTTGACCCTG GCCACTTTCT GGATAAGAGT GGCAACTTTA AGAAAAGTGA CTACTTCATG     1320

CCTTTCTCAG CAGGAAAACG GATGTGTATG GGAGAGGGCC TGGCCCGCAT GGAGCTGTTT     1380

TTATTCCTGA CCACCATTTT GCAGAACTTT AACCTGAAAT CTCAGGTTGA CCCAAAGGAT     1440

ATTGACATCA CCCCCATTGC CAATGCATTT GGTCGTGTGC CACCCTTGTA CCAGCTCTGC     1500

TTCATTCCTG TCTGAAGAAG GGCAGATAGT TTGGCTGCTC CTGTGCTGTC ACCTGCAATT     1560

CTCCCTTATC AGGGCCATTG GCCTCTCCCT TCTCTCTATG AGGGATATTT TCTCTGACTT     1620

GTCAATCCAC ATCTTCCCAT TCCCTCAAGA TCCAATGAAC ATCCAACCTC CATTAAAGAG     1680

AGTTTCTTGG GTCACTTCCT AAATATATCT GCTATTCTCC ATACTCTGTA TCACTTGTAT     1740

TGACCACCAC ATATGCTAAT ACCTATCTAC TGCTGAGTTC AGTATGTT ATCACTATAA      1800

AACAAAGAAA ATGATTAAT AAATGACAAT TCAGAGCCAT TTATTCTCTG CATGCTCTAG     1860

ATAAAAATGA TTATTATTTA CTGGGTCAGT TCTTAGATTT CTTTCTTTTG AGTAAAATGA     1920

AAGTAAGAAA TGAAAGAAAA TAGAATGTGA AGAGGCTGTG CTGGCCCTCA TAGTGTTAAG     1980

CACAAAAAGG GAGAAAGGTA AGAGGGTAGG AAAGCTGTTT TAGCTAAATG CCACCTAGAG     2040

TTATTGGAGG TCTGAATTTG GAAAAAAAAA CTATGTCCAG GAGCAGCTGT AACCTGTAGG     2100

GAAATAATGG AACAATCATC CATAAGAGGG ATGAACATTA AGTGTTTGAA TTCATGCTCT     2160

GCTTTTGTGT TACTGTAAAC ACAAGATCAA GATTTGGATA ATCTTTTTCC TTTGTGTTTC     2220

CAACTTAGAT CATGTCTAAA TATATGCTTT CATATGGC                            2258
```

(2) INFORMATION FOR SEQ ID NO:13:

(i) SEQUENCE CHARACTERISTICS:
        (A) LENGTH: 490 amino acids
        (B) TYPE: amino acid
        (C) STRANDEDNESS: single (D) TOPOLOGY: linear (ii) MOLECULE TYPE: protein (iii) HYPOTHETICAL: YES (xi) SEQUENCE DESCRIPTION: SEQ ID NO:13:

```
Met Asp Pro Xaa Val Val Leu Val Leu Cys Leu Ser Cys Leu Leu Leu
  1               5                  10                  15

Leu Ser Leu Trp Arg Gln Ser Ser Gly Arg Gly Lys Leu Pro Pro Gly
             20                  25                  30

Pro Thr Pro Leu Pro Xaa Ile Gly Asn Ile Leu Gln Ile Asp Xaa Lys
         35                  40                  45

Asp Ile Ser Lys Ser Leu Thr Asn Xaa Ser Lys Val Tyr Gly Pro Val
 50                  55                  60

Phe Thr Xaa Tyr Phe Gly Leu Lys Pro Ile Val Val Leu His Gly Tyr
 65                  70                  75                  80

Glu Ala Val Lys Glu Ala Leu Ile Asp Leu Gly Glu Glu Phe Ser Gly
             85                  90                  95

Arg Gly Xaa Phe Pro Leu Ala Glu Arg Ala Asn Xaa Gly Xaa Gly Ile
        100                 105                 110

Val Phe Ser Asn Gly Lys Arg Trp Lys Glu Ile Arg Arg Phe Ser Leu
        115                 120                 125

Met Thr Leu Arg Asn Phe Gly Met Gly Lys Arg Ser Ile Glu Asp Arg
130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Xaa Ile Phe His Lys Arg Phe Asp Tyr Lys Asp Gln
                180                 185                 190

Gln Phe Leu Asn Leu Met Glu Lys Xaa Asn Glu Asn Ile Arg Ile Leu
            195                 200                 205

Ser Ser Pro Trp Ile Gln Xaa Cys Asn Asn Phe Pro Xaa Xaa Ile Asp
        210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Xaa Asp
                245                 250                 255

Met Asn Asn Pro Arg Asp Phe Ile Asp Cys Phe Leu Ile Lys Met Glu
            260                 265                 270

Xaa Glu Lys His Asn Gln Gln Ser Glu Phe Thr Ile Glu Ser Leu Xaa
        275                 280                 285

Xaa Thr Xaa Xaa Asp Leu Phe Gly Ala Gly Thr Glu Thr Thr Ser Thr
        290                 295                 300

Thr Leu Arg Tyr Xaa Leu Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Ser His Met Pro Tyr Thr Asp Ala Val Val
            340                 345                 350

His Glu Xaa Gln Arg Tyr Ile Asp Leu Leu Pro Thr Ser Leu Pro His
        355                 360                 365

Ala Val Thr Cys Asp Val Lys Phe Arg Asn Tyr Leu Ile Pro Lys Gly
370                 375                 380
```

```
    Thr Thr Ile Leu Thr Ser Leu Thr Ser Val Leu His Asp Xaa Lys Glu
    385                 390                 395                 400

Phe Pro Asn Pro Glu Met Phe Asp Pro Gly His Phe Leu Asp Xaa Gly
                    405                 410                 415

Gly Asn Phe Lys Lys Ser Asp Tyr Phe Met Pro Phe Ser Ala Gly Lys
                420                 425                 430

Arg Ile Cys Val Gly Glu Gly Leu Ala Arg Met Glu Leu Phe Leu Phe
            435                 440                 445

Leu Thr Thr Ile Leu Gln Asn Phe Asn Leu Lys Ser Leu Val Asp Pro
        450                 455                 460

Lys Xaa Leu Asp Thr Thr Pro Val Val Asn Gly Phe Ala Ser Val Pro
    465                 470                 475                 480

Pro Phe Tyr Gln Leu Cys Phe Ile Pro Val
                485                 490
```

(2) INFORMATION FOR SEQ ID NO:14:

(i) SEQUENCE CHARACTERISTICS:
        (A) LENGTH: 1892 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: Region
        (B) LOCATION: 1..41
        (D) OTHER INFORMATION: /note= "Corresponds to positions -41 to
            -1 for 2c of Figure 2."

(xi) SEQUENCE DESCRIPTION: SEQ ID NO:14:

```
AGTGAAAGCC CGCAGTTGTC TTACTAAGAA GAGAAGNCTT CAATGGATCC TNTTGTGGTC      60

CTNGTGCTCT GTCTCTCATG TTTGCTTCTC CTTTCACTCT GGAGACAGAG CTCTGGGAGA     120

GGNAANCTCC CTCCTGGCCC CACTCCTCTC CCANTNATTG GAAATATCCT ACAGATAGAT     180

NTTAAGGACA TCAGCAAATC CTTAACCAAT NTCTCAAAAG TCTATGGCCC TGTGTTCACT     240

NTGTATTTTG GCCTGAAACC CATAGTGGTG NTGCATGGAT ATGAAGCAGT GAAGGAAGCC     300

CTGATTGATC NTGGAGAGGA GTTTTCTGGA AGAGGCANTT TCCCACTGGC TGAAAGAGNT     360

AACANAGGAN TTGGAATCGT TTTCAGCAAT GGAAAGAGAT GGAAGGAGAT CCGGCGTTTC     420

TCCCTCATGA CGCTGCGGAA TTTTGGGATG GGAAGAGGA GCATTGAGGA CCGTGTTCAA     480

GAGGAAGCCC GCTGCCTTGT GGAGGAGTTG AGAAAAACCA AGGCCTCACC CTGTGATCCC     540

ACTTTCATCC TGGGCTGTGC TCCCTGCAAT GTGATCTGCT CCNTTATTTT CCATAAACGN     600

TTTGATTATA AGATCAGNA ATTTCTTAAC TTGATGGAAA AATTNAATGA AAACATCAGG     660

ATTCTGAGCN CCCCNTGGAT CCAGNTCTGC AATAATTTNC CTCCTNTCAT TGATTATTTC     720

CCNGGAACTC ANAACAAATT ACTTAAAAAN GTTGCTTTTA TGAAAAGTTA TATTTTGGAG     780

AAAGTAAAAG AACACCAAGA ATCANTGGAC ATGAACAANC CTCGGGACTT TATTGATTGC     840

TTCCTGATCA AAATGGAGNA GGAAAAGCAC AACCAACAGT CTGAATTTAC TATTGAAAGC     900

TTGGTANNCA CTGNAGCTGA NTTGTTTGGA GCTGGNACAG AGACAACAAG CACNACNCTG     960

AGATATGNNC TCCTNCTCCT GCTGAAGCAC CCAGAGGTCA CAGCTAAAGT CCAGGAAGAG    1020

ATTGAACGTG TAATTGGCAG AAACCGGAGC CCCTGCATGC AGGACAGGAG CCACATGCCC    1080

TACACAGATG CTGTGGTGCA CGAGNTCCAG AGATACATTG ACCTNCTCCC CACCAGCCTG    1140
```

-continued

```
CCCCATGCAG TGACCTGTGA NNTTAAATTC AGAAACTACC TCATNCCCAA GGGCACAACC    1200

ATANTAACNT CCCTGACTTC TGTGCTACAT GANNACAAAG AATTTCCCAA CCCAGAGATG    1260

TTTGACCCTN GNCACTTTCT GGATNANNGT GGCAANTTTA AGAAAAGTNA CTACTTCATG    1320

CCTTTCTCAG CAGGAAAACG GATTTGTGTG GGAGANGGCC TGGCCCGCAT GGAGCTGTTT    1380

TTATTCCTGA CCNCCATTTT ACAGAACTTT AACCTGAAAT CTCTGGTTGA CCCAAANGAC    1440

CTTGACACCA CTCCAGTTGN CAATGGATTT GCTTCTGTGC CNCCCTTCTA CCAGCTNTGC    1500

TTCATTCCTG TCTGAAGAAG GGCAGATGGT CTGGCTGCTN CTGTGCTGTC NCNNNNNNTN    1560

NNTTTNNTCT GGGGCAATTT CCNTCTTNCA TNNNTNTTNN TGCNNTTTNT CATCTGNCAT    1620

CTCACANTNC NNCTTCCCTT ANCATCNAGN NACCATTNAN NNNCAATNTC CAAGAGNGTG    1680

NNTTTNTTNN CTNTCCACCT ANATCTATCN NTNNNNCTNC TNTNTNTNNA TNACTTTGAT    1740

TGTCCNCTAN TGATGNTAAT TNTTTAATAT TGNNTTATTG NNANNNTNTT ATNANTNANA    1800

AANAAATGAT AATTNTNTNN AAATNNNAAG TCANTGCNNT TNANNATNTN CNNAATAAAA    1860

AGCATTATTA TTTGCTGAAA AAAGTCAGT TC                                  1892
```

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
GCAAGCTTAA AAAATGGATC CAGCTGTGGC TCT                                 33
```

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GCAAGCTTGC CAAACTATCT GCCCTTCT                                       28
```

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
ACTTTTCAAT GTAAGCAAAT                                                20
```

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TTAGTAATTC TTTGAGATAT                                                  20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CTGTTAGCTC TTTCAGCCAG                                                  20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GGAGCACAGC CCAGGATGAA                                                  20

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GCAAGCTTAA AAAATGGATC CAGCTGTGGC TCT                                   33

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GCAAGCTTGC CAAACTATCT GCCCTTCT                                         28

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:23:

TGGCCCTGAT AAGGGAGAAT                                                  20

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:24:

ATCCAGAGAT ACATTGACCT C                       21

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:25:

CCATGAAGTG ACCTGTGATG                       20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:26:

AAAGATGGAT AATGCCCCAG                       20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:27:

GAAGGAGATC CGGCGTTTCT                       20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:28:

GGCGTTTCTC CCTCATGACG                       20

(2) INFORMATION FOR SEQ ID NO:29:

(i) SEQUENCE CHARACTERISTICS:

(A) LENGTH: 14 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:29:

TTGTCATTGT GCAG                                                                14

(2) INFORMATION FOR SEQ ID NO:30:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:30:

CACATGCCCT ACACA                                                               15

(2) INFORMATION FOR SEQ ID NO:31:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:31:

TGACGCTGCG GAATT                                                               15

(2) INFORMATION FOR SEQ ID NO:32:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:32:

GGACTTTATT GATTG                                                               15

(2) INFORMATION FOR SEQ ID NO:33:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:33:

ATGATTCTCT TGTGGTCCT                                                           19

(2) INFORMATION FOR SEQ ID NO:34:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:34:

AAAGATGGAT AATGCCCCCA G                                          21

(2) INFORMATION FOR SEQ ID NO:35:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:35:

GCAAGCTTAA AAAAATGGAA CCTTTTGTGG TCCT                            34

(2) INFORMATION FOR SEQ ID NO:36:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:36:

GCAAGCTTGC CAGATGGGCT AGCATTCT                                   28

(2) INFORMATION FOR SEQ ID NO:37:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:37:

GCAAGCTTAA AAAAATGGAT TCTCTTGTGG TCCT                            34

(2) INFORMATION FOR SEQ ID NO:38:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:38:

GCAAGCTTGC CAGGCCATCT GCTCTTCT                                   28

(2) INFORMATION FOR SEQ ID NO:39:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:39:

GCAAGCTTAA AAAAATGGAT TCTCTTGTGG TCCT                            34

(2) INFORMATION FOR SEQ ID NO:40:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:40:

GCAAGCTTGC CAGACCATCT GTGCTTCT                                  28

(2) INFORMATION FOR SEQ ID NO:41:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligo)

(xi) SEQUENCE DESCRIPTION: SEQ ID NO:41:

AGCTTAAAAA AATG                                                    14

(2) INFORMATION FOR SEQ ID NO:42:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligo)

(xi) SEQUENCE DESCRIPTION: SEQ ID NO:42:

GATCCATTTT TTTA                                                    14

(2) INFORMATION FOR SEQ ID NO:43:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:43:

Cys Ile Asp Tyr Leu Pro Gly Ser His Asn Lys Ile Ala Glu Asn Phe
1               5                 10                15

Ala (2) INFORMATION FOR SEQ ID NO:44:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:44:

Cys Leu Ala Phe Met Glu Ser Asp Ile Leu Glu Lys Val Lys
1               5                 10

(2) INFORMATION FOR SEQ ID NO:45:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..283

(xi) SEQUENCE DESCRIPTION: SEQ ID NO:45:

```
A TTG AAT GAA AAC ATC AGG ATT GTA AGC ACC CCC TGG ATC CAG ATA         46
  Leu Asn Glu Asn Ile Arg Ile Val Ser Thr Pro Trp Ile Gln Ile
   1               5                  10                  15

TGC AAT AAT TTT CCC ACT ATC ATT GAT TAT TTC CCG GGA ACC CAT AAC        94
Cys Asn Asn Phe Pro Thr Ile Ile Asp Tyr Phe Pro Gly Thr His Asn
                 20                  25                  30

AAA TTA CTT AAA AAC CTT GCT TTT ATG GAA AGT GAT ATT TTG GAG AAA       142
Lys Leu Leu Lys Asn Leu Ala Phe Met Glu Ser Asp Ile Leu Glu Lys
             35                  40                  45

GTA AAA GAA CAC CAA GAA TCG ATG GAC ATC AAC AAC CCT CGG GAC TTT       190
Val Lys Glu His Gln Glu Ser Met Asp Ile Asn Asn Pro Arg Asp Phe
         50                  55                  60

ATT GAT TGC TTC CTG ATC AAA ATG GAG AAG GAA AAG CAA AAC CAA CAG       238
Ile Asp Cys Phe Leu Ile Lys Met Glu Lys Glu Lys Gln Asn Gln Gln
     65                  70                  75

TCT GAA TTC ACT ATT GAA AAC TTG GTA ATC ACT GCA GCT GAC TTA           283
Ser Glu Phe Thr Ile Glu Asn Leu Val Ile Thr Ala Ala Asp Leu
 80                  85                  90

C                                                                      284
```

(2) INFORMATION FOR SEQ ID NO:46:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:46:

```
Leu Asn Glu Asn Ile Arg Ile Val Ser Thr Pro Trp Ile Gln Ile Cys
 1               5                  10                  15

Asn Asn Phe Pro Thr Ile Ile Asp Tyr Phe Pro Gly Thr His Asn Lys
             20                  25                  30

Leu Leu Lys Asn Leu Ala Phe Met Glu Ser Asp Ile Leu Glu Lys Val
         35                  40                  45

Lys Glu His Gln Glu Ser Met Asp Ile Asn Asn Pro Arg Asp Phe Ile
     50                  55                  60

Asp Cys Phe Leu Ile Lys Met Glu Lys Glu Lys Gln Asn Gln Gln Ser
 65                  70                  75                  80

Glu Phe Thr Ile Glu Asn Leu Val Ile Thr Ala Ala Asp Leu
                 85                  90
```

(2) INFORMATION FOR SEQ ID NO:47:

(i) SEQUENCE CHARACTERISTICS:
        (A) LENGTH: 244 base pairs
        (B) TYPE: nucleic acid
        (C) STRANDEDNESS: single

```
        (D) TOPOLOGY: linear (ii) MOLECULE TYPE: cDNA (ix) FEATURE:
        (A) NAME/KEY: CDS
        (B) LOCATION: 44..103

(xi) SEQUENCE DESCRIPTION: SEQ ID NO:47:

ATTGAATGAA AACATCAGGA TTGTAAGCAC CCCCTGGATC CAG GAA CCC ATA ACA      55
                                                Glu Pro Ile Thr
                                                  1

AAT TAC TTA AAA ACC TTG CTT TTA TGG AAA GTG ATA TTT TGG AGA AAG     103
Asn Tyr Leu Lys Thr Leu Leu Leu Trp Lys Val Ile Phe Trp Arg Lys
  5              10                  15                  20

TAAAAGAACA CCAAGAATCG ATGGACATCA ACAACCCTCG GGACTTTATT GATTGCTTCC    163

TGATCAAAAT GGAGAAGGAA AAGCAAAACC AACAGTCTGA ATTCACTATT GAAAACTTGG    223

TAATCACTGC AGCTGACTTA C                                              244

(2) INFORMATION FOR SEQ ID NO:48:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:48:

Glu Pro Ile Thr Asn Tyr Leu Lys Thr Leu Leu Leu Trp Lys Val Ile
  1               5                  10                  15

Phe Trp Arg Lys
            20

(2) INFORMATION FOR SEQ ID NO:49:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..32

(ix) FEATURE:
        (A) NAME/KEY: exon
        (B) LOCATION: 33..83

(xi) SEQUENCE DESCRIPTION: SEQ ID NO:49:

TTTTAATTTA ATAAATTATT GTTTTCTCTT AGATATGCAA TAATTTTCCC ACTATCATTG     60

ATTATTTCCC GGGAACCCAT AAC                                            83

(2) INFORMATION FOR SEQ ID NO:50:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
```

(B) LOCATION: 1..72

(ix) FEATURE:
            (A) NAME/KEY: exon
            (B) LOCATION: 73..83

(xi) SEQUENCE DESCRIPTION: SEQ ID NO:50:

TTTTAATTTA ATAAATTATT GTTTTCTCTT AGATATGCAA TAATTTTCCC ACTATCATTG    60

ATTATTTCCA AGGAACCCAT AAC                                           83

(2) INFORMATION FOR SEQ ID NO:51:

(i) SEQUENCE CHARACTERISTICS:
            (A) LENGTH: 826 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:51:

ATGGTGATGT AGNAANTCAT NCCATCTTAT ATTTCNAGAG TGTAGAGGAG GATTGTTGNG    60

GAAGTAAGAG GNNTAAGATA GAGATGCNTT TATACTATCC CAAGCAGGGA TRAGTCTAGG   120

AAATGATTAT CGTCTTTGAT TCTCTTGTCA GRATTTTCTT TCTCMNATCT TGTATAATCA   180

GAGAATTACT ACACATGGAC AATRAARATT TCCCCNTCCA GATANACAAT ATATTTTATT   240

TATATTTATA GTTTTAAATT ACAACCAGAG CTTGGCATAT TGTATCTATA CCTTTAATAA   300

ATGCTTTTAA TTTAATAAAT TATTGTTTTC TCTTAGATAT GCAATAATTT TCCCACTATC   360

ATTGATTATT TCCCGGGAAC CCATAACAAA TTACTTAAAA ACCTTGCTTT TATGGAAAGT   420

GATATTTTGG AGAAAGTAAA AGAACACCAA GAATCGATGG ACATCAACAA CCCTCGGGAC   480

TTTATTGATT GCTTCCTGAT CAAAATGGAG AAGGTAAAAT GTTAACAAAA GCTTAGTTAT   540

GTGACTGCTT GCGTATKTGT GATTCATTGA CTAGTTGKGT GTTTACTACG GATGTTTAAC   600

AGGTCAAGGA GTAATGCTTG AGAAGCATAT TTAAGTTTTT ATTGTATGCA TGAATATCCA   660

GTAAGCATCA TAGAAAATGT AAAATTAANT TGTTAAATAA TTAGAATACA TAGAAGAAAT   720

TGTTTAGATA AATATNATCT ATCTGAACAA TAAGGATGTC AGGATAGGAA AAGCTCTGTT   780

TCTGCAGCTT CCAGTGGAGA TCAGCACAGG AGGGAACTTA TTTTTT                  826

(2) INFORMATION FOR SEQ ID NO:52:

(i) SEQUENCE CHARACTERISTICS:
            (A) LENGTH: 655 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 263..421

(xi) SEQUENCE DESCRIPTION: SEQ ID NO:52:

AGGGAAAAGA CAAATAGGCC GGGGATGNAA ATTTAGCATG TGAGCAACCT TANTTAACCA    60

GCTAGGCTGT AATTGNTAAT TCGAGANTAA TGTNAAAGTG ATGTGTTGAT TTTATGCATG   120

CCNNACTCNT TTTTGCTTTT AAGGGGAGTC ATAGGTAAGA TATTACTTAA AATTTCTAAA   180

CTATTATTAT CTGTTAACTA ATATGAAGTG TTTTATATCT AATGTTACT CATATTTTAA    240

AATTGTTTCC AATCATTTAG CT TCA CCC TGT GAT CCC ACT TTC ATC CTG GGC   292
                        Ser Pro Cys Asp Pro Thr Phe Ile Leu Gly

```
              1              5             10
TGT GCT CCC TGC AAT GTG ATC TGC TCC ATT ATT TTC CAG AAA CGT TTC      340
Cys Ala Pro Cys Asn Val Ile Cys Ser Ile Ile Phe Gln Lys Arg Phe
                15              20              25

GAT TAT AAA GAT CAG CAA TTT CTT AAC TTG ATG GAA AAA TTG AAT GAA      388
Asp Tyr Lys Asp Gln Gln Phe Leu Asn Leu Met Glu Lys Leu Asn Glu
            30              35              40

AAC ATC AGG ATT GTA AGC ACC CCC TGG ATC CAG GTAAGGACA AGTTTTGTGC     440
Asn Ile Arg Ile Val Ser Thr Pro Trp Ile Gln
            45              50

TTCCTGAGAA ACCACTTACA GTCTTTTTTT CTGGGAAATC CAAAATTCTA TATTGACCAA    500

GCCCTGAAGT ACATTTGTGA ATACTACAGT CTTGCCTAGA CAGCCATGGG GTGAATATCT    560

GGAAAAGATG GCAAAGNTCT TTATTTTATG CACAGGAAAT GAATATCCCA ATATAGATCA    620

GGCTTCTAAG CCCATTAGCT CCCTGATCAG TGTTT                               655
```

(2) INFORMATION FOR SEQ ID NO:53:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO:53:

```
Ser Pro Cys Asp Pro Thr Phe Ile Leu Gly Cys Ala Pro Cys Asn Val
 1               5                  10                  15

Ile Cys Ser Ile Ile Phe Gln Lys Arg Phe Asp Tyr Lys Asp Gln Gln
                20                  25                  30

Phe Leu Asn Leu Met Glu Lys Leu Asn Glu Asn Ile Arg Ile Val Ser
            35                  40                  45

Thr Pro Trp Ile Gln
        50
```

(2) INFORMATION FOR SEQ ID NO:54:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
ATGAAGTGTT TTATATCTAA TGTTTACTCA TATTTTAAAA TTGTTTCCAA TCATTTAGCT     60

TCACCCTGTG ATCCCACTTT CATCCTGGGC TGTGCTCCCT GCAATGTGAT CTGCTCCATT    120

ATTTTCCAGA AACGTTTCGA TTATAAAGAT CAGCAATTTC TTAACTTGAT GGAAAAATTG    180

AATGAAAACA TCAGGATTGT AAGCACCCCC TGAATCCAGG TAAGGACAAG TTTTGTGCTT    240

CCTGAGAAAC CACTTACAGT CTTTTTTTCT GGGAAATCCA AAATTCTATA TT            292
```

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:55:

AATTACAACC AGAGCTTGGC                                            20

(2) INFORMATION FOR SEQ ID NO:56:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:56:

TATCACTTTC CATAAAAGCA AG                                         22

(2) INFORMATION FOR SEQ ID NO:57:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:57:

TATTATCTGT TAACTAACTA ATATGA                                     26

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:58:

ACTTCAGGGC TTGGTCAATA                                            20

(2) INFORMATION FOR SEQ ID NO:59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:59:

ATTGAATGAA AACATCAGGA TTG                                        23

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:60:

GTAAGTCAGC TGCAGTGATT A                                          21

(2) INFORMATION FOR SEQ ID NO:61:

(i) SEQUENCE CHARACTERISTICS:
        (A) LENGTH: 826 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
ATGGTGATGT AGNAANTCAT NCCATCTTAT ATTTCNAGAG TGTAGAGGAG GATTGTTGNG      60

GAAGTAAGAG GNNTAAGATA GAGATGCNTT TATACTATCC CAAGCAGGGA TRAGTCTAGG     120

AAATGATTAT CGTCTTTGAT TCTCTTGTCA GRATTTTCTT TCTCMNATCT TGTATAATCA     180

GAGAATTACT ACACATGGAC AATRAARATT TCCCCNTCCA GATANACAAT ATATTTTATT     240

TATATTTATA GTTTTAAATT ACAACCAGAG CTTGGCATAT TGTATCTATA CCTTTAATAA     300

ATGCTTTTAA TTTAATAAAT TATTGTTTTC TCTTAGATAT GCAATAATTT TCCCACTATC     360

ATTGATTATT TCCCAGGAAC CCATAACAAA TTACTTAAAA ACCTTGCTTT TATGGAAAGT     420

GATATTTTGG AGAAAGTAAA AGAACACCAA GAATCGATGG ACATCAACAA CCCTCGGGAC     480

TTTATTGATT GCTTCCTGAT CAAAATGGAG AAGGTAAAAT GTTAACAAAA GCTTAGTTAT     540

GTGACTGCTT GCGTATKTGT GATTCATTGA CTAGTTGKGT GTTTACTACG GATGTTTAAC     600

AGGTCAAGGA GTAATGCTTG AGAAGCATAT TTAAGTTTTT ATTGTATGCA TGAATATCCA     660

GTAAGCATCA TAGAAAATGT AAAATTAANT TGTTAAATAA TTAGAATACA TAGAAGAAAT     720

TGTTTAGATA AATATNATCT ATCTGAACAA TAAGGATGTC AGGATAGGAA AAGCTCTGTT     780

TCTGCAGCTT CCAGTGGAGA TCAGCACAGG AGGGAACTTA TTTTTT                    826
```